(12) United States Patent
Wu et al.

(10) Patent No.: US 10,844,098 B2
(45) Date of Patent: Nov. 24, 2020

(54) METHOD FOR PREPARING BACTERIAL POLYSACCHARIDE-MODIFIED RECOMBINANT FUSION PROTEIN AND USE OF THE PROTEIN

(71) Applicant: Institute of Biotechnology, Academy of Military Medical Sciences, China, Beijing (CN)

(72) Inventors: Jun Wu, Beijing (CN); Chao Pan, Beijing (CN); Peng Sun, Beijing (CN); Hengliang Wang, Beijing (CN); Bo Liu, Beijing (CN); Zhehui Peng, Beijing (CN); Li Zhu, Beijing (CN); Shaohong Chang, Beijing (CN); Xin Gong, Beijing (CN); Erling Feng, Beijing (CN); Bin Wang, Beijing (CN); Ming Zeng, Beijing (CN)

(73) Assignee: Institute of Biotechnology, Academy of Military Medical Sciences, China, Beijing (CN)

( * ) Notice: Subject to any disclaimer, the term of this patent is extended or adjusted under 35 U.S.C. 154(b) by 390 days.

(21) Appl. No.: 15/529,592

(22) PCT Filed: Sep. 1, 2015

(86) PCT No.: PCT/CN2015/088737
§ 371 (c)(1),
(2) Date: Mar. 16, 2018

(87) PCT Pub. No.: WO2016/082597
PCT Pub. Date: Jun. 2, 2016

(65) Prior Publication Data
US 2018/0258145 A1   Sep. 13, 2018

(30) Foreign Application Priority Data

Nov. 27, 2014 (CN) .......................... 2014 1 0709118

(51) Int. Cl.
| | | |
|---|---|---|
| A61K 39/40 | (2006.01) | |
| C07K 14/33 | (2006.01) | |
| A61K 39/08 | (2006.01) | |
| A61K 39/104 | (2006.01) | |
| C07K 19/00 | (2006.01) | |
| C12N 15/70 | (2006.01) | |
| C12N 15/74 | (2006.01) | |
| C07K 14/21 | (2006.01) | |
| A61P 31/04 | (2006.01) | |

(52) U.S. Cl.
CPC .............. *C07K 14/33* (2013.01); *A61K 39/08* (2013.01); *A61K 39/104* (2013.01); *C07K 14/212* (2013.01); *C07K 19/00* (2013.01); *C12N 15/70* (2013.01); *C12N 15/74* (2013.01); *A61P 31/04* (2018.01); *C07K 2319/55* (2013.01); *C12Y 204/01* (2013.01); *Y02A 50/30* (2018.01)

(58) Field of Classification Search
None
See application file for complete search history.

(56) References Cited

U.S. PATENT DOCUMENTS

| 2011/0117123 A1 | 5/2011 | Leroy | |
| 2011/0243980 A1* | 10/2011 | Feldman | C12P 21/005 424/193.1 |

FOREIGN PATENT DOCUMENTS

| CN | 1255861 A | 6/2000 |
| CN | 1425465 A | 6/2003 |

OTHER PUBLICATIONS

Ihssen J et al ., Microbial Cell Factories, vol. 9, pp. 1-13, Aug. 11, 2010 (Aug. 11, 2010). (Year: 2010).*
Xu, Minrui et al., Military Medical Sciences, vol. 37, No. 8, Aug. 25, 2013 (Mar. 25, 2013) . (Year: 2013).*
Ihssen et al. (Microbial Cell Factories, vol. 9, pp. 1-13, 2010) (Year: 2010).*
Schultz et al. PLOS vol. 8 issue 5, pp. 1-11 , May 2013.*
International Search Report (ISR) for PCT/CN2015/088737; I.A. fd: Sep. 1, 2015 dated Dec. 9, 2015 State Intellectual Property Office of the P.R. China, Beijing, China.
International Preliminary Report on Patentability (IPRP) including the Written Opinion of the International Searching Authority (PCT Rule 44bis) for PCT/CN2015/088737; I.A. fd: Sep. 1, 2015, dated May 30, 3017, by the International Bureau of WIPO, Geneva, Switzerland.
Ihssen, J. et al., "Production of glycoprotein vaccines in *Escherichia coli*," Microb Cell Fact. Aug. 11, 2010;9:61, (13 pages) doi: 10.1186/1475-2859-9-61, BioMed Central, London, England.

(Continued)

*Primary Examiner* — Jana A Hines
*Assistant Examiner* — Khatol S Shahnan Shah
(74) *Attorney, Agent, or Firm* — Sterne, Kessler, Goldstein & Fox P.L.L.C.

(57) ABSTRACT

The invention provided a method for preparing a bacterial polysaccharide-modified recombinant fusion protein and use of the bacterial polysaccharide-modified recombinant fusion protein. The method comprises: co-expressing a recombinant fusion protein and the *Neisseria meningitidis* O-oligosaccharyltransferase PglL in an O-antigen ligase gene-defective bacterium, and linking a polysaccharides endogenous or exogenous for the bacterium to the recombinant fusion protein by the O-oligosaccharyltransferase PglL, to obtain the bacterial polysaccharide-modified recombinant fusion protein. The protein can be used for preparing antibodies against bacterial polysaccharides and vaccines.

11 Claims, 17 Drawing Sheets
Specification includes a Sequence Listing.

(56) References Cited

OTHER PUBLICATIONS

Xu, M.-R. et al., "Production of O157 polysaccharides-pilin conjugates in *Escherichia coli*," Mil. Med. Sci Aug. 25, 2013;37(8):598-603. doi: 10.7644/j. issn. 1674-9960.2013.08.009, Chinese Academy of Millitary Medical Sciences, Beijing, CN.
First Office Action, and attached Search Report, for Chinese Patent Application No. 201410709118.1, dated Sep. 5, 2018, China National Intellectual Property Administration (CNIPA), Beijing, China.
Xu, M.-R., "Study on preparation of O157 polysaccharides-pilin binding with *Escherichia coli*," Chinese Excellent Master's Thesis Full-test Database, Medical and Health Science and Technology, Dec. 15, 2013, pp. 11, 12, 18-33, 45, 48-59, 61 and 67.
Fisher, AC et al., "Production of secretory and extracellular N-linked glycoproteins in *Escherichia coli*," Appl Environ Microbiol. Feb. 2011;77(3):871-81. doi: 10.1128/AEM.01901-10. Epub Dec. 3, 2010.
Tan, Y et al., "Research and application of protein carriers of polysaccharide-protein conjugate vaccines," Chinese Journal of Vaccines and Immunization, Jul. 2013, issue 4, pp. 355-360.
"Exotoxin A [*Pseudomonas aeruginosa*]," BCT May 29, 2013, NCBI Reference Sequence: accession No. WP_003120572 version 1, retrieved from https://www.ncbi.nlm.nih.gov/protein/489211783?sat=46&satkey=46295136.
Cholera toxin B subunit [synthetic construct], GenBank accession No. ADI59547 version 1, Jun. 16, 2010, Bridge, SH et al, retrieved from https://www.ncbi.nlm.nih.gov/protein/ADI59547.1?report=genbank&log$=protalign&blast_rank=1&RID=PRHNEMV1015.
"Tetanus toxin, partial [*Clostridium tetani*]," GenBank Accession No. AAF73267 version 1, BCT Jun. 26, 2016, He, HJ et al., retrieved from https://www.ncbi.nlm.nih.gov/protein/AAF73267.1?report=genbank&log$=prottop&blast_rank=3&RID=R1RKV811015.
Langdon, RH et al., "N-linked glycosylation in bacteria: an unexpected application," Future Microbiol. May 2009;4(4):401-12. doi: 10.2217/fmb.09.10, published online May 5, 2009.
Zhang, Y et al., Research progress on meningococcal polysaccharide protein conjugate vaccine, Chinese J Immunology, Dec. 2011, issue 12, pp. 1143-1149.
Extended European search report including the supplementary European search report and the European search opinion, for EP Appl. No. 15862847.9, dated May 22, 2018, European Patent Office, Munich Germany.
Faridmoayer, A. et al., "Extreme substrate promiscuity of the *Neisseria* oligosaccharyl transferase involved in protein O-glycosylation," J Biol Chem. Dec. 12, 2008;283(50):34596-604. doi: 10.1074/jbc.M807113200. Epub Oct. 17, 2008, Am. Soc. Biochem. Molec. Biol., Baltimore, MD.
Musumeci, M. et al., "In vitro activity of *Neisseria meningitidis* PglL O-oligosaccharyltransferase with diverse synthetic lipid donors and a UDP-activated sugar," J Biol Chem. Apr. 12, 2013;288(15):10578-87. doi: 10.1074/jbc.M112.432815. Epub Mar. 4, 2013, Am. Soc. Biochem. Molec. Biol., Baltimore, MD.
Kowarik, M. et al., "Definition of the bacterial N-glycosylation site consensus sequence," EMBO J. May 3, 2006;25(9):1957-66. Epub Apr. 13, 2006, IRL Press, Oxford, England.
Examination report under sections 12 & 13 of the Patents Act, 1970 and the Patents Rules, 2003, dated Dec. 19, 2019, from Intellectual Property India, for IN Application No. 201717018987.
Communication pursuant to Article 94(3) EPC, for EP application No. 15 862 847.9, dated Dec. 5, 2019, European Patent Office, Munich, Germany.

\* cited by examiner

METHOD FOR PREPARING BACTERIAL POLYSACCHARIDE-MODIFIED RECOMBINANT FUSION PROTEIN AND USE OF THE PROTEIN

REFERENCE TO SEQUENCE LISTING SUBMITTED ELECTRONICALLY

The content of the electronically submitted substitute sequence listing, file name 3932_0020001_sequencelisting_ST25.txt, size 130,885 bytes; and date of creation Mar. 16, 2018, filed herewith, is incorporated herein by reference in its entirety.

TECHNICAL FIELD

The invention relates to a method for preparing a polysaccharide-modified protein and use of the protein; particularly, relates to a method for preparing a bacterial polysaccharide-modified recombinant fusion protein and use of the protein, and belongs to the field of biomedicine.

BACKGROUND ART

O-polysaccharide (OPS), capsular polysaccharide (CPS) and the like of pathogenic bacteria are generally the important protective antigens, such as OPS of *E. coli* type O157, OPS of *Vibrio cholerae* types O1 and O139, CPS of *Streptococcus pneumoniae* types 4, 6B, 9V, 14, 18C, 19F, 23F, etc., and CPS of *Staphylococcus aureus* types CP5 and CP8. Many antibodies against polysaccharides are the neutralizing antibodies of pathogenic bacteria, and therefore development of polysaccharide vaccines is one of the most important aspects in development of bacterial vaccines.

A lot of polysaccharide vaccines such as pneumonia polysaccharide vaccine, meningitis polysaccharide vaccine, haemophilus influenza polysaccharide vaccine, and Typhoid Vi Polysaccharide Vaccine, have been available in market for many years. However, polysaccharide vaccines have a weak immunologic memory and immunogenicity, particularly in children under 2 years old and old people. The research focus has been changed from development of this class of vaccines to development of polysaccharide-protein conjugate vaccines. Among them, 7-Valent pneumococcal polysaccharide-protein conjugate vaccine, 4-valent meningococca polysaccharide-protein conjugate vaccine, and Haemophilus influenzae type b conjugate vaccine have been available in market, and some polysaccharide-protein conjugate vaccines are in different development phases. However, a chemical process for preparing a polysaccharide-protein conjugate vaccine comprises the following steps: (1) culturing pathogenic bacteria (or vaccine strains thereof) in a large scale, from which polysaccharides are extracted; (2) preparing and purifying a toxin protein such as diphtheria toxin and tetanus toxin, which is used as a carrier protein after inactivation; (3) chemically linking the activated polysaccharide to the carrier protein; and (4) further purifying the cross-linked polysaccharide-protein conjugate to prepare a vaccine. The process has the following problems: (1) there is a certain safety risk when culturing less virulent vaccine stains of pathogenic bacteria in a large scale for extracting polysaccharides, sometimes negative pressure workshops are needed, and for some virulent pathogens, they cannot be cultured in a large scale to extract polysaccharides unless the attenuated strains of the pathogenic bacteria are obtained; (2) the polysaccharides extracted by chemical methods are generally a mixture, and have disadvantages such as low purity, uncontrollable quality, and causing side effects easily; (3) the cross-linking of a polysaccharide to a carrier protein is random, the product has a poor homogenicity, and there are difficulties in purification and quality control; and (4) since there are too many steps in the process, the yield is low and the cost is high.

In recent years, with the development in sequencing technology and bioinformatics, native protein glycosylation systems are found in many bacteria, such as N-glycosylation system in *Campylobacter jejuni*, and O-glycosylation system in *Neisseria meningitidis* and *Pseudomonas aeruginosa*. In these glycosylation systems, the polysaccharide synthesis pathway is very similar to the lipopolysaccharide and capsular polysaccharide synthesis pathways in bacteria, wherein the polysaccharide structure depends on gene clusters for glycosyl synthesis, and the oligosaccharyltransferase has a low specificity for the polysaccharide to be transferred thereby. In the N-glycosylation system in *Campylobacter jejuni*, polysaccharide substrates for N-oligosaccharyltransferase PglB are those which are required to have an acetamido group at the C2 position of the first glycosyl at the reducing terminus, and wherein the second glycosyl cannot be linked to the first glycosyl via a β(1-4) linkage. However, in the O-glycosylation system of *Neisseria meningitidis*, O-oligosaccharyltransferase PglL has no such requirements for polysaccharide substrates. PglL can transfer a polysaccharide which does not have an acetamido group at the C2 position of the first glycosyl at the reducing terminus, to the glycosylation site of a protein, and thus has a wider application prospect. However, there are few researches on the specificity of PglL for protein substrates, and its known substrate is only *Neisseria meningitides* pilin PilE, which restricts its application in preparation of polysaccharide-protein conjugate vaccines.

Contents of Invention

The purpose of the invention is to provide a method for preparing a bacterial polysaccharide-modified recombinant fusion protein and use of the bacterial polysaccharide-modified recombinant fusion protein.

The invention provides a method for preparing a bacterial polysaccharide-modified recombinant fusion protein, comprising co-expressing a recombinant fusion protein and *Neisseria meningitidis* O-oligosaccharyltransferase PglL in an O-antigen ligase gene-defective bacterium, and linking a polysaccharide endogenous or exogenous for the bacterium to the recombinant fusion protein by the *Neisseria meningitidis* O-oligosaccharyltransferase PglL, to obtain the bacterial polysaccharide-modified recombinant fusion protein; the recombinant fusion protein comprises an N-terminal signal peptide, a peptide fragment having a glycosylation site of *Neisseria meningitidis* O-oligosaccharyltransferase PglL, and a carrier protein sequence; the carrier protein is a nontoxic mutant of a bacterial toxin protein or a fragment of a bacterial toxin protein.

The peptide fragment having a glycosylation site of *Neisseria meningitidis* O-oligosaccharyltransferase PglL is located at N-terminus or C-terminus of the carrier protein. The amino acid sequence of the *Neisseria meningitidis* O-oligosaccharyltransferase PglL is set forth in SEQ ID No.26, or a mutant thereof having a similar function. The bacterial polysaccharide-modified recombinant fusion protein is a recombinant fusion protein modified by a polysaccharide endogenous for the bacterium or a recombinant fusion protein modified by a polysaccharide exogenous for the bacterium. Due to the deficiency in O-antigen ligase gene, O-antigen polysaccharide cannot be ligated to lipoid A-core oligosaccharide, and therefore lipopolysaccharide cannot be formed.

In said method, the signal peptide may be a signal peptide such as PelB, DsbA, STII, OmpA, PhoA, LamB, SpA, and Enax. In the invention, DsbA signal peptide is used, and has an amino acid sequence from positions 1 to 19 starting from N-terminus of SEQ ID No.32.

The glycosylation site of Neisseria meningitidis O-oligosaccharyltransferase PglL is the serine at position 63 starting from N-terminus of Neisseria meningitidis pilin PilE. The peptide fragment having the glycosylation site of Neisseria meningitidis O-oligosaccharyltransferase PglL is a peptide fragment of Neisseria meningitidis pilin PilE comprising the serine at position 63 starting from N-terminus of Neisseria meningitidis pilin PilE; particularly, is a peptide fragment comprising at least the amino acids from positions 55 to 66 starting from N-terminus of Neisseria meningitidis pilin PilE; more particularly, is any one of: (1) the peptide fragment set forth in the amino acid sequence from positions 128 to 156 starting from N-terminus of SEQ ID No.32 or a tandem repeat sequence thereof; (2) the peptide fragment set forth in the amino acid sequence from positions 128 to 154 starting from N-terminus of SEQ ID No.34 or a tandem repeat sequence thereof; (3) the peptide fragment set forth in the amino acid sequence from positions 128 to 152 starting from N-terminus of SEQ ID No.36 or a tandem repeat sequence thereof; (4) the peptide fragment set forth in the amino acid sequence from positions 128 to 150 starting from N-terminus of SEQ ID No.38 or a tandem repeat sequence thereof; (5) the peptide fragment set forth in the amino acid sequence from positions 128 to 149 starting from N-terminus of SEQ ID No.40 or a tandem repeat sequence thereof; (6) the peptide fragment set forth in the amino acid sequence from positions 22 to 40 starting from N-terminus of SEQ ID No.48 or a tandem repeat sequence thereof; (7) the peptide fragment set forth in the amino acid sequence from positions 22 to 36 starting from N-terminus of SEQ ID No.50 or a tandem repeat sequence thereof; and (8) the peptide fragment set forth in the amino acid sequence from positions 22 to 33 starting from N-terminus of SEQ ID No.52 or a tandem repeat sequence thereof.

In any of the above methods, the nontoxic mutant of the bacterial toxin protein is a nontoxic mutant of Pseudomonas aeruginosa exotoxin A. The fragment of bacterial toxin protein is cholera toxin B subunit or fragment C of tetanus toxin. The nontoxic mutant of Pseudomonas aeruginosa exotoxin A has an amino acid sequence from positions 20 to 631 starting from N-terminus of SEQ ID No.46. The cholera toxin B subunit has an amino acid sequence from positions 20 to 122 starting from N-terminus of SEQ ID No.32. The fragment C of tetanus toxin has an amino acid sequence from positions 20 to 455 starting from N-terminus of SEQ ID No.60.

In any of the above methods, the amino acid sequence of the recombinant fusion protein is any one of: (1) the amino acid sequence set forth in SEQ ID No.32; (2) the amino acid sequence set forth in SEQ ID No.34; (3) the amino acid sequence set forth in SEQ ID No.36; (4) the amino acid sequence set forth in SEQ ID No.38; (5) the amino acid sequence set forth in SEQ ID No.40; (6) the amino acid sequence set forth in SEQ ID No.46; (7) the amino acid sequence set forth in SEQ ID No.48; (8) the amino acid sequence set forth in SEQ ID No.50; (9) the amino acid sequence set forth in SEQ ID No.52; (10) the amino acid sequence set forth in SEQ ID No.56; (11) the amino acid sequence set forth in SEQ ID No.58; and (12) the amino acid sequence set forth in SEQ ID No.60.

In any of the above methods, the recombinant fusion protein is introduced into the bacterium by a recombinant expression vector, and the recombinant expression vector is obtained by inserting a gene encoding the recombinant fusion protein into the multiple cloning site of pMMB66EH. The gene encoding the recombinant fusion protein is as follows: (1) when the recombinant fusion protein has the amino acid sequence set forth in SEQ ID No.32, its coding gene is set forth in SEQ ID No.31; (2) when the recombinant fusion protein has the amino acid sequence set forth in SEQ ID No.34, its coding gene is set forth in SEQ ID No.33; (3) when the recombinant fusion protein has the amino acid sequence set forth in SEQ ID No.36, its coding gene is set forth in SEQ ID No.35; (4) when the recombinant fusion protein has the amino acid sequence set forth in SEQ ID No.38, its coding gene is set forth in SEQ ID No.37; (5) when the recombinant fusion protein has the amino acid sequence set forth in SEQ ID No.40, its coding gene is set forth in SEQ ID No.39; (6) when the recombinant fusion protein has the amino acid sequence set forth in SEQ ID No.46, its coding gene is set forth in SEQ ID No.45; (7) when the recombinant fusion protein has the amino acid sequence set forth in SEQ ID No.48, its coding gene is set forth in SEQ ID No.47; (8) when the recombinant fusion protein has the amino acid sequence set forth in SEQ ID No.50, its coding gene is set forth in SEQ ID No.49; (9) when the recombinant fusion protein has the amino acid sequence set forth in SEQ ID No.52, its coding gene is set forth in SEQ ID No.51; (10) when the recombinant fusion protein has the amino acid sequence set forth in SEQ ID No.56, its coding gene is set forth in SEQ ID No.55; (11) when the recombinant fusion protein has the amino acid sequence set forth in SEQ ID No 58, its coding gene is set forth in SEQ ID No.57; (12) when the recombinant fusion protein has the amino acid sequence set forth in SEQ ID No.60, its coding gene is set forth in SEQ ID No.59. The multiple cloning site is EcoRI and HindIII site.

In any of the above methods, the Neisseria meningitidis O-oligosaccharyltransferase PglL is introduced into the bacterium by a recombinant expression vector, and the recombinant expression vector is obtained by inserting an expression cassette of the Neisseria meningitidis O-oligosaccharyltransferase PglL into the multiple cloning site of pET28a(+). The expression cassette of the Neisseria meningitidis O-oligosaccharyltransferase PglL is set forth in SEQ ID No.30. The multiple cloning site is BglII site.

In any of the above methods, an exogenous polysaccharide is introduced into the bacterium by a recombinant expression vector comprising a gene cluster for polysaccharide synthesis. The gene cluster for polysaccharide synthesis is set forth in SEQ ID No.79. The recombinant expression vector comprising the gene cluster for polysaccharide synthesis is prepared by the following method: subjecting the DNA molecule set forth in SEQ ID No.79 to double enzyme digestion by AscI and NotI, to obtain a gene fragment; subjecting the DNA molecule set forth in SEQ ID No.82 to double enzyme digestion by AscI and NotI, to obtain a large fragment; and ligating the gene fragment to the large fragment to obtain the recombinant expression vector.

In any of the above methods, the O-antigen ligase gene-defective bacterium is O-antigen ligase gene-defective Shigella flexneri, O-antigen ligase gene-defective Salmonella paratyphi A or O-antigen ligase gene-defective Escherichia coli. Preferably, the O-antigen ligase gene-defective Escherichia coli is a strain of E. coli K12.

In any of the above methods, when the bacterium is *Shigella flexneri*, the method of co-expressing the recombinant fusion protein and *Neisseria meningitidis* O-oligosaccharyltransferase PglL in an O-antigen ligase gene-defective bacterium comprises introducing an expression vector encoding the recombinant fusion protein and an expression vector encoding the *Neisseria meningitidis* O-oligosaccharyltransferase PglL into an O-antigen ligase gene-defective *Shigella flexneri*, and inducing the expression thereof. The *Shigella flexneri* is a large virulence plasmid-deleted *Shigella flexneri*. The method for preparing a large virulence plasmid-deleted *Shigella flexneri* is as follows: introducing pKDinc into the *Shigella flexneri*, deleting the large virulence plasmid based on the plasmid incompatibility, and then removing pKDinc based on temperature-sensitive characteristic of pKDinc. The O-antigen ligase gene is waaI gene. The bacterial polysaccharide-modified recombinant fusion protein is a bacterial polysaccharide-modified recombinant fusion protein obtained by linking O-polysaccharide endogenous for *Shigella flexneri* to the recombinant fusion protein by *Neisseria meningitidis* O-oligosaccharyltransferase PglL.

In any of the above methods, when the bacterium is *Salmonella paratyphi* A, the method of co-expressing the recombinant fusion protein and *Neisseria meningitidis* O-oligosaccharyltransferase PglL in an O-antigen ligase gene-defective bacterium comprises introducing an expression vector encoding the recombinant fusion protein and an expression vector encoding the *Neisseria meningitidis* O-oligosaccharyltransferase PglL into an O-antigen ligase gene-defective *Salmonella paratyphi* A, and inducing the expression thereof. The O-antigen ligase gene is waaL gene. The bacterial polysaccharide-modified recombinant fusion protein is a bacterial polysaccharide-modified recombinant fusion protein obtained by linking O-polysaccharide endogenous for *Salmonella paratyphi* A to the recombinant fusion protein by the *Neisseria meningitidis* O-oligosaccharyltransferase PglL.

In any of the above methods, when the bacterium is a strain of *E. coli* K12, the method of co-expressing the recombinant fusion protein and *Neisseria meningitidis* O-oligosaccharyltransferase PglL in an O-antigen ligase gene-defective bacterium comprises introducing an expression vector encoding the recombinant fusion protein, an expression vector encoding the *Neisseria meningitidis* O-oligosaccharyltransferase PglL, and an expression vector comprising a gene cluster for polysaccharide synthesis fragment into an O-antigen ligase gene-defective strain of *E. coli* K12, and inducing the expression thereof. The O-antigen ligase gene is waaL gene. The strain of *E. coli* K12 is unable to synthesize endogenous O-antigen, as the gene encoding the key glycosyltransferase (i.e., rhamnosyltransferase) in the O-antigen synthesis pathway, wbbL is naturally inactivated. The bacterial polysaccharide-modified recombinant fusion protein is a bacterial polysaccharide-modified recombinant fusion protein obtained by linking a polysaccharide exogenous for the bacterium to the recombinant fusion protein by *Neisseria meningitidis* O-oligosaccharyltransferase PglL. The exogenous polysaccharide is obtained by introducing an expression vector comprising a gene cluster for polysaccharide synthesis into the strain of *E. coli* K12. The gene cluster for polysacchharide synthesis is set forth in SEQ ID No.79. The expression vector comprising the gene cluster for polysaccharide synthesis is prepared by the following method: subjecting the DNA molecule set forth in SEQ ID No.79 to double enzyme digestion by AscI and NotI, to obtain a gene fragment; subjecting the DNA molecule set forth in SEQ ID No.82 to double enzyme digestion by AscI and NotI, to obtain a large fragment; and ligating the gene fragment to the large fragment to obtain the expression vector.

Preferably, any of the above methods further comprises the steps of cell lysis, centrifugation and collection of supernatant, desalting and/or separation and purification, after the expression. The separation and purification is conducted by ion exchange chromatography and/or molecular sieve chromatography.

The bacterial polysaccharide-modified recombinant fusion protein prepared by any of the above methods also falls into the protection scope of the invention.

The invention further seeks to protect a vaccine prepared from the bacterial polysaccharide-modified recombinant fusion protein prepared by any of the above methods. The vaccine can induce generation of antibodies against O-antigen polysaccharides in animal. Preferably, the vaccine comprises an aluminium hydroxide adjuvant.

Use of the bacterial polysaccharide-modified recombinant fusion protein prepared by any of the above methods in the preparation of a product capable of inducing generation of antibodies against O-antigen polysaccharides in animal, also falls into the protection scope of the invention. Preferably, the product is a vaccine. Preferably, the bacterium is *Shigella flexneri, Salmonella paratyphi* A or *Escherichia coli*. Preferably, the vaccine comprises an aluminium hydroxide adjuvant.

Use of the bacterial polysaccharide-modified recombinant fusion protein prepared by any of the above methods in the preparation of a product for preventing and/or treating a disease caused by a bacterium, also falls into the protection scope of the invention. Preferably, the product is a vaccine. Preferably, the bacterium is *Shigella flexneri, Salmonella paratyphi* A or *Escherichia coli*. Preferably, the vaccine comprises an aluminium hydroxide adjuvant.

In the invention, in an O-antigen ligase gene-defective host bacterium, *Neisseria meningitidis* O-oligosaccharyltransferase PglL gene and a recombinant fusion protein gene are co-expressed; or in a host bacterium defective in both an O-antigen ligase gene and O-antigen synthesis gene, *Neisseria meningitidis* O-oligosaccharyltransferase PglL gene, a recombinant fusion protein gene, and a gene cluster for synthesis of exogenous bacterial polysaccharide are co-expressed, to obtain a bacterial polysaccharide-modified recombinant fusion protein.

DESCRIPTION OF DRAWINGS

FIG. 1 shows the results of PCR identification of *S. flexneri* 2a 301ΔpCP.

FIG. 2 shows the results of PCR identification of *S. flexneri* 2a 301ΔpCPΔwaaI.

FIG. 3 shows the verification results of lipopolysaccharide synthesis deficiency in *S. flexneri* 2a 301ΔpCPΔwaaI by silver staining.

FIG. 4 shows the tertiary structure of *Neisseria meningitidis* pilin PilE.

FIG. 5 shows the detection result of glycosylation of the recombinant CTB fusion protein by WB assay.

FIG. 6 shows the detection result of glycosylation of the recombinant EPA fusion protein by WB assay.

FIG. 7 shows the purification result of the glycoprotein rCTB4573-OPS$_{Sf301}$ detected by SDS-PAGE and WB assay.

FIG. 8 shows the purification result of the glycoprotein rEPA4573-OPS$_{Sf301}$ detected by SDS-PAGE and WB assay.

FIG. 9 shows the immunogenicity evaluation of the glycoproteins.

FIG. 10 shows the detection result of glycosylation of the recombinant fusion proteins having multiple glycosylation sites by WB assay.

SPECIFIC MODES FOR CARRYING OUT THE INVENTION

Figure 1:
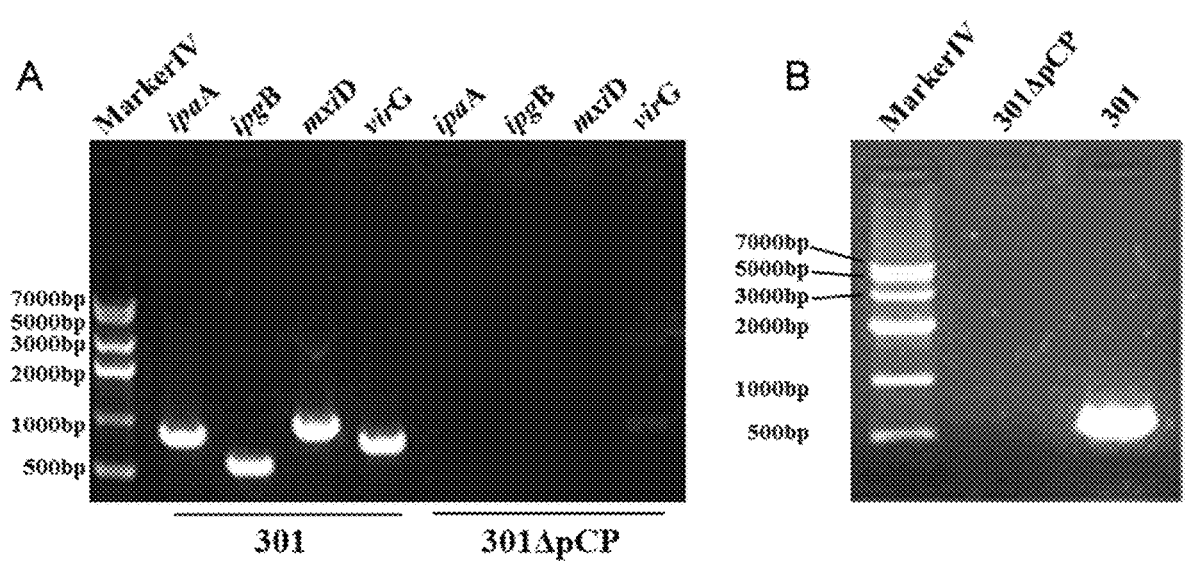
Figure 2:
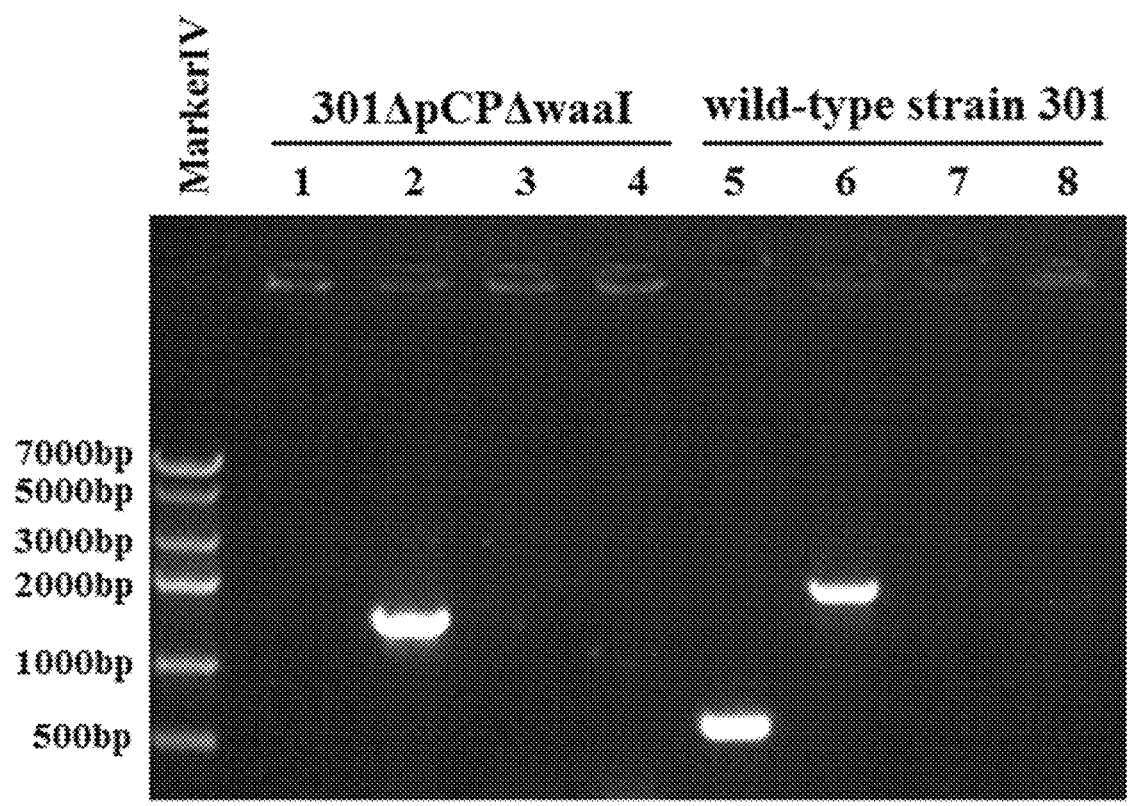
Figure 3:
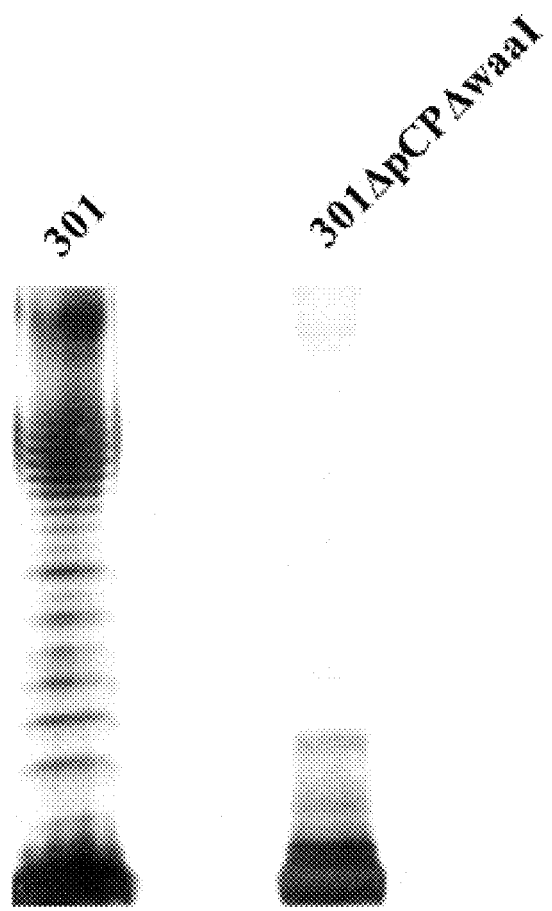

Unless otherwise specified, the experimental methods used in the following examples are the conventional methods. Unless otherwise specified, the materials, reagents and the like used in the following examples are commercially available. pMD18-T was purchased from TaKaRa Company, with a catalog number of D101A. Plasmid pET-22b was purchased from Novagen Company, with a catalog number of 69744. pET28a(+) was purchased from Novagen. pMMB66EH was purchased from ATCC, under an accession number of ATCC 37620. Anti-His tag mouse monoclonal antibody was purchased from Sigma, with a catalog number of A7058. Anti-EPA antibody was purchased from Sigma, with a catalog number of P2318. Rabbit Anti-OPS$_{Sf301}$ antiserum (*Shigella flexneri* 2a type antiserum) was purchased from DENKA SEIKEN Co., Ltd, with a catalog number of 210227. Rabbit anti-*E. coli* O157 antiserum was purchased from DENKA SEIKEN Co., Ltd. with a catalog number of 210753. HRP-goat anti-rabbit IgG was purchased from TransGen Company, with a catalog number of HS-101-01. CHELATING SEPH 6 FF affinity chromatographic column was purchased from GE Healthcare, with a catalog number of 17-5203-06. G25 chromatographic packing was purchased from GE Healthcare. ProteinPak DEAE8HR cation exchange chromatography column was purchased from Waters. Superdex 75 FPLC chromatographic column was purchased from GE Healthcare, with a catalog number of 17-1047-01. Female Balb/c mice were purchased from Laboratory Animal Center of the Academy of Military Medical Sciences. The aluminium hydroxide adjuvant Rehydragel LV was purchased from General Chemical Company.

The recombinant plasmid pKDinc, which has been disclosed in the paper "Global Analysis of a Plasmid-Curred *Shigella flexneri* Strain: New Insights into the Interaction between the Chromosome and a Virulence Plasmid, Journal of Proteome Research, 2010, 9(2):843-854", and is available to the public by Biological Engineering Institute of Academy of Military Medical Sciences, is a temperature-sensitive plasmid resistant to ampicillin. The plasmid pKOBEG, which has been disclosed in the paper "A rapid method for efficient gene replacement in the filamentous fungus *Aspergillus nidulans*[J]. Nucleic Acids Res. 2000 Nov. 15; 28(22): E97", and is available to the public by Biological Engineering Institute of Academy of Military Medical Sciences, is a temperature-sensitive plasmid resistant to chloramphenicol.

The plasmid pCP20, which has been disclosed in the paper "Datsenko, K. A. and B. L. Wanner, One-step inactivation of chromosomal genes in *Escherichia coli* K-12 using PCR products[J]. Proc. natl. Acad. Sci. U.S.A, 2000, 97(12): 6640-6645", and is available to the public by Biological Engineering Institute of Academy of Military Medical Sciences, is resistant to chloramphenicol. pKD3 has been disclosed in "Datsenko, K. A. and B. L. Wanner, One-step inactivation of chromosomal genes in *Escherichia coli* K-12 using PCR products. Proc Natl Acad Sci USA, 2000. 97(12): p. 6640-5.", and is available to the public by Biological Engineering Institute of Academy of Military Medical Sciences. The plasmid pKD46 has been disclosed in the paper "Datsenko, K. A. and B. L. Wanner, One-step inactivation of chromosomal genes in *Escherichia coli* K-12 using PCR products. Proc Natl Acad Sci USA, 2000. 97(12): p. 6640-5.", and is available to the public by Biological Engineering Institute of Academy of Military Medical Sciences. The replicon of pKD46 is sensitive to temperature, and is lost when culturing at 37° C., and the plasmid comprises genes encoding the three recombinases of Red recombination system and controlled by arabinose promoter. pACYC184 has been disclosed in the paper "Yu Mei, Zhou Jianguang, Chenwei, et al., Construction of a mobile recombineering system pYM-Red [J]. PROGRESS IN BIOCHEMISTRY AND BIOPHYSICS, 2005, 32(4): 359-364.", and is available to the public by Biological Engineering Institute of Academy of Military Medical Sciences. *Shigella flexneri* 2a 301 wild-type strain (*S. flexneri* 2a 301) has been disclosed in the paper "Genome sequence of *Shigella flexneri* 2a: insights into pathogenicity through comparison with genomes of *Escherichia coli* K12 and O157, Nucl. Acids Res 2002, 30(20):4432-4441", and is available to the public by Biological Engineering Institute of Academy of Military Medical Sciences. *Salmonella paratyphi* A 50973 strain (*S. paratyphi* CMCC50973) was purchased from National Center for Medical Culture Collections. *E. coli* W3110 has been disclosed in the paper "Yu Mei, Li Shanhu, Chen Wei, et al., Reconstruction of plasmid DNA with Red-mediated homologous recombination combined with restriction digestion [J]. Bulletin of the Academy of Military Medical Sciences, 2005, 29(3): 241-243.", and is available to the public by Biological Engineering Institute of Academy of Military Medical Sciences.

Example 1. Preparation of *Shigella flexneri* O-glycosylated Recombinant Fusion Protein and a Vaccine Thereof by One-Step Bioconjugate Method

*Shigella* spp. is a highly infectious Gram-negative pathogenic enterobacterium, which generally invades the epithelial cells of human colon and is finally located in large intestine, resulting in typical bacillary dysentery (fever, bellyache, tenesmus, and purulent and bloody stool). The large virulence plasmid is the primary pathogenic factor, and the large virulence plasmid comprises about 32 virulence-associated genes, mainly including mxi-spa gene associated with type III secretion system, and virulence genes closely associated with the invasion of bacteria into epithelia, such as ipaBCD and ipgC. In order to develop it into a safe host bacterium, the large plasmid pCP encoding virulent factors has to be deleted first, and then make it be defective in O-antigen ligase gene waaI, so as to develop a host bacterium suitable for the invention.

I. Host Bacterium Engineering (I) Construction of Large Virulence Plasmid-Deficient Strain *S. flexneri* 2a 301ΔpCP 1. Preparation of Competent Cells of *Shigella flexneri* 2a 301 Wild-Type Strain 1) *Shigella flexneri* 2a 301 wild strain (*S. flexneri* 2a 301) was seeded in a LB liquid medium. After culturing at 30° C. overnight, 1 ml culture medium was transferred to 100 mL low salt LB liquid medium, and the culture was carried out at 30° C. until $OD_{600}$ reached 0.6.

2) The bacteria were collected by centrifugation, and washed with a sterilized aqueous solution containing 10% (v/v) glycerol for four times. Finally, the bacteria were re-suspended in 400 μL sterilized aqueous solution containing 10% (v/v) glycerol, to obtain *S. flexneri* 2a 301 competent cells for use in electrotransformation, and were sub-packaged for later use.

2. Deletion of Large Virulence Plasmid 1) inc as a sequence fragment associated with replication in large virulence plasmid pCP of *Shigella* spp., and the recombinant plasmid pKDinc carrying the inc fragment was transformed into the *S. flexneri* 2a 301 competent cells prepared in Step 1 by electroporation, to obtain the intermediate recombinant bacterium, designated as *S. flexneri* 2a 301/pKDinc.

2) The *S. flexneri* 2a 301/pKDinc was passaged serially for more than three times in LB liquid medium containing ampicillin at a concentration of 50 μL, to ensure the loss of large virulence plasmid, and then the cultured bacterial liquid was spread on the ampicillin-resistant LB solid medium. When monoclonal colonies were formed, the genomic DNA of the monoclonal colonies was extracted, and was used as template to carry out PCR amplification, with the primers of ipaA, ipgB, mxiD, virG as primers, respectively. Whether large virulence plasmid pCP was deleted or not was determined by detection of virulence genes ipaA, ipgB, mxiD, and virG, and meanwhile the genomic DNA of *S. flexneri* 2a 301 was used as control to carry out said PCR amplification.

The primers of ipaA are as follows:

```
ipaAp1:
                                          (SEQ ID No. 1)
5'-AAGATTCTGCCTTTGGACC-3' ipaAp2:
                                          (SEQ ID No. 2)
5'-GTGGTTGAAGAGTTCTGTATG-3'
```

The primers of ipgB are as follows:

```
ipgB1U:
                                          (SEQ ID No. 3)
5'-TGCTTTGACGGTATACAGC-3' ipgB1L:
                                          (SEQ ID No. 4)
5'-ACTTCCACAGGTTGAATTCG-3'
```

The primers of mxiD are as follows:

```
mxiDU:
                                          (SEQ ID No. 5)
5'-AAGCAGGTTTCTTCTATTGG-3' mxiDL:
                                          (SEQ ID No. 6)
5'-GAACACATTACCGATTACAGG-3'
```

The primers of virG are as follows:

```
VirGp1:
                                          (SEQ ID No. 7)
5'-CATCAATCCGTTACTCACT-3'

VirGp2:
                                          (SEQ ID No. 8)
5'-ACTACCAGCAACAATACG-3'
```

The results are shown in FIG. 1A. In FIG. 1A, 301 represents *Shigella flexneri* 2a 301 wild-type strain *S. flexneri* 2a 301; and 301ΔpCP represents the monoclonal colonies screened in Step 2). FIG. 1A shows that in the *Shigella flexneri* 2a 301 wild-type strain, the target amplified fragments appeared for the genes ipaA, ipgB, mxiD, virG, which were the target fragment of 888 bp for ipaA, the target fragment of 595 bp for ipgB, the target fragment of 986 bp for mxiD, and the target fragment of 777 bp for virG, respectively. However, in the monoclonal colonies screened for ampicillin-resistance, no amplified fragments appeared for genes ipaA, ipgB, mxiD, virG, indicating successful loss of large virulence plasmid. The monoclonal colonies screened in the Step 2) (based on the plasmid incompatibility, the recombinant bacteria had the large virulence plasmid knocked out and only retained the plasmid pKDinc) were designated as *S. flexneri* 2a 301ΔpCP/pKDinc.

3) By the utilization of the temperature sensitivity of the plasmid pKDinc, *S. flexneri* 2a 301ΔpCP/pKDinc was subjected to continuous culture for two generations in liquid LB medium free of antibiotics at 42° C., and the bacterial strain, which could grow in LB solid medium free of antibiotics, but not in ampicillin-containing LB solid medium, was designated as the bacterial strain *S. flexneri* 2a 301ΔpCP.

The genomic DNA of *S. flexneri* 2a 301ΔpCP was extracted, the virulence genes ipaA, ipgB, mxiD, virG were detected in accordance with the method in Step 2), and meanwhile the genomic DNA of the *Shigella flexneri* 2a 301 wild-type strain *S. flexneri* 2a 301 was used as control to carry out the PCR amplification. The results were consistent with the results in FIG. 1A. In the *Shigella flexneri* 2a 301 wild-type strain *S. flexneri* 2a 301, the target amplified fragments appeared for the genes ipaA, ipgB, mxiD, virG, while in the *S. flexneri* 2a 301ΔpCP, no amplified fragments appeared for the genes ipaA, ipgB, mxiD, virG, indicating the absence of large virulence plasmid.

The genomic DNA of the *S. flexneri* 2a 301ΔpCP was extracted, and the primers of inc were used as primers to carry out PCR amplification. Whether the plasmid pKDinc was successfully deleted or not was confirmed by detection of the inc fragment in the plasmid pKDinc, and meanwhile the genomic DNA of *Shigella flexneri* 2a 301 wild-type strain *S. flexneri* 2a 301 was used as control to carry out the PCR amplification.

The primers of inc are as follows:

```
incF:
                                          (SEQ ID No. 9)
5'-TGCGAGAGAGAGGGGATAAC-3' incR:
                                          (SEQ ID No. 10)
5'-CGCCTTTTCCATCAGTTTC-3'
```

The results are shown in FIG. 1B. In FIG. 1B, 301 represents *Shigella flexneri* 2a 301 wild-type strain *S. flexneri* 2a 301; 301ΔpCP represents *S. flexneri* 2a 301ΔpCP. FIG. 1B shows that in the *Shigella flexneri* 2a 301 wild-type strain S. flexneri 2a 301, the target fragment of 488 bp appeared for inc gene, while in the S. flexneri 2a 301ΔpCP, no target amplified fragment appeared, indicating successful loss of the plasmid pKDinc.

The above results show that the S. flexneri 2a 301ΔpCP had the large virulence plasmid pCP lost, and also had the exogenous plasmid pKDinc lost, i.e., the large virulence plasmid-deleted strain S. flexneri 2a 301ΔpCP was constructed successfully.

(II) The Preparation of O-Antigen Ligase Gene waaI-Defective Avirulent Shigella flexneri S. flexneri 2a 301ΔpCPΔwaaI 1. Preparation of linear targeting DNA fragments 1) Design and Synthesis of PCR Primers A pair of primers were designed for each of the upstream (5'end) and the downstream (3'end) of *Shigella flexneri* 2a 301waaI gene, respectively, i.e., 301waaIu5/301waaIu3 and 301 waaId5/301 waaId3; wherein 301waaIu5 had the restriction enzyme cleavage site for BamHI, 301 waaIu3 had the restriction enzyme cleavage site for SalI, 301waaId5 had the restriction enzyme cleavage site for HindIII, and 301 waaId3 had the restriction enzyme cleavage site for XhoI.

In order to confirm whether the mutant was constructed successfully, a pair of primers (301waaIw5/301waaIw3) located outside the upstream and downstream homologous arms of waaI gene in the genome, a pair of inner primers for identification (301waaIn5/301waaIn3), a pair of primers for kan gene (Kan5/Kan3) and a pair of inner primers for kan gene (Kanf5/Kanf3), were designed to carry out PCR verification, and sequencing verification.

The primers are shown in Table 1 (in Table 1, the underlined sequences refer to the enzyme recognition sites).

TABLE 1

Primer sequence listing 1

| Primer | Sequence (5'→3') | length/ bp | Use |
|---|---|---|---|
| 301waaIu5 | CGGGATCCGGGTATGG GAAGAATCAAG (SEQ ID No. 11) | 628 | for amplification of up fragment |
| 301waaIu3 | GCGTCGACTCAGAAAT GCTACGGTGT (SEQ ID No. 12) | | |
| 301waaId5 | CCAAGCTTTGGACCTT TAGACAATCAA (SEQ ID No. 13) | 680 | for amplification of down fragment |
| 301waaId3 | CCCTCGAGATGTTAGG AAGCATACCG (SEQ ID No. 14) | | |
| 301waaIn5 | TGGGTGGGATTACAAG GT (SEQ ID No. 15) | 562 | for identification of the mutant strain |
| 301waaIn3 | CCAATGACTAACACGG AAA (SEQ ID No. 16) | | |
| 301waaIw5 | CTACAGATGCTGGCGA ATA (SEQ ID No. 17) | 1777 | for identification of the mutant strain |
| 301waaIw3 | TCACTACAGTTGGGAT GG (SEQ ID No. 18) | | |
| Kanf5 | AGCCGAGTCTGTTGTG CC (SEQ ID No. 19) | 1600 | for identification of the mutant strain |
| Kanf3 | TTGTCACTGAAGCGGG AAGG (SEQ ID No. 20) | | |

TABLE 1-continued

Primer sequence listing 1

| Primer | Sequence (5'→3') | length/ bp | Use |
|---|---|---|---|
| Kan5 | GCGTCGACGTGTAGGC TGGAGCTGCTTC (SEQ ID No. 21) | | for identification of the mutant strain |
| Kan3 | CCAAGCTTATGGGAAT TAGCCATGGTCC (SEQ ID No. 22) | | |

2) Construction of Linear Targeting DNA Fragments (1) The genomic DNA of *S. flexneri* 2a 301ΔpCP was used as template, and 301waaIu5/301waaIu3 and 301waaId5/301waaId3 were used to amplify the upstream and downstream homologous arms of waaI, i.e., up and down, respectively.

PCR program was as followed: 94° C. 10 min; 94° C. 30 s, 56° C. 30 s, 72° C. 1 min, 30 cycles, 72° C. 10 min.

The nucleotide sequence of the up fragment obtained by PCR amplification was set forth in the nucleotide sequence from positions 7 to 634 starting from 5'end of SEQ ID No.23, and the nucleotide sequence of the down fragment was set forth in the nucleotide sequence from positions 2143 to 2822 starting from 5'end of SEQ ID No.23.

(2) Construction of pETKan

The DNA molecule set forth in the nucleotide sequence from positions 641 to 2136 starting from 5'end of SEQ ID No.23 was used as template, with 5'-GCGTCGACGTGTAGGCTGGAGCTGCTTC-3'(SEQ ID No.24) and 5'-CCAAGCTTATGGGAATTAGCCATGGTCC-3'(SEQ ID No.25) as primers, to carry out PCR amplification, to obtain a PCR amplification product;

The PCR amplification product was subjected to double enzyme digestion by SalI and HindIII to obtain gene fragments; the plasmid pET-22b was subjected to double enzyme digestion by SalI and HindIII to obtain a large fragment; the gene fragment was ligated to the large fragment, to obtain a recombinant plasmid, designated as pETKan. The pETKan was sequenced, and the result was correct.

(3) The up fragment was subjected to double enzyme digestion by BamHI and SalI, to obtain the gene fragment 1; the plasmid pETKan was subjected to double enzyme digestion by BamHI and SalI, to obtain the large fragment 1; and the gene fragment 1 was ligated to the large fragment 1, to obtain the intermediate vector 1;

The down fragment was subjected to double enzyme digestion by HindIII and XhoI, to obtain the gene fragment 2; the intermediate vector 1 was subjected to double enzyme digestion by HindIII and XhoI, to obtain the large fragment 2; and the gene fragment 2 was ligated to the large fragment 2, to obtain the intermediate vector 2.

(4) The intermediate vector 2 was subjected to double enzyme digestion by BamHI and XhoI, to obtain the targeting fragment of interest, as set forth in SEQ ID No.23. The flanking sequences of the targeting fragment are the homologous arms, and the kan gene was comprised in the middle region. The nucleotide sequence from positions 7 to 634 starting from 5' end of SEQ ID No.23 refer to the up fragment, the nucleotide sequence from positions 641 to 2136 starting from 5' end of SEQ ID No.23 refer to the kan gene, and the nucleotide sequence from positions 2143 to 2822 starting from 5' end of SEQ ID No.23 refer to the down fragment.

2. Construction of S. flexneri 2a 301ΔpCP/pKOBEG

Since the plasmid pKOBEG comprised the genes encoding the enzymes necessary for λ-Red recombination system, the plasmid pKOBEG was transformed into S. flexneri 2a 301ΔpCP by electroporation, and the transformed cells were spread onto the LB-plate containing chloramphenicol at a concentration of 50 μg/mL and cultured at 30° C. overnight, to obtain the positive clone, designated as S. flexneri 2a 301 ΔpCP/pKOBEG strain.

3. Electrotransformation of S. flexneri 2a 301ΔpCP/pKOBEG with the linear targeting DNA fragments 1) The *S. flexneri* 2a 301ΔpCP/pKOBEG was seeded in low salt LB liquid medium containing chloramphenicol at a concentration of 30 μg/mL, cultured at 30° C. overnight, and then passaged in low salt LB liquid medium at a volume ratio of 1:100 for fixture culture.

2) When the $OD_{600}$ value of the culture medium in Step 1) reached 0.2, and L-arabinose was added at a final concentration of 1 mmol/L to induce the expression of Red recombination system.

3) When the $OD_{600}$ of the culture medium in Step 2) reached 0.6, the *S. flexneri* 2a 301ΔpCP/pKOBEG was transformed with the targeting fragments as prepared in Step 1 at a concentration of 300 ng/μL by electroporation, to obtain the transformed cells.

4) To the transformed cells, 1 mL precooled low salt LB liquid medium was added quickly. The cells were thawed at 30° C. for about 2.5 h, and then were spread onto a LB plate containing kanamycin at a concentration of 50 μg/mL, cultured in a 30° C. incubator overnight, to screen out the positive clone.

5) The positive clone was seeded to LB liquid medium containing kanamycin at a concentration of 50 μg/mL, and cultured at 42° C. and passaged twice (12 h for each passage), thereby resulting in the deletion of the plasmid pKOBEG. The kanamycin-resistant, waaI-deleted mutant strain was obtained finally, designated as *S. flexneri* 2a 301ΔpCP waaI::kan1.

4. The plasmid pCP20 encoding a FRT site-specific recombinase was transformed into *S. flexneri* 2a 301ΔpCP waaI::kan by means of electroporation, and cultured in kanamycin-free LB plate containing chloramphenicol at a concentration of 50 μg/mL at 30° C. The positive clone of $Cm^rKm^s$ (chloramphenicol-resistant, kanamycin-sensitive) was screened.

5. The positive clone screened in Step 4, was transferred to liquid LB, and cultured at 42° C. for 12 h, to obtain the O-antigen ligase gene waaI-defective, avirulent *Shigella flexneri* 2a 301, designated as *S. flexneri* 2a 301ΔpCPΔwaaI.

(the replicon of pCP20 was sensitive to temperature, and lost when cultured at 42° C.; the plasmid comprised the DNA encoding FLP recombinase, controlled by temperature-sensitive promoter, and the expression of FLP recombinase was induced when cultured at 42° C., with the deletion of the plasmid.)

(III) Molecular Identification of *S. flexneri* 2a 301ΔpCPΔwaaI

The genomic DNA of *S. flexneri* 2a 301 ΔpCPΔwaaI was used as template, and a pair of waaI inner primers (301waaIn5/301 waaIn3), a pair of waaI outer primers (301waaIw5/301waaIw3), a pair of cross primers (301waaIw5 and kanf3) and kan gene primers (kan5/kan3) were used separately to carry out PCR amplification, and meanwhile the genomic DNA of the wild-type strain *S. flexneri* 2a 301 was used as control to carry out the PCR amplification.

The results are shown in FIG. 2. In FIG. 2, 301ΔpCPΔwaaI represents *S. flexneri* 2a 301ΔpCPΔwaaI, and wild-type strain 301 represents wild-type strain *S. flexneri* 2a 301; 1,5: the PCR product when the waaI inner primers were used as primers; 2,6: the PCR product when the waaI outer primers were used as primers; 3,7: the PCR product when the waaIw5 and kanf3 were used as primers; 4,8: the PCR product when the Kan gene primers were used as primers. FIG. 2 shows that when the genomic DNA of *S. flexneri* 2a 301ΔpCPΔwaaI was used as template, and the waaI inner primers were used as primers to carry out PCR amplification, no target bands appeared; when the waaI outer primers were used as primers to carry out PCR amplification, the bands obtained were smaller than the PCR amplification bands obtained when the genomic DNA of wild-type strain was used as template; no amplification bands appeared when the cross primers and the kan gene primers were used as primers. However, when the genomic DNA of wild-type strain was used as template, and the waaI inner primers were used as primer to carry out PCR amplification, the target bands appeared, and no amplification bands appeared when the cross primers and the kan gene primers were used as primers.

The above results demonstrated that the *S. flexneri* 2a 301ΔpCPΔwaaI was *Shigella flexneri* 2a 301 that was deficient in waaI gene and the large virulence plasmid pCP and had no antibiotic resistance gene.

(IV) Phenotype Identification of *S. flexneri* 2a 301ΔpCPΔwaaI 1 mL culture of *S. flexneri* 2a 301ΔpCPΔwaaI cultured at 37° C. overnight, was centrifuged to collect bacteria. The bacteria were washed with PBS once, and 100 μL lysis buffer (the lysis buffer was prepared by well mixing 2 mL 10% SDS, 0.4 mL 2-mercaptoethanol, 1 mL 100% glycerol, 5 mL 2M pH6.8 Tris-HCl, 20 μL 10% bromophenol blue and 1.6 mL $ddH_2O$) was added and mixed well. After heating in boiling water for 10 min, 4 μL of 20 mg/mL protease K aqueous solution was added, and the reaction was carried out at 60° C. for 1-2 h, to obtain lysates. 15 μl of the lysates was loaded to carry out SDS-PAGE electrophoresis, the gel was placed in the fixing solution overnight, and a sensitizing solution was added and reacted for 30 min. After washing with deionized water for three times, 15 min for each time, a silver nitrate solution was added and reacted for 20 min, and deionized water was used for washing twice, 1 min for each time. A developing solution was added for color development, the reaction was stopped finally, and deionized water was used for washing.

The wild-type strain *S. flexneri* 2a 301 was also subjected to the above experiment, as control.

The results are shown in FIG. 3. In FIG. 3, 301ΔpCPΔwaaI represents *S. flexneri* 2a 301ΔpCPΔwaaI, 301 represents wild-type strain *S. flexneri* 2a 301. FIG. 3 shows that *S. flexneri* 2a 301 wild-type strain had the ladder-like bands of LPS, while *S. flexneri* 2a 301ΔpCPΔwaaI had no ladder-like bands of LPS due to the knockout of O-antigen ligase gene waaI (waaI functions to ligate O-antigen polysaccharide (OPS) to lipoid A-core oligosaccharide to form lipopolysaccharide(LPS)).

II. Identification of Core Peptide Fragments

According to the tertiary structure of *Neisseria meningitidis* pilin PilE (GeneBank: NC_003112.2), polypeptides of different lengths containing serine at position 63 (S63) of PilE (the amino acid is a glycosylation site) were prepared.

To construct a series of recombinant fusion proteins, cholera toxin B submit (CTB) (GenBank: X76390.1) was used as a carrier protein, and the polypeptides of different lengths were fused to the C-temrinus of CTB; alternatively, the nontoxic mutant of *pseudomonas aeruginosa* exotoxin A (rEPA) was used as a carrier protein, and the polypeptides of different lengths were fused to its N-terminus or C-terminus. The recombinant fusion protein and *Neisseria meningitidis* O-oligosaccharyltransferase PglL were co-expressed in *S. flexneri* 2a 301ΔpCPΔwaaI, whole bacterial proteins were subjected to western blot, and detected by specific antibodies, to determine the shortest polypeptide that enabled the recombinant fusion protein to be O-glycosylated. The steps were as followed:

(I) Construction of an Expression Vector of *Neisseria meningitidis* O-Oligosaccharyltransferase PglL 1. The amino acid sequence of *Neisseria meningitidis* O-oligosaccharyltransferase PglL (GeneBank: JN200826.1) is set forth in SEQ ID No.26, and its DNA sequence is set forth in SEQ ID No.27.

The primers 223tac-box5': 5'-ATCG AGATCTACTGCATAATTCGTGTCGCTCAAG-3'(SEQ ID No.28) and 223tac-box3': 5'-ATCG AGATCTGTCTCATGAGCGGATACATATTTG-3' (SEQ ID No.29) were used for amplification to obtain the expression cassette of PglL, set forth in SEQ ID No.30.

2. The DNA molecule set forth in SEQ ID No.30 was subjected to enzyme digestion by BglII, to obtain a gene fragment; pET28a(+) was subjected to enzyme digestion by BglII, to obtain a large fragment; the gene fragment was ligated to the large fragment, to obtain the recombinant plasmid, designated as pETtac28-pglL. The pETtac28-pglL was sequenced, and the result was correct.

(II) Construction of *S. flexneri* 2a 301 ΔpCPΔwaaI/pETtac28-pglL Strain

The pETtac28-pglL was transformed into *S. flexneri* 2a 301 ΔpCPΔwaaI by electroporation, to obtain the *S. flexneri* 2a 301 ΔpCPΔwaaI/pETtac28-pglL strain.

Figure 4:
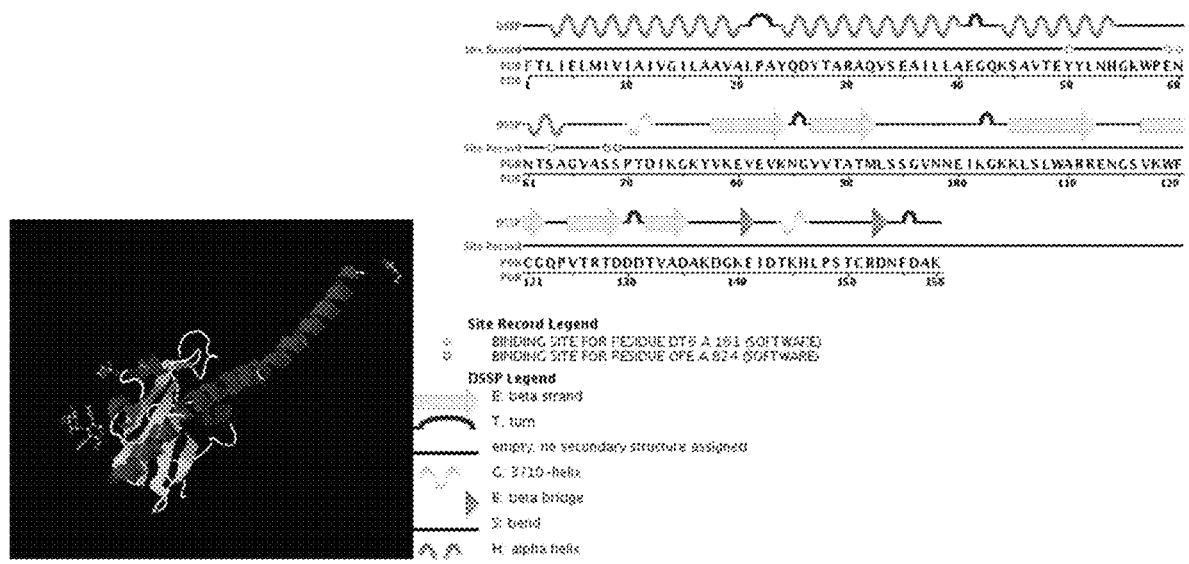

(III) Identification of C-Terminal Sequence of the Core Peptide Fragment that Enables the Recombinant Fusion Protein to be O-Glycosylated 1. Construction of an Expression Vector of Recombinant CTB Fusion Protein According to the tertiary structure of *Neisseria meningitidis* pilin PilE (as shown in FIG. 4), polypeptides of different lengths containing serine (S63) at position 63 of PilE were truncated, CTB was used as carrier protein, and the polypeptides of different lengths were fused to the C-terminus of CTB. The particular method was as followed:

With the N-terminus started from the serine (S45) at position 45 of PilE, and the C-terminus ended at lysine (K73) at position 73 of PilE, 29 amino acids from S45~K73 were truncated, and fused to the C-terminus of CTB; and meanwhile, with the N-terminus of the PilE peptide fragment unchanged, and the C-terminus decreased successively by 2 or 1 amino acids, i.e., the peptide fragments of S45~E71, S45~S69, S45~A67, S45~V66, S45~G65, S45~A64 were fused to the C-terminus of CTB, respectively. In order to avoid steric hindrance effect between CTB and the peptide fragment, CTB was linked to the peptide fragment via 5 amino acids. Since glycosylation occurs in periplasmic space, according to the amino acid sequence of cholera toxin B subunit (X76390.1) published on GenBank, its signal peptide (the first 21 amino acids) was replaced with DsbA signal peptide, and meanwhile the C-terminus of the recombinant fusion protein was fused to a 6×His tag, for the convenience of further detection, thereby constructing a series of recombinant CTB-recombinant fusion protein rCTB4573, rCTB4571, rCTB4569, rCTB4567, rCTB4566, rCTB4565, rCTB4564.

The sequence encoding rCTB4573 is set forth in SEQ ID No.31, wherein starting from 5' end, the sequence from positions 64 to 372 is the CTB coding sequence, the sequence from positions of 388 to 474 is the sequence encoding the amino acids from positions of 45 to 73 of PilE, and the sequence from positions of 7 to 63 is the sequence encoding DsbA signal peptide. The amino acid sequence of the protein rCTB4573 is set forth in SEQ ID No.32, wherein starting from N-terminus, the sequence from positions 20 to 122 is the CTB amino acid sequence, the sequence from positions 123 to 127 is the flexible linker, the sequence from positions 128 to 156 is the amino acids from positions 45 to 73 of PilE, the sequence from positions 157 to 166 is the flexible linker and his-tag, and the sequence from positions 1 to 19 is the DsbA signal peptide sequence.

The sequence encoding rCTB4571 is set forth in SEQ ID No.33, wherein starting from 5' end, the sequence from positions 64 to 372 is the CTB coding sequence, the sequence from positions 388 to 468 is the sequence encoding the amino acids from positions 45 to 71 of PilE, and the sequence from positions 7 to 63 is the sequence encoding DsbA signal peptide. The amino acid sequence of the protein rCTB4571 is set forth in SEQ ID No.34, wherein starting from N-terminus, the sequence from positions 20 to 122 is the CTB amino acid sequence, the sequence from positions 123 to 127 is the flexible linker, the sequence from positions 128 to 154 is the amino acids from positions 45 to 71 of PilE, the sequence from positions 155 to 163 is the flexible linker and his-tag, and the sequence from positions 1 to 19 is the DsbA signal peptide sequence.

The sequence encoding rCTB4569 is set forth in SEQ ID No.35, wherein starting from 5' end, the sequence from positions 64 to 372 is the CTB coding sequence, the sequence from positions 388 to 462 is the sequence encoding the amino acids from positions 45 to 69 of PilE, and the sequence from positions 7 to 63 is the sequence encoding DsbA signal peptide. The amino acid sequence of the protein rCTB4569 is set forth in SEQ ID No.36, wherein starting from N-terminus, the sequence from positions 20 to 122 is the CTB amino acid sequence, the sequence from positions 123 to 127 is the flexible linker, the sequence from positions 128 to 152 is the amino acids from positions 45 to 69 of PilE, the sequence from positions 153 to 161 is the flexible linker and his-tag, and the sequence from positions 1 to 19 is the DsbA signal peptide sequence.

The sequence encoding rCTB4567 is set forth in SEQ ID No.37, wherein starting from 5' end, the sequence from positions 64 to 372 is the CTB coding sequence, the sequence from positions 388 to 456 is the sequence encoding the amino acids from positions 45 to 67 of PilE, the sequence from positions 7 to 63 is the sequence encoding DsbA signal peptide. The amino acid sequence of the protein rCTB4567 is set forth in SEQ ID No.38, wherein starting from N-terminus, the sequence from positions 20 to 122 is the CTB amino acid sequence, the sequence from positions 123 to 127 is the flexible linker, the sequence from positions 128 to 150 is the amino acids from positions 45 to 67 of PilE, the sequence from positions 151 to 159 is the flexible linker and his-tag and the sequence from positions 1 to 19 is the DsbA signal peptide sequence.

The sequence encoding rCTB4566 is set forth in SEQ ID No.39, wherein starting from 5' end, the sequence from positions 64 to 372 is the CTB coding sequence, the sequence from positions 388 to 453 is the sequence encoding the amino acids from positions 45 to 66 of PilE, and the sequence from positions 7 to 63 is the sequence encoding DsbA signal peptide. The amino acid sequence of the protein rCTB4566 is set forth in SEQ ID No.40, wherein starting from N-terminus, the sequence from positions 20 to 122 is the CTB amino acid sequence, the sequence from positions 123 to 127 is the flexible linker, the sequence from positions 128 to 149 is the amino acids from positions 45 to 66 of PilE, the sequence from positions 150 to 158 is the flexible linker and his-tag, and the sequence from positions 1 to 19 is the DsbA signal peptide sequence.

The sequence encoding rCTB4565 is set forth in SEQ ID No.41, wherein starting from 5' end, the sequence from positions 64 to 372 is the CTB coding sequence, the sequence from positions 388 to 450 is the sequence encoding the amino acids from positions 45 to 65 of PilE, and the sequence from positions 7 to 63 is the sequence encoding DsbA signal peptide. The amino acid sequence of the protein rCTB4565 is set forth in SEQ ID No.42, herein starting from N-terminus, the sequence from positions 20 to 122 is the CTB amino acid sequence, the sequence from positions 123 to 127 is the flexible linker, the sequence from positions 128 to 148 is the amino acids from positions 45 to 65 of PilE, the sequence from positions 149 to 157 is the flexible linker and his-tag, and the sequence from positions 1 to 19 is the DsbA signal peptide sequence.

The sequence encoding rCTB4564 is set forth in SEQ ID No.43, wherein starting from 5' end, the sequence from positions 64 to 372 is the CTB coding sequence, the sequence from positions 388 to 447 is the sequence encoding the amino acids from positions 45 to 64 of PilE, and the sequence from positions 7 to 63 is the sequence encoding DsbA signal peptide. The amino acid sequence of the protein rCTB4564 is set forth in SEQ ID No.44, herein starting from N-terminus, the sequence from positions 20 to 122 is the CTB amino acid sequence, the sequence from positions 123 to 127 is the flexible linker, the sequence from positions 128 to 147 is the amino acids from positions 45 to 64 of PilE, the sequence from positions 148 to 156 is the flexible linker and his-tag, and the sequence from positions 1 to 19 is the DsbA signal peptide sequence.

EcoRI and HindIII were used in double enzyme digestion of the DNA molecules set forth in SEQ ID No.31, SEQ ID No.33, SEQ ID No.35, SEQ ID No.37, SEQ ID No.39, SEQ ID No.41, and SEQ ID No.43, to obtain gene fragments, respectively; and EcoRI and HindIII were used in double enzyme digestion of pMMB66EH, to obtain a large fragment; each of the gene fragments was ligated to the large fragment, to obtain the recombinant plasmid, designated as pMMB66EH-rCTB4573, pMMB66EH-rCTB4571, pMMB66EH-rCTB4569, pMMB66EH-rCTB4567, pMMB66EH-rCTB4566, pMMB66EH-rCTB4565, and pMMB66EH-rCTB4564, respectively. The recombinant plasmids were sequenced, and the results were correct.

2. Preparation of Glycoengineered *Shigella flexneri*

The expression vectors pMMB66EH-rCTB4573, pMMB66EH-rCTB4571, pMMB66EH-rCTB4569, pMMB66EH-rCTB4567, pMMB66EH-rCTB4566, pMMB66EH-rCTB4565, and pMMB66EH-rCTB4564 prepared in Step 1 were transformed into the *S. flexneri* 2a 301 ΔpCPΔwaaI/pETtac28-pglL strain prepared in the Step (II) by electroporation, and then the transformed cells were spread onto the LB solid medium containing kanamycin at a final concentration of 50 μg/mL and ampicillin at a final concentration of 100 μg/mL. The positive clones were the glycoengineered *Shigella flexneri*, i.e., *S. flexneri* 2a 301 ΔpCPΔwaaI/pETtac28-pglL/pMMB66EH-rCTB4573, *S. flexneri* 2a 301 ΔpCPΔwaaI/pETtac28-pglL/pMMB66EH-rCTB4571, *S. flexneri* 2a 301 ΔpCPΔwaaI/pETtac28-pglL/pMMB66EH-rCTB4569, *S. flexneri* 2a 301 ΔpCPΔwaaI/pETtac28-pglL/pMMB66EH-rCTB4567, *S. flexneri* 2a 301 ΔpCPΔwaaI/pETtac28-pglL/pMMB66EH-rCTB4566, *S. flexneri* 2a 301 ΔpCPΔwaaI/pETtac28-pglL/pMMB66EH-rCTB4565 and *S. flexneri* 2a 301 ΔpCPΔwaaI/pETtac28-pglL/pMMB66EH-rCTB4564.

3. Glycosylation of Recombinant CTB Fusion Protein and Identification Thereof

The monoclonal colonies of glycoengineered *Shigella flexneri*, *S. flexneri* 2a 301 ΔpCPΔwaaI/pETtac28-pglL/pMMB66EH-rCTB4573, *S. flexneri* 2a 301 ΔpCPΔwaaI/pETtac28-pglL/pMMB66EH-rCTB4571, *S. flexneri* 2a 301 ΔpCPΔwaaI/pETtac28-pglL/pMMB66EH-rCTB4569, *S. flexneri* 2a 301 ΔpCPΔwaaI/pETtac28-pglL/pMMB66EH-rCTB4567, *S. flexneri* 2a 301 ΔpCPΔwaaI/pETtac28-pglL/pMMB66EH-rCTB4566, *S. flexneri* 2a 301 ΔpCPΔwaaI/pETtac28-pglL/pMMB66EH-rCTB4565 and *S. flexneri* 2a 301 ΔpCPΔwaaI/pETtac28-pglL/pMMB66EH-rCTB4564 were seeded in LB medium containing ampicillin at a final concentration of 100 μg/mL and kanamycin a final concentration of 50 μg/mL, and cultured at 37° C.; when $OD_{600}$ was about 0.6, IPTG was added at a final concentration of 1 mM, and the culture was cooled to 16° C. and induced for 20 h.

The next day, 1 mL each of the bacterial liquids induced at 16° C. for 20 h, was centrifuged to extract bacteria, and the extracted bacteria were slowly suspended in 1× reducing buffer (50 mM pH 6.8 Tris-HCl, 1.6% SDS, 0.02% bromophenol blue, 8% glycerol, 20 mM DTT), in a boiling water bath for 10 min, to obtain the sample for electrophoresis. The sample was then subjected to 15% SDS-PAGE electrophoresis. After electrophoresis, the protein was transferred onto PVDF membrane by Bio-Lab Semi-Dry Blotter, at a constant voltage of 20V for 1 h, and detected by Anti-His tag mouse monoclonal antibody, and the results are shown in FIG. 5.

Figure 5:
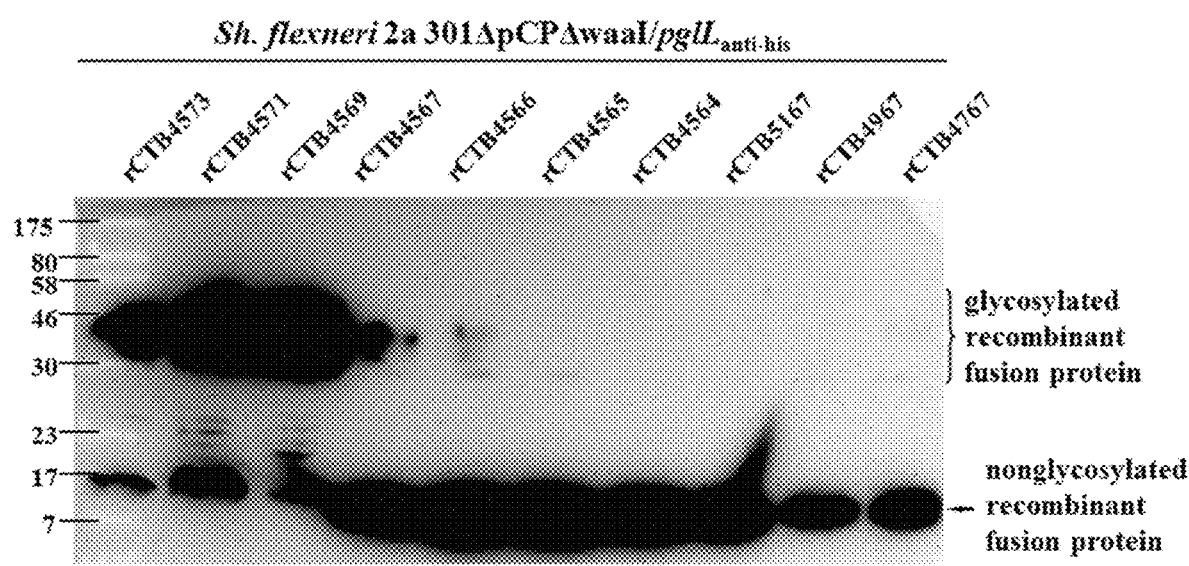

FIG. 5 shows that the truncated PilE peptide fragment with the C-terminus ended at V66, still enabled the recombinant CTB fusion protein to be O-glycosylated, but the glycosylation efficiency was significantly decreased compared to other recombinant CTB fusion proteins modified by a relatively longer peptide fragment.

(IV) Identification of the N-Terminus Sequence of the Core Peptide Fragment that Enables the Recombinant Fusion Protein to be O-Glycosylated 1. Construction of an Expression Vector of the Recombinant EPA Fusion Protein According to the tertiary structure of *Neisseria meningitidis* pilin PilE (as shown in FIG. 4), polypeptides of different lengths containing serine (S63) at position 63 of PilE were truncated, rEPA was used as carrier protein, and the polypeptides of different lengths were fused to the N-terminus or C-terminus of rEPA. The particular method was as followed:

With the N-terminus started from the glycine (G55) at position 55 of PilE, and the C-terminus ended at lysine (K73) at position 73 of PilE, 19 amino acids from G55~K73 were truncated, and fused to the N-terminus of rEPA; or with the N-terminus started from the glycine (G55) at position 55 of PilE, and the C-terminus ended at serine (S69) at position 69 of PilE, 15 amino acids from G55~S69 were truncated, and fused to the N-terminus of rEPA; or with the N-terminus started from the glycine (G55) at position 55 of PilE, and the C-terminus ended at valine (V66) at position 66 of PilE, 12 amino acids from G55~V66 were truncated, and fused to the N-terminus of rEPA; or with the N-terminus started from the proline (P58) at position 58 of PilE, and the C-terminus ended at valine (V66) at position 66 of PilE, 9 amino acids from P58~V66 were truncated, and fused to the N-terminus of rEPA; or with the N-terminus started from the seine (S45) at position 45 of PilE, and the C-terminus ended at lysine (K73) at position 73 of PilE, 29 amino acids from S45~K73 were truncated, and fused to the C-terminus of rEPA; i.e., the peptide fragments of G55~K73, G55~S69, G55~V66, P58~V66 were fused to the N-terminus of rEPA, respectively, or the peptide fragment of S45~K73 was fused to the C-terminus of rEPA. Since glycosylation occurs in periplasmic space, according to the amino acid sequence of *Pseudomonas aeruginosa* exotoxin A (AE004091.2) published on GenBank, its signal peptide (the first 25 amino acids) was replaced with DsbA signal peptide, E at position 553 was deleted, L at position 552 was mutated to V, and the C-terminus of the recombinant fusion protein was fused to a 6×His tag, for the convenience of further detection, thereby constructing a series of recombinant EPA recombinant fusion proteins rEPA5573$_N$, rEPA5569$_N$, rEPA5566$_N$, rEPA5866$_N$, and rEPA4573.

The sequence encoding rEPA4573 is set forth in SEQ ID No.45, wherein starting from 5' end, the sequence from positions 64 to 1899 is the rEPA coding sequence, the sequence from positions 1915 to 2001 is the sequence encoding the amino acids from positions 45 to 73 of PilE, and the sequence from positions 7 to 63 is the sequence encoding DsbA signal peptide. The amino acid sequence of the protein rEPA4573 is set forth in SEQ ID No.46, wherein starting from N-temrinus, the sequence from positions 20 to 631 is the rEPA amino acid sequence, the sequence from positions 632 to 636 is the flexible linker, the sequence from positions 637 to 665 is the amino acids from positions 45 to 64 of PilE, the sequence from positions 666 to 674 is the flexible linker and his-tag, and the sequence from positions 1 to 19 is the DsbA signal peptide sequence.

The sequence encoding rEPA5573$_N$ is set forth in SEQ ID No.47, wherein starting from 5' end, the sequence from positions 70 to 126 is the sequence encoding the amino acids from positions 55 to 73 of PilE, the sequence from positions 133 to 1962 is the rEPA coding sequence, and the sequence from positions 7 to 63 is the sequence encoding DsbA signal peptide. The amino acid sequence of the protein rEPA5573$_N$ is set forth in SEQ ID No.48, wherein starting from N-terminus, the sequence from positions 22 to 40 is the amino acids from positions 55 to 73 of PilE, the sequence from positions 41 to 42 is the flexible linker, the sequence from positions 43 to 652 is the rEPA amino acid sequence, the sequence from positions 653 to 666 is the flexible linker and his-tag, and the sequence from positions 1 to 19 is the DsbA signal peptide sequence.

The sequence encoding rEPA5569$_N$ is set forth in SEQ ID No.49, wherein starling from 5' end, the sequence from positions 70 to 114 is the sequence encoding the amino acids from positions 55 to 69 of PilE, the sequence from positions 121 to 1950 is the rEPA coding sequence, the sequence from positions 7 to 63 is the sequence encoding DsbA signal peptide. The amino acid sequence of the protein rEPA5569$_N$ is set forth in SEQ ID No.50, wherein starting from N-terminus, the sequence from positions 22 to 36 is the amino acids from positions 55 to 69 of PilE, the sequence from positions 37 to 38 is the flexible linker, the sequence from positions 39 to 648 is the rEPA amino acid sequence, the sequence from positions 649 to 662 is the flexible linker and his-tag, and the sequence from positions 1 to 19 is the DsbA signal peptide sequence.

The sequence encoding rEPA5566$_N$ is set forth in SEQ ID No.51, wherein starting from 5' end, the sequence from positions 70 to 105 is the sequence encoding the amino acids from positions 55 to 66 of PilE, the sequence from positions 112 to 1941 is the rEPA coding sequence, and the sequence from positions 7 to 63 is the sequence encoding DsbA signal peptide. The amino acid sequence of the protein rEPA5566$_N$ is set forth in SEQ ID No.52, wherein starting from N-terminus, the sequence from positions 22 to 33 is the amino acids from positions 55 to 66 of PilE, the sequence from positions 34 to 35 is the flexible linker, the sequence from positions 36 to 645 is the rEPA amino acid sequence, the sequence from positions 646 to 659 is the flexible linker and his-tag, and the sequence from positions 1 to 19 is the DsbA signal peptide sequence.

The sequence encoding rEPA5866$_N$ is set forth in SEQ ID No.53, wherein starting from 5' end, the sequence from positions 70 to 96 is the sequence encoding the amino acids from positions 58 to 66 of PilE, the sequence from positions 103 to 1932 is the rEPA coding sequence, and the sequence from positions 7 to 63 is the sequence encoding DsbA signal peptide. The amino acid sequence of the protein rEPA5866$_N$ is set forth in SEQ ID No.54, wherein starting from N-terminus, the sequence from positions 22 to 30 is the amino acids from positions 58 to 66 of PilE, the sequence from positions 31 to 32 is the flexible linker, the sequence from positions 33 to 642 is the rEPA amino acid sequence, the sequence from positions 643 to 656 is the flexible linker and his-tag, and the sequence from positions 1 to 19 is the DsbA signal peptide sequence.

EcoRI and HindIII were used in double enzyme digestion of the DNA molecules set forth in SEQ ID No.45, SEQ ID No.47, SEQ ID No.49, SEQ ID No.51, and SEQ ID No.53, to obtain gene fragments, respectively; EcoRI and HindIII were used in double enzyme digestion of pMMB66EH, to obtain a large fragment; each of the gene fragments was ligated to the large fragment to obtain the recombinant plasmid, designated as pMMB66EH-rEPA4573, pMMB66EH-rEPA5573$_N$, pMMB66EH-rEPA5569$_N$, pMMB66EH-rEPA5566$_N$, and pMMB66EH-rEPA5866$_N$, respectively. The recombinant plasmids were sequenced, and the results were correct.

2. Preparation of Glycoengineered *Shigella flexneri*

The expression vectors pMMB66EH-rEPA4573, pMMB66EH-rEPA5573$_N$, pMMB66EH-rEPA5569$_N$, pMMB66EH-rEPA5566$_N$, and pMMB66EH-rEPA5866$_N$ prepared in Step 1 were electrotransformed into *S. flexneri* 2a 301 ΔpCPΔwaaI/pETtac28-pglL strain prepared in the Step (II), respectively, and the transformed cells were spread onto LB solid medium containing kanamycin at a final concentration of 50 μg/mL and ampicillin at a final concentration of 100 μg/mL. The positive clones were the glycoengineered *Shigella flexneri*, i.e., *S. flexneri* 2a 301 ΔpCPΔwaaI/pETtac28-pglL/pMMB66EH-rEPA4573, *S. flexneri* 2a 301 ΔpCPΔwaaI/pETtac28-pglL/pMMB66EH-rEPA5573$_N$, *S. flexneri* 2a 301 ΔpCPΔwaaI/pETtac28-pglL/pMMB66EH-rEPA5569$_N$, *S. flexneri* 2a 301 ΔpCPΔwaaI/pETtac28-pglL/pMMB66EH-rEPA5566$_N$, and *S. flexneri* 2a 301 ΔpCPΔwaaI/pETtac28-pglL/pMMB66EH-rEPA5866$_N$.

3. Glycosylation of EPA Fusion Protein and Identification Thereof

The monoclonal colonies of glycoengineered bacteria *S. flexneri* 2a 301 ΔpCPΔwaaI/pETtac28-pglL/pMMB66EH-rEPA4573, *S. flexneri* 2a 301 ΔpCPΔwaaI/pETtac28-pglL/pMMB66EH-rEPA5573$_N$, *S. flexneri* 2a 301 ΔpCPΔwaaI/pETtac28-pglL/pMMB66EH-rEPA5569$_N$, *S. flexneri* 2a 301 ΔpCPΔwaaI/pETtac28-pglL/pMMB66EH-rEPA5566$_N$, and S. flexneri 2a 301 ΔpCPΔwaaI/pETtac28-pglL/pMMB66EH-rEPA5866$_N$, were seeded in LB medium containing ampicillin at a final concentration of 100 µg/mL and kanamycin at a final concentration of 50 µg/mL, and cultured at 37° C. When the OD$_{600}$ was about 0.6, IPTG was added at a final concentration of 1 mM, and the culture were cooled to 16° C. and induced for 20 h.

The next day, 1 mL each of the bacterial liquids induced at 16° C. for 20 h, was centrifuged to extract the bacteria, and the extracted bacteria were slowly suspended in 1× reducing buffer, in a boiling water bath for 10 min, to obtain the sample for electrophoresis. The sample was subjected to 8% SDS-PAGE electrophoresis. After electrophoresis, the protein was transferred onto PVDF membrane by Bio-Lab Semi-Dry Blotter, at a constant voltage of 20V for 1 h, and detected by anti-EPA antibody, and the results are shown in FIG. 6.

Figure 6:
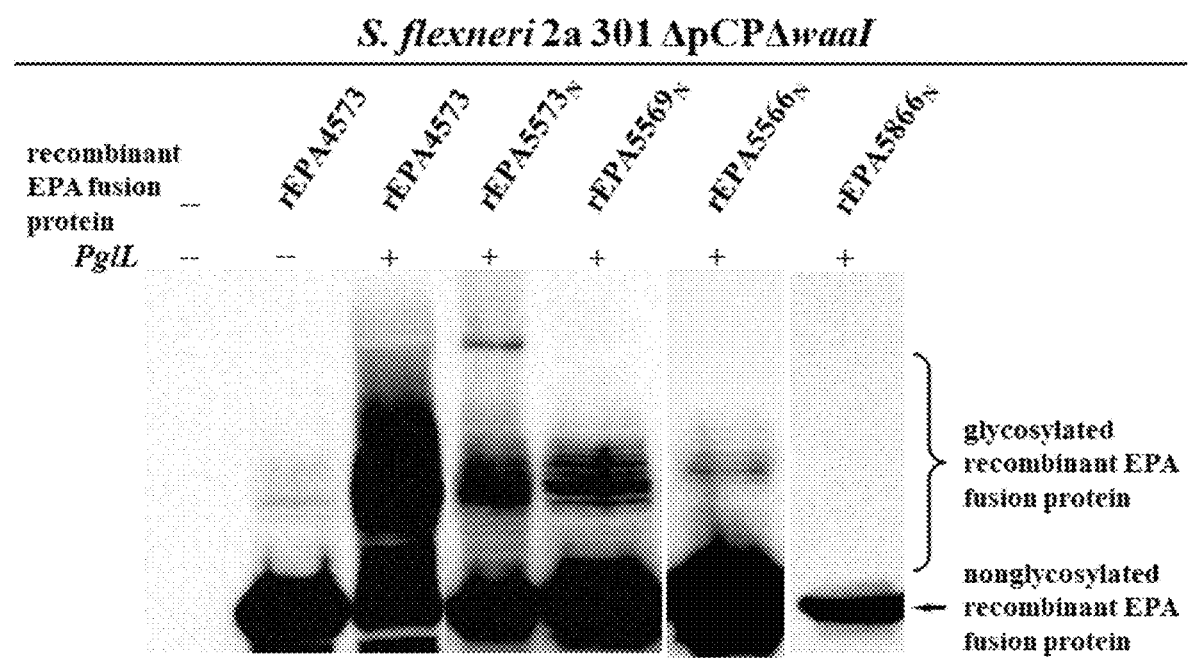

FIG. 6 shows that the truncated PilE proteins, i.e., the peptide fragments of G55~K73, G55~S69, and G55~V66, fused to the N-terminus of EPA protein, still successfully enabled the recombinant EPA fusion protein to be O-glycosylated, but the glycosylation efficiency of the recombinant EPA fusion protein gradually decreased with the shortening of the truncated peptide fragment.

The above results show that the core peptide fragment, which enables the recombinant fusion protein to be O-glycosylated, is G55~V66 of PilE. However, in view of the practical application, in the invention, relevant studies are carried out by fusing the amino acid sequence of P1a (i.e., S45~K73 of PilE) (PilE with a Genbank accession number of NC_003112.2) to a different carrier protein at a suitable position.

III. Preparation of *Shigella flexneri* O-Polysaccharide-Recombinant CTB Fusion Protein Conjugate by One-Step Bioconjugate Method (I) The monoclonal colony of the glycoengineered bacterium *S. flexneri* 2a 301 ΔpCPΔwaaI/pETtac28-pglL/pMMB66EH-rCTB4573, was seeded to LB medium containing 100 µg/mL ampicillin and 50 µg/mL kanamycin, and cultured at 37° C. When OD$_{600}$ was about 0.6, IPTG was added at a final concentration of 1 mM, and the culture was cooled to 16° C. and induced for 20 h.

(II) Purification of O-polysaccharide-recombinant CTB fusion protein conjugate rCTB4573-OPS$_{Sf301}$ 1. Sample Pretreatment To 10 g bacteria induced at 16° C. for 20 h in the Step (I), 100 mL purified water was added. The bacteria were broken ultrasonically (ultrasonication for 3 s and pause for 5 s, with an accumulative period of ultrasonication for 30 min), and centrifuged at 1200 g. The supernatant as collected, and a sample loading buffer (20 mM pH7.5 Tris-HCl, 0.2M NaCl, 10 mM imidazole) was added to the supernatant. After well stirring, centrifugation was carried out at 12000 g again. The supernatant was collected, and the supernatant was the crude extract containing O-polysaccharide-recombinant CTB fusion protein conjugate rCTB4573-OPS$_{Sf301}$.

2. Purification of a Sample with Chelating Affinity Chromatographic Column

The sample was preliminarily purified with Chelating affinity chromatographic column (Φ1.6 cm*15 cm).

Firstly, the column was washed with at least three column volumes of 0.5M NaOH aqueous solution, and then equilibrated with deionized water to a neutral pH. The column was then equilibrated with at least 3 column volumes of 0.5M NiSO$_4$ aqueous solution, further equilibrated with at least one column volume of B1 solution (20 mM pH7.5 Tris-HCl, 0.5M NaCl, 500 mM imidazole), and finally equilibrated with at least 3 column volumes of A1 solution (20 mM pH7.5 Tris-HCl, 0.5M NaCl, 10 mM imidazole), all at a flow rate of 4 mL/min. The crude extract of rCTB4573-OPS$_{Sf301}$ obtained in Step 1 was loaded from A pipeline, and A1 solution (20 mM pH7.5 Tris-HCl, 0.5M NaCl, 10 mM imidazole) was used to wash the unbound protein, until the ultraviolet absorption (280 nM) was close to 0 mAU. Finally, 100% B1 (20 mM pH7.5 Tris-HCl, 0.5M NaCl, 500 mM imidazole) was used for elution, and 30 mL eluate was collected to obtain the preliminarily purified sample.

3. Sample Desalting

The preliminarily purified sample obtained in Step 2 was desalted with G25 fine chromatographic column (Φ1.6 cm*30 cm), wherein the mobile phase was A2 solution (20 mM pH5.4 HAc—NaAc).

Firstly, the column was washed with at least 3 column volumes of 0.5M NaOH aqueous solution, then equilibrated with deionized water to a neutral pH, and finally equilibrated with at least 3 column volumes of A2 solution. The preliminarily purified sample obtained in Step 2 was loaded from A pipeline, wherein the mobile phase was A2 solution (20 mM pH5.4 HAc—NaAc). 60 mL sample was collected to obtain the desalted sample. And all the flow rates involved in each step of the above described process were 4 mL/min.

4. Further Purification of rCTB4573-OPS$_{Sf301}$ with ProteinPak SP8HR Cation Exchange Chromatographic Column The desalted sample obtained in Step 3 was further purified with ProteinPak SP8HR cation exchange chromatographic column.

Firstly, the column was washed with at least 3 column volumes of 0.5M NaOH aqueous solution, and then equilibrated with deionized water to a neutral pH. The column was then equilibrated with at least 3 column volumes of A2 solution (20 mM pH5.4 HAc—NaAc). The sample was loaded from A pipeline, the A2 solution was used to wash the unbound glycoprotein, and linear elution from 0 to 50% B2 solution was carried out (the A2 solution entered from A pipeline and the B2 solution entered from B pipeline, were automatically mixed by the purifier) within 30 min. The eluate was collected. And all the flow rates involved in each step of the above described process were 1 mL/min. The peak of the glycoprotein rCTB4573-OPS$_{Sf301}$ appeared with an electric conductivity of about 35~45 mS/cm, i.e., the target protein rCTB4573-OPS$_{Sf301}$.

Figure 7:
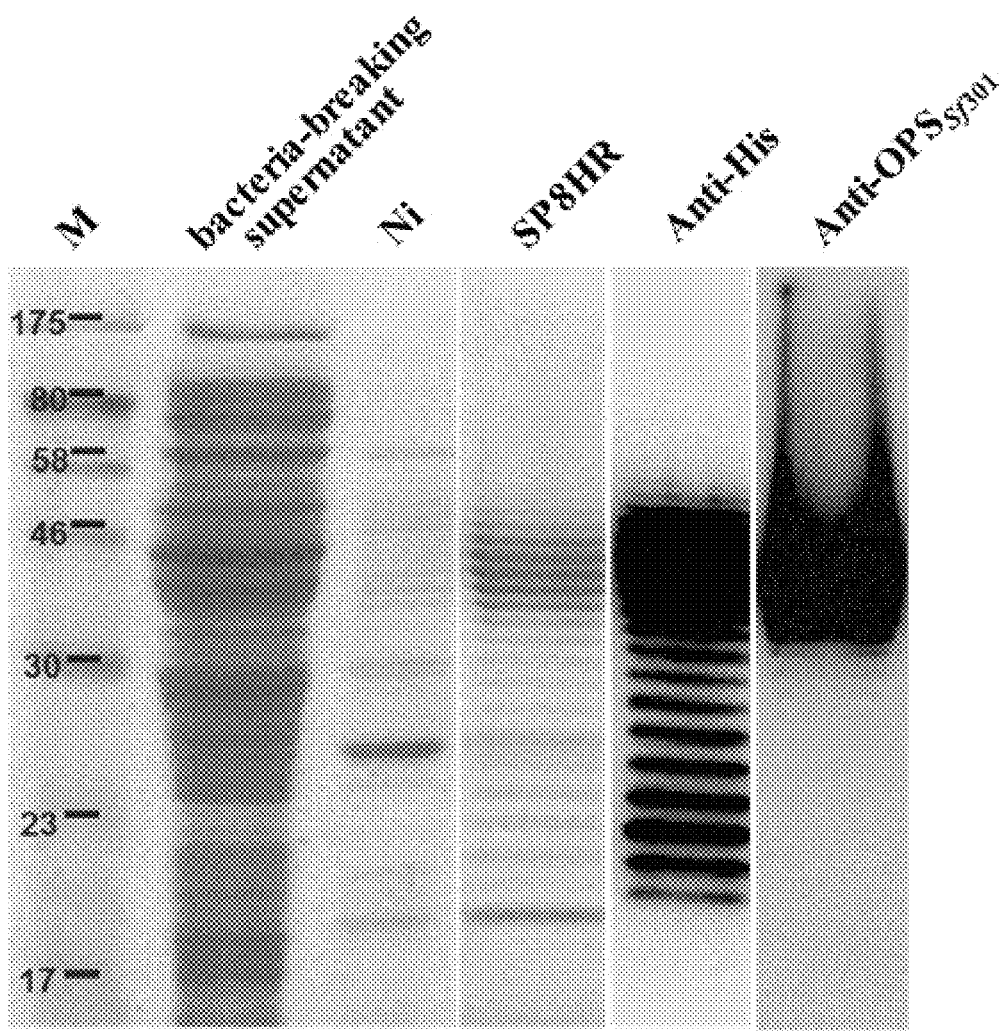

The sample was analyzed by 12% SDS-PAGE and western blot, and the results are shown in FIG. 7. In FIG. 7, M represents protein marker bacteria-breaking supernatant represents the crude extract of rCTB4573-OPS$_{Sf301}$ obtained in Step 1; Ni represents the preliminarily purified sample obtained in Step 2; SP8HR represents the target protein rCTB4573-OPS$_{Sf301}$ further purified by ProteinPak SP8HR cation exchange chromatographic column; anti-His represents the western blot result by Anti-His tag mouse monoclonal antibody; and anti-OPS$_{Sf301}$ represents the western blot result by rabbit Anti-OPS$_{Sf301}$ antiserum.

IV. Preparation of *Shigella flexneri* O-Polysaccharide-Recombinant EPA Fusion Protein Conjugate by One-Step Bioconjugate Method (I) The monoclonal colony of glycoengineered bacterium *S. flexneri* 2a 301 ΔpCPΔwaaI/pETtac28-pglL/pMMB66EH-rEPA4573, was seeded to a LB medium containing 100 μg/mL ampicillin and 50 μg/mL kanamycin, and cultured at 37° C. When $OD_{600}$ was about 0.6, IPTG was added at a final concentration of 1 mM, and the culture was cooled to 16° C. and induced for 20 h.

(II) Purification of O-polysaccharide-recombinant EPA fusion protein conjugate rEPA4573-OPS$_{Sf301}$

1. Sample Pretreatment

To 10 g bacteria induced at 16° C. for 20 h in the Step (1), 100 mL purified water was added. The bacteria were broken ultrasonically (ultrasonation for 3 s and pause for 5 s, with an accumulative period of ultrasonation for 30 min), and centrifuged at 12000 g. The supernatant was collected, a sample loading buffer (20 mM pH7.5 Tris-HCl, 0.2M NaCl, 10 mM imidazole) was added to the supernatant. After well stirring, the centrifugation was carried out at 12000 g again. The supernatant was collected, and the supernatant was the crude extract containing the O-antigen polysaccharide-recombinant EPA fusion protein conjugate rEPA4573-OPS$_{S/301}$.

2. Purification of a Sample with Chelating Affinity Chromatographic Column

The sample was preliminarily purified with Chelating affinity chromatographic column (Φ1.6 cm*15 cm).

Firstly, the column was washed with at least three column volumes of 0.5M NaOH aqueous solution, and then equilibrated with deionized water to a neutral pH. The column was then equilibrated with at least 3 column volumes of 0.5M NiSO$_4$ aqueous solution, further equilibrated with at least one column volume of B1 solution (20 mM pH7.5 Tris-HCl, 0.5M NaCl, 500 mM imidazole), and finally equilibrated with at least 3 column volumes of A1 solution (20 mM pH7.5 Tris-HCl, 0.5M NaCl, 10 mM imidazole), all at a flow rate of 4 mL/min. The crude extract of rEPA4573-OPS$_{S/301}$ obtained in Step 1 was loaded from A pipeline, and A1 solution (20 mM pH7.5 Tris-HCl, 0.5M NaCl, 10 mM imidazole) was used to wash the unbound protein. Finally, 100% B1 (20 mM pH7.5 Tris-HCl, 0.5M NaCl, 500 mM imidazole) was used for elution, and 30 mL eluate was collected to obtain the preliminarily purified sample.

3. Sample Desalting

The sample preliminarily purified with Chelating affinity chromatographic column was desalted with G25 fine chromatographic column (Φ1.6 cm*30 cm), wherein the mobile phase was A3 solution (20 mM pH7.5 Tris-HCl).

Firstly, the column was washed with at least 3 column volumes of 0.5M NaOH aqueous solution, then equilibrated with deionized water to a neutral pH, and finally equilibrated with at least 3 column volumes of A3 solution. The preliminarily purified sample obtained in Step 2 was loaded from A pipeline, and 60 mL sample was collected to obtain the desalted sample, wherein the mobile phase was A3 solution (20 mM pH7.5 Tris-HCl). And all the flow rates involved in each step of the above described process were 4 mL/min.

4. Further Purification of rEPA4573-OPS$_{S/301}$ with ProteinPak DEAE8HR Anion Exchange Chromatographic Column The desalted sample obtained in Step 3 was further purified with ProteinPak DEAE8HR anion exchange chromatographic column (waters).

Firstly, the column was washed with at least 3 column volumes of 0.5M NaOH aqueous solution, and then equilibrated with deionized water to a neutral pH. The column was then equilibrated with at least 3 column volumes of A3 solution (20 mM pH7.5 Tris-HCl). The sample was loaded from A pipeline, the A3 solution was used to wash the unbound glycoprotein, and linear elution from 0 to 50% B3 solution was carried out (the A3 solution entered from A pipeline, and the B3 solution entered from B pipeline, were automatically mixed by the purifier) within 30 min. The eluate was collected. And all the flow rates involved in each step of the above described process were 1 mL/min. The peak of the glycoprotein rEPA4573-OPS$_{S/301}$ appeared with an electric conductivity of about 8~18 mS/cm, i.e., the crude extract of the target protein rEPA4573-OPS$_{S/301}$.

5. Fine Purification of rEPA4573-OPS$_{S/301}$ with Superdex 75 Chromatographic Column The sample purified with ProteinPak DEAE8HR anion exchange chromatographic column was further purified with Superdex 75 FPLC(Φ1 cm*30 cm, GE Company).

Firstly, the column was washed with at least 3 column volumes of 0.5M NaOH aqueous solution, and than equilibrated with deionized water to a neutral pH. The column was then equilibrated with at least 3 column volumes of A4 solution (20 mM pH7.5 PB, 0.9 g/100 ml NaCl), and 1 mL of the crude extract of the protein rEPA4573-OPS$_{S/301}$ was loaded via a loading loop. 8~11 mL effluent sample was collected. The sample was the finely purified rEPA4573-OPS$_{S/301}$, i.e., the target protein rEPA4573-OPS$_{S/301}$.

The sample was analyzed by 8% SDS-PAGE and western blot, and the S. flexneri 2a 301 ΔpCPΔwaaI/pMMB66EH-rEPA4573, which as transformed only with pMMB66EH-rEPA4573, but not with pETtac28-pglL, was used as control.

Figure 8:
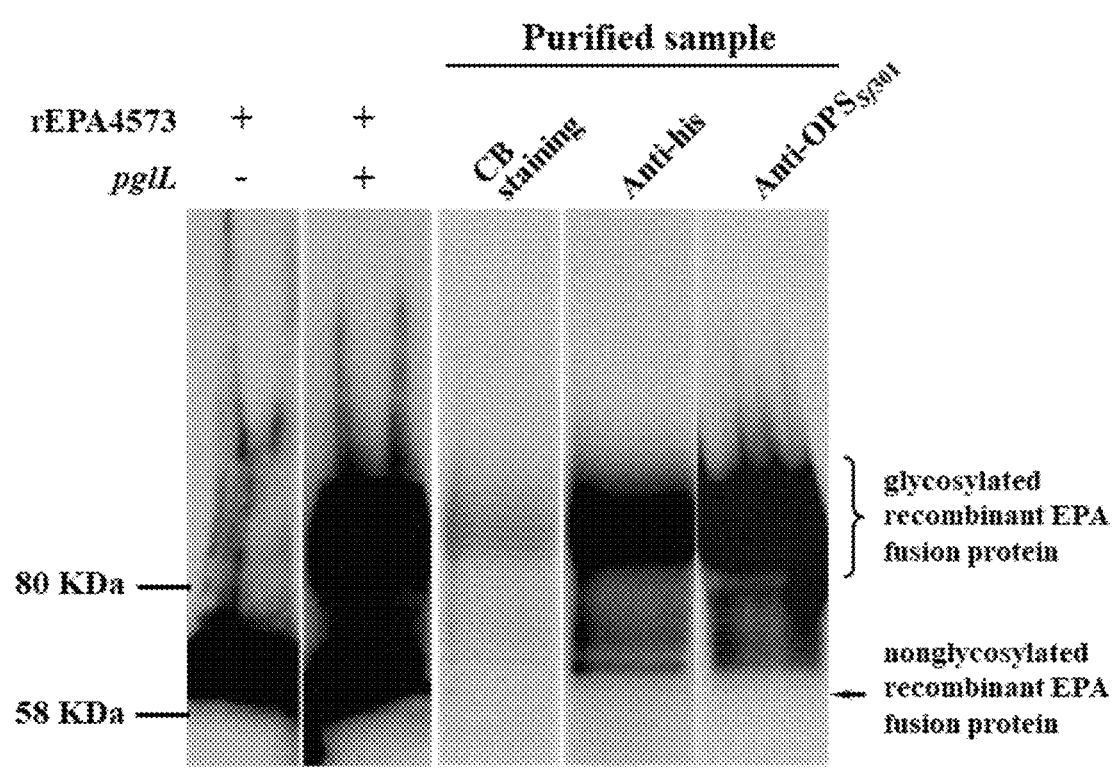

The results are shown in FIG. 8. In FIG. 8, from left to right, Lane 1 represents the control protein; Lane 2 represents the crude extract of rEPA4573-OPS$_{S/301}$ obtained in Step 1; the purified sample represents the target protein rEPA4573-OPS$_{S/301}$ finely purified in Step 5; CB straining represents the Commassie Blue staining result of the purified sample; Anti-his represents the western blot result by Anti-His tag mouse monoclonal antibody; Anti-OPS$_{S/301}$ represents the western blot result by rabbit Anti-OPS$_{S/301}$ antiserum.

V. Preparation and Animal Experiment Evaluation of rCTB4573-OPS$_{S/301}$ and rEPA4573-OPS$_{S/301}$ Polysaccharide-Protein Conjugate Vaccines (I) Preparation of rCTB4573-OPS$_{S/301}$ and rEPA4573-OPS$_{S/301}$ polysaccharide-protein conjugate vaccines The rCTB4573-OPS$_{S/301}$ purified in Step III and the rEPA4573-OPS$_{S/301}$ purified in Step IV were sterilized by filtration, and separately mixed with aluminium hydroxide adjuvant in a volume ratio of 9:1, to obtain the samples of rCTB4573-OPS$_{S/301}$ and rEPA4573-OPS$_{S/301}$ for intraperitoneal injection.

(II) Animal Immunization with rCTB4573-OPS$_{S/301}$ and rEPA4573-OPS$_{S/301}$ and Effect Evaluation Thereof

1. Preparation of O-Antigen (OPS$_{S/301}$)

LPS (see, the paper "Sun Yang, Feng Shuzhang, Zhu Lingwei, et al., Preparation and identification of monoclonal antibodies against LPS of entero-hemorrhagic E. coli O157 [J]. Chinese Journal of Zoonoses, 2007, 23(10): 971-973.") was extracted by means of hot phenol-water extraction, and lyophilized. The lyophilized sample was dissolved in 1% glacial acetic acid at a concentration of 10 mg/ml, in a boiling water bath for 90 min, and then cooled to room temperature. pH was adjusted to 7.0. After centrifugation at 64000×g for 5 h, the supernatant was collected, and was lyophilized after extensive dialysis with deionized water.

2. Mouse Experiment 40 6-week-old female Balb/c mice, were randomly divided into the following four groups: the aluminium hydroxide group, the OPS$_{S/301}$ group, the rCTB4573-OPS$_{S/301}$ group and the rEPA4573-OPS$_{S/301}$ group, wherein the aluminium hydroxide group was used as negative control, and each of the other three groups was injected with 2.5 μg of polysaccharide as calculated based on the polysaccharide content of the conjugate vaccine as used. Each of the groups was immunized at Day 1, 14, 28, and eyeball was removed to collect blood 10 days after the last immunization.

Indirect ELISA was used to determine the titer of antibody against the *Shigella flexneri* 2a type O-antigen polysaccharide in the serum of each group of mice. The assay plates were coated with the extracted LPS of the *Shigella flexneri* 2a 301 strain, and each well was coated with 10 μg LPS. As to the other operating steps, please refer to Short Protocols in Molecular Biology [M]. Science Press, 2008.

Figure 9:
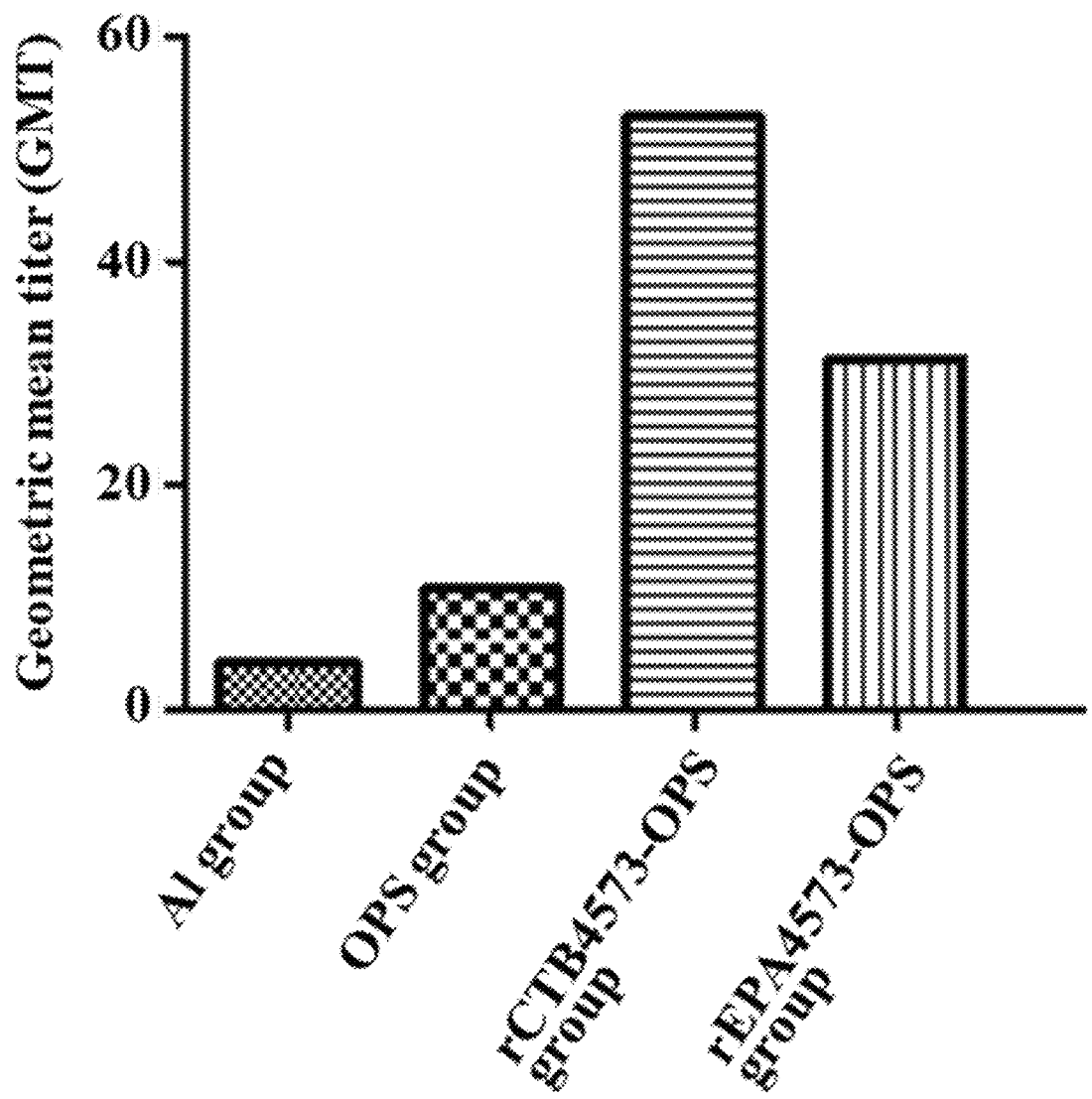

The results are shown in FIG. 9. In FIG. 9, A1 group represents the aluminium hydroxide group; OPS group represents the OPS$_{Sf301}$ group; rCTB-OPS group represents the rCTB4573-OPS$_{Sf301}$ group; rEPA4573-OPS group represents the rEPA4573-OPS$_{Sf301}$ group. FIG. 9 shows that as compared with OPS$_{Sf301}$, the rCTB4573-OPS$_{Sf301}$ purified in Step III and the rEPA4573-OPS$_{Sf301}$ purified in Step IV could significantly induce the generation of specific antibodies against OPS (O-polysaccharide) of *Shigella flexneri* 2a 301 in mice.

VI. Increasing the Ratio of Polysaccharides/Protein by Connection of O-Glycosylation Sites in Tandem (I) Construction of an Expression Vector of the Recombinant CTB Fusion Protein rCTB4573$_2$ Containing Two P1a Sequences In order to increase the percentage of polysaccharides in a glycoprotein, the amino acid sequences of two P1a (i.e., S45~K73 of PilE) were fused in tandem to the C-terminus of CTB, to synthesize rCTB4573$_2$.

The sequence encoding rCTB4573$_2$ is set forth in SEQ ID No.55, wherein starting from 5' end, the sequence from positions 64 to 372 is the CTB coding sequence, the sequence from positions 388 to 474, and the sequence from positions 487 to 573 each are the sequence encoding the amino acids from positions 45 to 67 of PilE, and the sequence from positions 7 to 63 is the sequence encoding DsbA signal peptide. The amino acid sequence of the protein rCTB4573$_2$ is set forth in SEQ ID No.56, wherein starting from N-terminus, the sequence from positions 20 to 122 is the CTB amino acid sequence, the sequence from positions 123 to 127, and the sequence from positions 157 to 160 is the flexible linker, the sequence from positions 128 to 156 and the sequence from positions 161 to 189 each are the amino acids from positions 45 to 73 of PilE, the sequence from positions 190 to 199 is the flexible linker and his-tag, and the sequence from positions 1 to 19 is the DsbA signal peptide sequence.

EcoRI and HindIII were used in double enzyme digestion of the DNA molecule set forth in SEQ ID No.55, to obtain a gene fragment; EcoRI and HindIII were used in double enzyme digestion of pMMB66EH, to obtain a large fragment; the gene fragment was ligated to the large fragment, to obtain the recombinant plasmid, designated as pMMB66EH-rCTB4573$_2$. The recombinant plasmid pMMB66EH-rCTB4573$_2$ was sequenced, and the results were correct.

(II) Construction of an Expression Vector of the Recombinant EPA Fusion Protein (rEPA4573$_{NMC}$) Containing Three P1a Sequences In order to increase the percentage of polysaccharides in a glycoprotein, according to the steric structure of EPA, three P1a sequences (i.e., S45~K73 of PilE) was introduced on the molecular surface. The particular method was as followed: two P1a polypeptides were fused at the N-terminus and C-terminus of rEPA, respectively; and one P1a polypeptide was fused between K240 and P241 of rEPA, so as to construct rEPA4573$_{NMC}$.

The sequence encoding rEPA4573$_{NMC}$ is set forth in SEQ ID No.57, wherein starting from 5' end, the sequence from positions 70 to 156, the sequence from positions 877 to 963, and the sequence from positions 2101 to 2187 each are the sequence encoding the amino acids from positions 45 to 67 of PilE, the sequence from positions 2188 to 2217 is the sequence encoding the flexible linker and his-tag, and the sequence from positions 7 to 63 is the sequence encoding DsbA signal peptide. The amino acid sequence of the protein rEPA4573$_{NMC}$ is set forth SEQ ID No.58. The sequence from positions 1 to 19 is the DsbA signal peptide; the sequence from positions 22 to 50, the sequence from positions 291 to 319, and the sequence from positions 699 to 727 each are the amino acids from positions 45 to 73 of PilE; the sequence from positions 694 to 698 is the flexible linker, and the sequence from positions 728 to 736 is the flexible linker and his-tag sequence.

EcoRI and HindIII were used in double enzyme digestion of the DNA molecule set forth in SEQ ID No. 57, to obtain a gene fragment; EcoRI and HindIII were used in double enzyme digestion of pMMB66EH, to obtain a large fragment; the gene fragment was ligated to the large fragment, to obtain the recombinant plasmid, designated as pMMB66EH-rEPA4573$_{NMC}$. The recombinant plasmid pMMB66EH-rEPA4573$_{NMC}$ was sequenced, and the results were correct.

(III) Preparation of Glycoengineered *Shigella flexneri*

In accordance with the method for preparing glycoengineered *Shigella flexneri* as disclosed in Step II (III), the glycoengineered bacteria *S. flexneri* 2a 301 ΔpCPΔwaaI/pETtac28-pglL/pMMB66EH-rCTB4573$_2$ and *S. flexneri* 2a 301 ΔpCPΔwaaI/pETtac28-pglL/pMMB66EH-rEPA4573$_{NMC}$ were constructed, respectively.

(IV) Glycosylation of rCTB4573$_2$ and rEPA4573$_{NMC}$ in the Glycoengineered *Shigella flexneri* and Identification Thereof The monoclonal colonies of glycoengineered bacteria *S. flexneri* 2a 301 ΔpCPΔwaaI/pETtac28-pglL/pMMB66EH-rCTB4573$_2$ and *S. flexneri* 2a 301 ΔpCPΔwaaI/pETtac28-pglL/pMMB66EH-rEPA4573$_{NMC}$, were seeded in LB medium containing ampicillin at a final concentration of 100 μg/mL and kanamycin at a final concentration of 50 μg/mL, respectively, and cultured at 37° C. When OD$_{600}$ was about 0.6, IPTG was added at a final concentration of 1 mM. The culture was cooled to 16° C. and induced for 20 h.

The next day, 1 mL bacterial liquid induced at 16° C. for 20 h, was centrifuged to extract bacteria, and the extracted bacteria were slowly suspended in 1× reducing buffer in a boiling water bath for 10 min, to obtain the sample for electrophoresis. The sample was then subjected to SDS-PAGE electrophoresis. After electrophoresis, the protein was transferred onto PVDF membrane by Bio-Lab Semi-Dry Blotter, at a constant voltage of 20V for 1 h, and detected by Anti-His tag mouse monoclonal antibody. The results are shown in FIG. 10.

Meanwhile, *S. flexneri* 2a 301 ΔpCPΔwaaI/pMMB66EH-rCTB4573$_2$, *S. flexneri* 2a 301 ΔpCPΔwaaI/pMMB66EH-rEPA4573$_{NMC}$, *S. flexneri* 2a 301 ΔpCPΔwaaI/pETtac28-pglL/pMMB66EH-rCTB4573, *S. flexneri* 2a 301 ΔpCPΔwaaI/pETtac28-pglL/pMMB66EH-rEPA4573, *S. flexneri* 2a 301 ΔpCPΔwaaI/pMMB66EH-rCTB4573, and *S. flexneri* 2a 301 ΔpCPΔwaaI/pMMB66EH-rEPA4573 were used as control.

Figure 10:
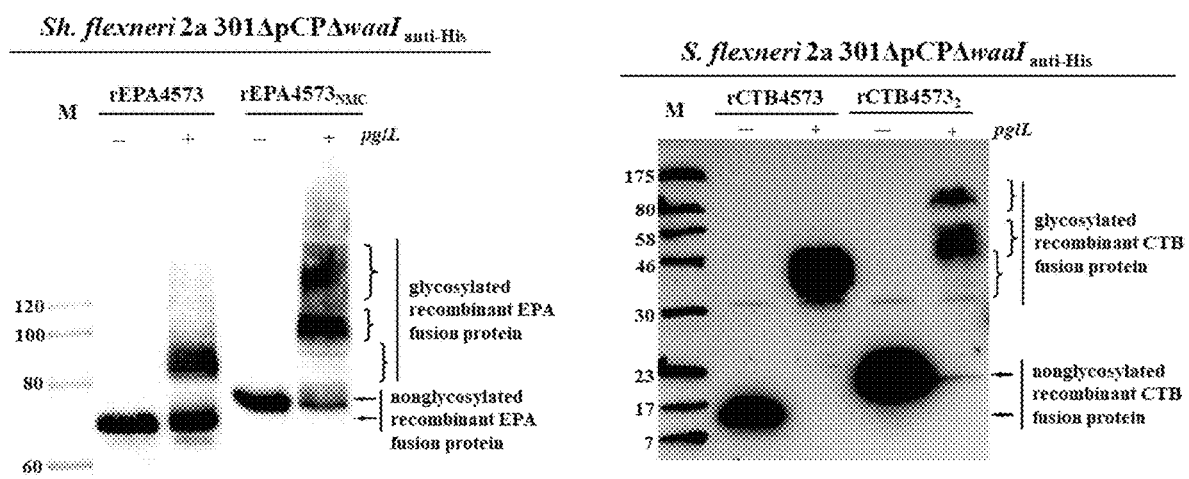
Figure 11:
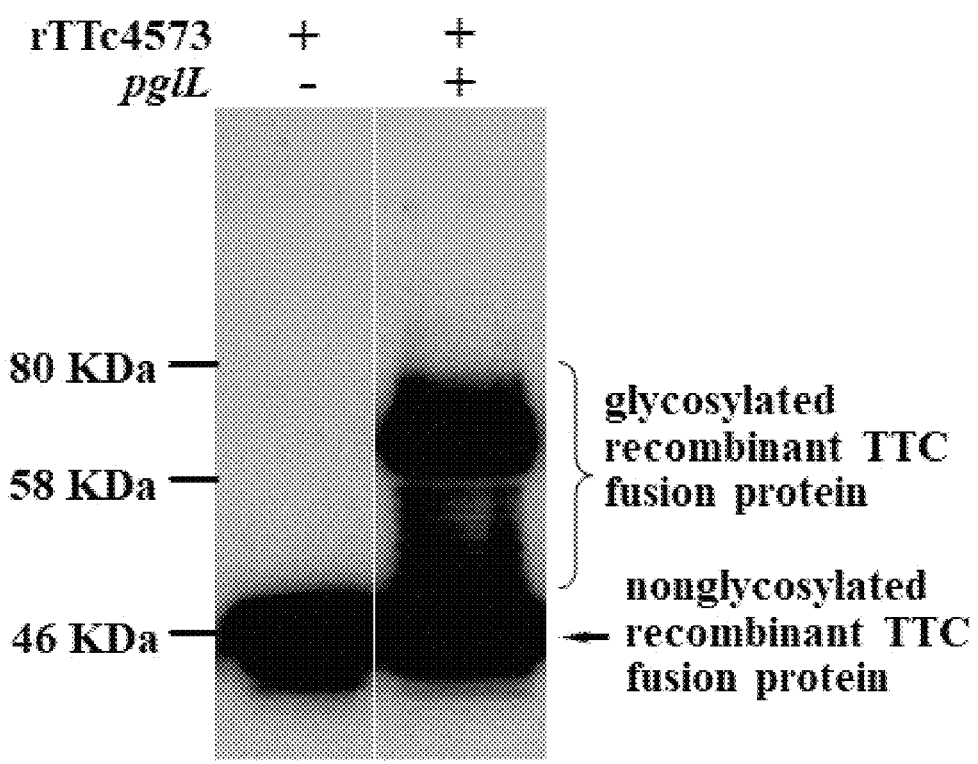
FIG. 11 shows the result of WB assay for the glycoprotein rTTC4573-OPS$_{Sf301}$.
Figure 12:
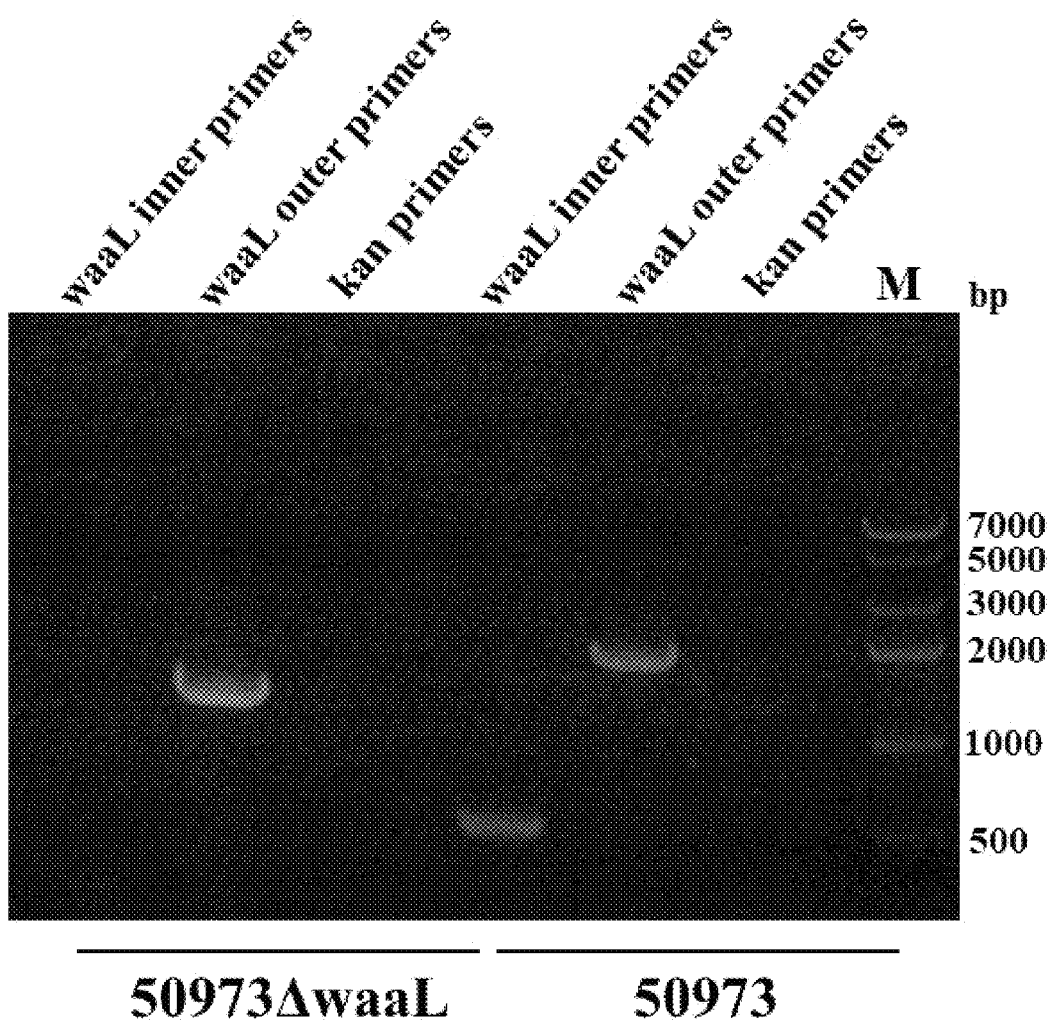
FIG. 12 shows the results of PCR identification of *S. paratyphi* CMCC50973ΔwaaL.

FIG. 10 shows that the recombinant fusion proteins rCTB4573, rEPA4573 expressed in the glycoengineered bacteria *S. flexneri* 2a 301 ΔpCPΔwaaI/pETtac28-pglL/pMMB66EH-rCTB4573$_2$ and *S. flexneri* 2a 301 ΔpCPΔwaaI/pETtac28-pglL/pMMB66EH-rEPA4573$_{NMC}$, were O-glycosylated, and after the introduction of multiple glycosylation sites, the appearance of several groups of glycosylated bands indicated that the proteins were effectively glycosylated at multiple sites.

VII. Preparation of Shigella flexneri O-Polysaccharide-Recombinant TTC Fusion Protein Conjugate by One-Step Bioconjugate Method (I) Construction of an Expression Vector of the TTC Fusion Protein According to the amino acid sequence of fragment C of tetanus toxin (AF154828.1) published on GenBank, DsbA signal peptide is fused to its N-terminus, the polypeptide of P1a (i.e., S45~K73 of PilE) and a 6×His tag were fused to its C-terminus, so as to construct the recombinant fragment C of tetanus toxin, rTTC4573.

The sequence encoding rTTC4573 is set forth in SEQ ID No.59, wherein starting from 5' end, the sequence from positions 64 to 1371 is the TTC coding sequence, the sequence from positions 1387 to 1473 is the sequence encoding the amino acids from positions 45 to 67 of PilE, and the sequence from positions 7 to 63 is the sequence encoding DsbA signal peptide.

The amino acid sequence of the protein rTTC4573 is set forth in SEQ ID No.60, wherein starting from N-terminus, the sequence from positions 20 to 455 is the TTC amino acid sequence, the sequence from positions 461 to 489 is the amino acids from positions 45 to 73 of PilE, the sequence from positions 490 to 498 is the flexible linker and his-tag, and the sequence from positions 1 to 19 is the DsbA signal peptide sequence.

EcoRI and HindIII were used in double enzyme digestion of the DNA molecule set forth in SEQ ID No.59, to obtain a gene fragment; EcoRI and HindIII were used in double enzyme digestion of pMMB66EH, to obtain a large fragment; and the gene fragment was ligated to the large fragment, to obtain the recombinant plasmid, designated as pMMB66EH-rTTC4573. The pMMB66EH-rTTC4573 was sequenced, and the result was correct.

(II) Preparation of Glycoengineered *Shigella flexneri*

*S. flexneri* 2a 301 ΔpCPΔwaaI/pETtac28-pglL was transformed with the pMMB66EH-rTTC4573, to construct the glycoengineered *Shigella flexneri, S. flexneri* 2a 301 ΔpCPΔwaaI/pETtac28-pglL/pMMB66EH-rTTC4573.

(III) Glycosylation of rTTC4573 in the Glycoengineered *Shigella flexneri and Identification Thereof*

The monoclonal colony of glycoengineered bacterium *S. flexneri* 2a 301 ΔpCPΔwaaI/pETtac28-pglL/pMMB66EH-rTTC4573 was seeded to LB medium containing 100 μg/mL ampicillin and 50 μg/mL kanamycin, and cultured at 37° C. When $OD_{600}$ was about 0.6, IPTG was added at a final concentration of 1 mM. The culture was cooled to 25° C. and induced for 20 h.

Meanwhile, *S. flexneri* 2a 301 ΔpCPΔwaaI/pMMB66EH-rTTC4573 was subjected to said induction experiment, as control.

The next day, 1 mL of the bacterial liquid induced at 25° C. for 20 h, was centrifuged to extract bacteria, and the extracted bacteria were slowly suspended in 1× reducing buffer, in a boiling water bath for 10 min, to obtain the sample for electrophoresis. The sample was then subjected to SDS-PAGE electrophoresis. After electrophoresis, the protein was transferred onto PVDF membrane by Bio-Lab Semi-Dry Blotter, at a constant voltage of 20V for 1 h, and detected Anti-His tag mouse monoclonal antibody. The results are shown in FIG. 11.

FIG. 11 shows that the substrate protein rTTC4573, in the presence of oligosaccharyltransferase PglL, was O-glycosylated.

Example 2. Preparation of *Salmonella paratyphi* A O-Polysaccharide-Recombinant CTB Fusion Protein by One-Step Bioconjugate Method I. Preparation of O-Antigen Ligase Gene waaL-Defective *Salmonella paratyphi* A (I) Preparation of linear targeting DNA fragment 1. Design and Synthesis of PCR Primers According to the waaL gene (GenBank number of CP000026, from positions 3696236 to 3697450) listed in the complete genomic sequence (NC_006511) of *Salmonella paratyphi* A 50973 strain (*S. paratyphi* CMCC50973) on NCBI, as well as upstream and downstream sequences thereof, a pair of primers, i.e., 73waaLu1/73waaLu2 and 73waaId1/73waaLd2, were designed for each of the upstream (5'end) and the downstream (3'end) of *Salmonella paratyphi* A 50973 waaI gene. For the convenience of operation, the BamHI and SalI restriction enzyme cleavage sites were added to the end of the primer for the upstream homologous arm "up", and the HindIII and XhoI restriction enzyme cleavage sites were added to the end of the primer for the downstream homologous arm "down".

In addition, in order to confirm whether the mutant was constructed successfully, a pair of primers (73waaLw1/73waaLw2) located outside the regions of the upstream and downstream homologous arms of waaI gene in the genome, a pair of internal primers for identification (73waaLn1/73waaLn2) and a pair of primers for kan gene (Kan1/Kan2) were designed to carry out PCR verification, and sequencing verification.

The primes are shown in Table 2 (in Table 2, the underlined sequences refer to the enzyme recognition sites).

TABLE 2

Primer sequence listing 2

| Primer | Sequence (5' → 3') | Use |
|---|---|---|
| 73waaLu1 | CG<u>GGATCC</u>AGGCTTTGACTATG TGGA (SEQ ID No. 61) | for amplification of up fragment |
| 73waaLu2 | GC<u>GTCGAC</u>ATCTGGCGATATGA GTATG (SEQ ID No. 62) | |
| 73waaLd1 | CC<u>AAGCTT</u>TAGTGCAGGCATAT TGGG (SEQ ID No. 63) | for amplification of down fragment |
| 73waaLd2 | CC<u>CTCGAG</u>TATCACCTCGCAGA ACCT (SEQ ID No. 64) | |
| 73waaLw1 | AACACCGGATTACGGATAA (SEQ ID No. 65) | for identification of the mutant strain |
| 73waaLw2 | TGCATGGTGGCTGTAGAA (SEQ ID No. 66) | |
| 73waaLn1 | AGAAACGGTTGCGAAAAT (SEQ ID No. 67) | for identification of the mutant strain |
| 73waaLn2 | ATAGCCGTAGCCCTTGAT (SEQ ID No. 68) | |
| Kan1 | GCGTCGACGTGTAGGCTGGAGC TGCTTC (SEQ ID No. 69) | for identification of the mutant strain |
| Kan2 | CCAAGCTTATGGGAATTAGCCA TGGTCC (SEQ ID No. 70) | |

2. Construction of Linear Targeting DNA Fragments

1) The genomic DNA of *Salmonella paratyphi* A 50973 strain was used as template, and 73waaLu1/73waaLu2 and 73waaLd1/73waaLd2 were used to amplify the upstream and downstream homologous arms of waaL gene, i.e., up and down, respectively.

PCR program was as followed: 94° C. 10 min; 94° C. 30 s, 50° C. 30 s, 72° C. 30 s, 30 cycles; 72° C. 10 min.

2) Construction of pETKan was performed as disclosed in Example 1.

3) BamHI and SalI were used in double enzyme digestion of the up fragment, to obtain the gene fragment 3; BamHI and SalI were used in double enzyme digestion of the plasmid pETKan, to obtain the large fragment 3; and the gene fragment 3 was ligated to the large fragment 3, to obtain the intermediate vector 3;

HindIII and XhoI were used in double enzyme digestion of the down fragment, to obtain the gene fragment 4; HindIII and XhoI were used in double enzyme digestion of the intermediate vector 3, to obtain the large fragment 4; and the gene fragment 4 was ligated to the large fragment 4, to obtain the intermediate vector 4.

4) BamHI and XhoI were used in double enzyme digestion of the intermediate vector 4, to obtain the targeting DNA fragment of interest, flanked by the homologous arms, and having the kan gene in the middle region. The nucleotide sequence of the fragment is set forth in SEQ ID No.71.

In SEQ ID No.71, starting from 5' end, the nucleotides from positions 7 to 571 refer to the up fragment, the nucleotides from positions 578 to 2073 refer to the kan gene, and the nucleotides from positions 2080 to 2543 refer to the down fragment.

The DNA fragment set forth in SEQ ID No.71 was used as template, and 73waaLu1 and 73waaLd2 were used as primers, to further amplify the targeting fragment by PCR, to obtain the linear targeting DNA fragment at a concentration of up to 300 ng/μL.

(II) Construction of *S. paratyphi* CMCC50973/pKOBEG

Since the plasmid pKOBEG comprised the genes encoding the enzymes necessary for λ-Red recombination system, the plasmid pKOBEG was transformed into *Salmonella paratyphi* A 50973 competent cells by electroporation, and the transformed cells were spread onto LB-plate containing chloramphenicol (the plasmid pKOBEG is chloramphenicol-resistant), and cultured at 30° C. overnight, to obtain the positive clone, designated as *S. paratyphi* 50973/pKOBEG strain.

(III) Transformation of *S. paratyphi* 50973/pKOBEG with the linear targeting DNA fragments by electroporation 1. The *S. paratyphi* CMCC50973/pKOBEG was seeded to low salt LB liquid medium containing chloramphenicol at a final concentration of 30 μg/mL, cultured at 30° C. overnight, and then passaged in low salt LB liquid medium at a volume ratio of 1:100 for future culture.

2. L-arabinose was added at a final concentration of 1 mmol/L to induce the expression of Red recombination system at 1 h before the $OD_{600}$ value of the culture medium in Step 1 reached 0.6.

3. When the $OD_{600}$ of the culture medium in Step 2 reached 0.6, the *S. paratyphi* CMCC50973/pKOBEG was transformed with 5 μL the targeting DNA fragments as prepared in Step (I) at 300 ng/μL by electroporation.

4. To the transformed cells, 1 mL precooled low salt LB liquid medium was added. The cells were thawed at 30° C. for about 2.5 h, and then were spread onto a LB plate containing kanamycin at a concentration of 50 μg/mL, and cultured in a 30° C. incubator overnight; and the positive clone was screened out.

5. The positive clone was seeded to LB liquid medium containing kanamycin at a concentration of 50 μg/mL, and cultured at 42° C. and passaged twice (12 h for each passage), thereby resulting in the deletion of the plasmid pKOBEG. The kanamycin-resistant, waaI-deleted mutant strain was obtained finally, designated as *S. paratyphi* CMCC50973 waaL::kan.

(IV) The plasmid pCP20 encoding a FRT site-specific recombinase was transformed into *S. paratyphi* CMCC50973 waaL::kan by electroporation, and cultured in kanamycin-free LB plate containing chloramphenicol at a concentration of 50 μg/mL at 30° C. The positive clone of $Cm^rKm^s$(chloramphenicol-resistant, kanamycin-sensitive) was screened.

(V) The positive clone screened in Step (IV), was transferred to liquid LB, and cultured at 42° C. for 12 h, to obtain the target gene-deleted mutant free of the kanamycin resistance gene and the plasmid pCP20, designated as *S. paratyphi* CMCC50973ΔwaaL, i.e., lipopolysaccharide synthesis-deficient *Salmonella paratyphi* A.

II. Molecular Identification of *S. paratyphi* CMCC50973ΔwaaL

The genomic DNA of *S. paratyphi* CMCC50973 and *S. paratyphi* CMCC50973ΔwaaL were used as template, respectively, and a pair of waaL inner primers (73waaLn1/73waaLn2), a pair of waaL outer primers (73waaLw1/73waaLw2) and a pair of kan primers (kan1/kan2) were used to carry out PCR verification, respectively.

The results are shown in FIG. 12. In FIG. 12, 50973ΔwaaL represents *S. paratyphi* CMCC50973ΔwaaL; and 50973 represents *S. paratyphi* CMCC50973. FIG. 12 shows that when the genomic DNA of *S. paratyphi* CMCC50973ΔwaaL was used as template, and the waaL inner primers were used as primers to carry out PCR amplification, no target bands appeared; when the genomic DNA of *S. paratyphi* CMCC50973 was used as template, and the waaL inner primers were used as primers to carry out PCR amplification, target bands appeared. Moreover, since *S. paratyphi* CMCC50973ΔwaaL had the waaL gene knocked out, the band, obtained when the genomic DNA of *S. paratyphi* CMCC50973ΔwaaL was used as template, and the waaL outer primers were used as primers to carry out PCR amplification, is smaller than the band, obtained when the genomic DNA of *S. paratyphi* CMCC50973 was used as template, and the waaL outer primers were used as primers to carry out PCR amplification. Since the Kan resistance gene was finally deleted, when the genomic DNA of *S. paratyphi* CMCC50973ΔwaaL was used as template, and the kan primers were used as primers to carry out PCR amplification, no target bands appeared.

The above results demonstrate the successful construction of a waaL gene-deleted *Salmonella paratyphi* A 50973 mutant with no antibiotic resistance gene, i.e. *S. paratyphi* CMCC50973ΔwaaL.

III. Phenotype Identification of *S. paratyphi* CMCC50973ΔwaaL 1 mL culture of *S. paratyphi* CMCC50973ΔwaaL cultured at 37° C. overnight, was centrifuged to collect bacteria. The bacteria were washed with PBS once, and 100 μL lysis buffer (the lysis buffer was prepared by well mixing 2 mL 10% SDS, 0.4 mL 2-mercaptoethanol, 1 mL 100% glycerol, 5 mL 2M pH6.8 Tris-HCl, 20 μL 10% bromophenol blue and 1.6 mL $ddH_2O$) was added and mixed well. After heating in boiling water for 10 min, 4 μL of 20 mg/mL protease K aqueous solution was added, and the reaction was carried out at 60° C. for 1-2 h, to obtain lysates. 15 μl of the lysates was loaded to carry out SDS-PAGE electrophoresis, the gel was placed in the fixing solution overnight, and a sensitizing solution was added and reacted for 30 min. After washing with deionized water for three times, 15 min for each time, a silver nitrate solution was added and reacted for 20 min, and deionized water was used for washing twice, 1 min for each time. A developing solution was added for color development, the reaction was stopped finally, and deionized water was used for washing.

*S. paratyphi* CMCC50973 was also subjected to the above experiment, as control.

Figure 13:
FIG. 13 shows the verification result of lipopolysaccharide synthesis deficiency in *S. paratyphi* CMCC50973ΔwaaL by silver staining.
Figure 14:
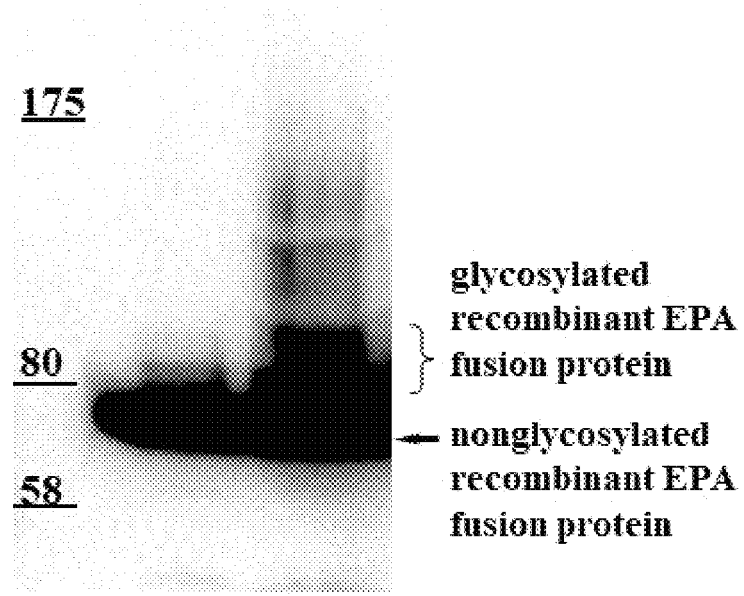
FIG. 14 shows the result of WB assay for glycoprotein rEPA4573-OPS$_{Spty50973}$.
Figure 15:
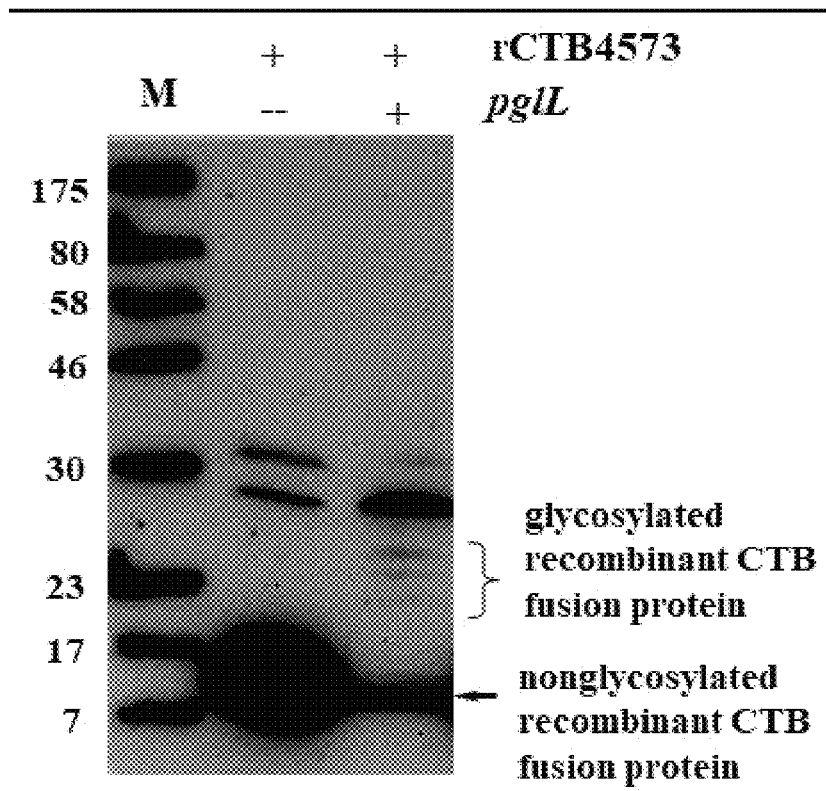
FIG. 15 shows the result of WB assay for the glycoprotein rCTB4573-OPS$_{Spty50973}$.

The results are shown in FIG. 13. In FIG. 13, 50973ΔwaaL represents *S. paratyphi* CMCC50973ΔwaaL; and 50973 represents *S. paratyphi* CMCC50973. FIG. 13 shows that the wild-type strain *S. paratyphi* CMCC50973 had ladder-like bands, while the mutant strain had no ladder-like bands due to the knockout of O-antigen ligase gene waaL (waaL functions to ligate O-antigen polysaccharide (OPS) to lipoid A-core oligosaccharide to form lipopolysaccharide(LPS)).

IV. Preparation of *Salmonella paratyphi* A O-Polysaccharide-Recombinant EPA Fusion Protein Conjugate by One-Step Bioconjugate Method (I) Construction of Glycoengineered *Salmonella paratyphi* A, *S. paratyphi* CMCC50973ΔwaaL/pETtac28-pglL/pMMB66EH-rEPA4573

The host bacterium *S. paratyphi* CMCC50973ΔwaaL was transformed with the vectors pETtac28-pglL and pMMB66EH-rEPA4573 sequentially by electroporation, and the transformed cells were spread onto LB solid medium containing kanamycin at a final concentration of 50 μg/mL and ampicillin a final concentration of 100 μg/mL, and the clone formed was the glycoengineered *Salmonella paratyphi* A, *S. paratyphi* CMCC50973ΔwaaL/pETtac28-pglL/pMMB66EH-rEPA4573.

(II) Glycosylation of the EPA Fusion Protein and Identification Thereof

The monoclonal colony of glycoengineered bacterium *S. paratyphi* CMCC509730waaL/pETtac28-pglL/pMMB66EH-rEPA4573, was seeded in LB medium containing ampicillin at a final concentration of 100 μg/mL and kanamycin at a final concentration of 50 μg/mL, and cultured at 37° C. When $OD_{600}$ was about 0.6, IPTG was added at a final concentration of 1 mM. The culture was cooled to 25° C. and induced for 20 h, to obtain the glycoprotein rEPA-$OPS_{Spty50973}$.

The next day, 1 mL of the bacterial liquid induced at 25° C. for 20 h, was centrifuged to extract bacteria, and the extracted bacteria were slowly suspended in 1× reducing buffer, in a boiling water bath for 10 min, to obtain the sample for electrophoresis. The sample was then subjected to 8% SDS-PAGE electrophoresis. After electrophoresis, the protein was transferred onto PVDF membrane by Bio-Lab Semi-Dry Blotter, at a constant voltage of 20V for 1 h, and was subjected to western-blot detection using anti-EPA antibody.

Meanwhile, the *S. paratyphi* CMCC50973ΔwaaL/pMMB66EH-rEPA4573, constructed by transforming *S. paratyphi* CMCC50973ΔwaaL with pMMB66EH-rEPA4573 but not with pETtac28-pglL, was used as control, to carry out the above induction experiment.

The results are shown in FIG. 14. FIG. 14 shows that the substrate protein rEPA4573, in the presence of oligosaccharyltransferase PglL, was O-glycosylated.

V. Preparation of *Salmonella paratyphi* A O-Polysaccharide-Recombinant CTB Fusion Protein Conjugate by One-Step Bioconjugate Method (I) Construction of Glycoengineered *Salmonella paratyphi* A, *S. paratyphi* CMCC50973ΔwaaL/pETtac28-pglL/pMMB66EH-rCTB4573

The host bacterium *S. paratyphi* CMCC50973ΔwaaL was transformed with the vectors pETtac28-pglL and pMMB66EH-rCTB4573 sequentially, and spread onto LB solid medium containing kanamycin at a final concentration of 50 μg/mL and ampicillin at a final concentration of 100 μg/mL, and the clone formed was the glycoengineered *Salmonella paratyphi* A, *S. paratyphi* CMCC50973ΔwaaL/pETtac28-pglL/pMMB66EH-rCTB4573.

(II) Glycosylation of the Recombinant CTB Fusion Protein and Identification Thereof The monoclonal colony of glycoengineered bacterium *S. paratyphi* CMCC50973ΔwaaL/pETtac28-pglL/pMMB66EH-rCTB4573, was seeded in LB medium containing ampicillin at a final concentration of 100 μg/mL and kanamycin at a final concentration of 50 μg/mL, and cultured at 37° C. When $OD_{600}$ was about 0.6, IPTG was added at a final concentration of 1 mM. The culture was cooled to 16° C. and induced for 20 h, to obtain the glycoprotein CTB-$OPS_{Spty50973}$.

The next day, 1 mL of the bacterial liquid induced at 16° C. for 20 h, was centrifuged to extract bacteria, and the extracted bacteria wee slowly suspended in 1× reducing buffer, in a boiling water bath for 10 min, to obtain the sample for electrophoresis. The sample was then subjected to 8% SDS-PAGE electrophoresis. After electrophoresis, the protein was transferred onto PVDF membrane by Bio-Lab Semi-Dry Blotter, at a constant voltage of 20V for 1 h, and subjected to western-blot detection using Anti-His tag mouse monoclonal antibody.

The *S. paratyphi* CMCC50973ΔwaaL/pMMB66EH-rCTB4573, constructed by transforming *S. paratyphi* CMCC50973ΔwaaL with pMMB66EH-rCTB4573 but not with pETtac28-pglL, was used as control, to carry out the induction experiment.

The results are shown in FIG. 15. FIG. 15 shows that the substrate protein rCTB4573, in the presence of O-oligosaccharyltransferase PglL, was O-glycosylated.

Example 3. Modification of the Recombinant CTB Fusion Protein with Exogenous O-Polysaccharides of *E. coli* O157

When a recombinant fusion protein is modified by an exogenous polysaccharide, it needs a bacterium defective in both O-antigen ligase gene and host O-antigen synthesis, as a host. When O-antigen ligase gene is deleted, no matter the polysaccharides expressed in the host bacterium are endogenous or exogenous, they cannot be utilized in LPS synthesis pathway in the host, while the O-antigen synthesis deficiency in the host ensures that the glycosylation system only utilizes exogenous polysaccharides to modify the recombinant fusion protein, thereby avoiding the contamination due to the modification of the recombinant fusion protein with the endogenous O-antigen polysaccharides in the host. In a host bacterium, a recombinant fusion protein gene, *Neisseria meningitidis* O-oligosaccharyltransferase PglL gene, a gene cluster for synthesis of exogenous polysaccharide, are co-expressed in the host bacterium; and in the presence of O-oligosaccharyltransferase PglL as catalyst, the exogenous polysaccharide is transferred to the recombinant fusion protein.

In the Example, *E. coli* K12 W3110 strain is used as host bacterium; for naturally occurring insertional inactivation of the wbbL gene of the key glycosyltransferase, rhamnosyl transferase, in the O-antigen synthesis pathway in K12 strain, endogenous O-antigen cannot be synthesized; therefore only the O-antigen ligase gene waaL needs to be knocked out to construct a host bacterium defective in both O-antigen ligase and O-antigen synthesis.

I. Construction of a host bacterium defective in both O-antigen ligase and O-antigen synthesis
  (I) Preparation of Linear Targeting DNA Fragments
    1. Design and Synthesis of PCR Primers
    According to the genomic sequence (AC_000091.1) of the *E. coli* W3110 strain published on GenBank, the targeting fragment for the waaL gene (from positions 3696236 to 3697450) was designed. Two fragments of 41 bp were selected from the upstream and downstream of the waaL gene, respectively, and used as the homologous arms, and 3' end of each homologous arm was linked with one of the primers for amplification of chloramphenicol-resistant gene flanked by FRT sites, thereby obtaining the chloramphenicol-resistant gene fragment flanked by the 41 bp upstream and downstream homologous arms of the waaL gene and FRT sites, by PCR amplification; and the primers 3110waaL up 5' and 3110waaL down 3' located outside the waaL gene region were designed to identify whether the waaL gene was knocked out or not.
    The primers are shown in Table 3.

TABLE 3

Primer sequence listing 3

| Primer name | Primer sequence (5'→3') | Note | Use of the primer pair |
|---|---|---|---|
| 3110waaLcat 5' | GCAGTTTTGGAAAAGTTATCATC ATTATAAAGGTAAAACATAGCGA TTGTGTAGGCTGGAG (SEQ ID No. 72) | the waaL homologous arms were underlined | For amplification of chloramphenicol-resistant gene fragment comprising upstream and downstream homologous arms of the waaL gene |
| 3110waaLcat 3' | AGTGAGTTTTAACTCACTTCTTA AACTTGTTTATTCTTAATAATTA ACGGCTGACATGGGAATTAG (SEQ ID No. 73) | | |
| 3110waaL up 5' | TACAAATAGTATCCCCAAC (SEQ ID No. 74) | — | primers for identifying waaL knock-out |
| 3110waaL down 3' | AATTAACCTCAACAGTCAA (SEQ ID No. 75) | | |

2. Construction of Linear Targeting DNA Fragments
  The plasmid pKD3 was used as a template, and 3110waaLcat 5' and 3110waaLcat 3' were used as primers to carry out PCR amplification, to obtain the chloramphenicol-resistant gene fragment flanked by the 41 bp upstream and downstream homologous arms of the waaL gene and FRT sites. The fragment was set forth in SEQ ID No.76.
  (II) Obtainment of O-Antigen Ligase Gene waaL-Defective *E. coli* W3110 (*E. coli* W3110ΔwaaL)
    1. Preparation of *E. coli* W3110/pKD46
    1) *E. coli* W3110 was seeded in LB liquid medium, after incubating at 37° C. overnight, the culture was transferred to 100 mL LB liquid medium at a volume ratio of 1:100, and cultured at 37° C. until $OD_{600}$ reached 0.6.
    2) The bacteria were collected by centrifugation, and washed with the autoclaved 10% glycerol (v/v) for four times, and finally re-suspended in 400 μL 10% glycerol, to obtain *E. coli* W3110 competent cells for use in electrotransformation, sub-packaged for later use.
    3) The plasmid pKD46 (the replicon of pKD46 is sensitive to temperature, and lost when cultured at 37° C., and the plasmid comprises the genes encoding three recombinases of Red recombination system and controlled by arabinose promoter) was transformed into the prepared *E. coli* W3110 competent cell by electroporation, and the transformed cells were spread onto the LB plate containing ampicillin at a final concentration of 100 μg/mL. After culturing at 30° C. overnight, the obtained positive clone was the *E. coli* W3110/pKD46 strain.

2. Preparation of *E. coli* W3110 waaL::cat
    1) The *E. coli* W3110/pKD46 was cultured at 30° C. overnight, and then passaged in LB liquid medium containing 100 μg/mL ampicillin at a volume ratio of 1:100 for future culture.
    2) When the $OD_{600}$ value was about 0.2, L-arabinose was added at a final concentration of 0.2 g/100 ml to induce the expression of Red recombination system; when the $OD_{600}$ value was about 0.6, the *E. coli* W3110/pKD46 competent cell was prepared.
    3) 10 μL of the linear targeting DNA fragments prepared in the step (I) was transformed into the *E. coli* W3110/pKD46 competent cell by electroporation.
    4) 1 mL precooled low salt LB liquid medium was added quickly. The cells were thawed at 30° C. for about 2.5 h, and then were spread onto a LB plate containing chloramphenicol at a concentration of 30 μg/mL, and cultured in a 30° C. incubator overnight.
    5) The positive clone was screened out. Its genomic DNA was extracted and used as template, and 3110waaL up 5' and 3110waaL down 3' were used as primers to carry out PCR identification, to obtain PCR amplification product. Meanwhile, the genomic DNA of *E. coli* W3110 was used as template, to carry out the PCR amplification, as control.
    The PCR amplification product of *E. coli* W3110 was of 1444 bp, while the PCR amplification product of the positive clone in Step 5) was of 1246 bp when the waaL gene was replaced with the cat gene, the positive clone was designated as *E. coli* W3110 waaL::cat/pKD46.
    6) the *E. coli* W3110 waaL::cat/pKD46 was seeded in LB liquid medium containing chloramphenicol at a final concentration of 30 μg/mL, and passaged for three times at 37° C. (culturing for 12 h for each passage), resulting in the deletion of the plasmid pKD46, to obtain *E. coli* W3110 waaL::cat strain.
  3. Obtainment of *E. coli* W3110 ΔwaaL Strain
    1) The pCP20 was transformed into *E. coli* W3110 waaL::cat cell by electroporation, and the transformed cells were spread onto LB plate containing 100 μg/mL ampicillin, to obtain W3110 waaL::cat/pCP20 strain.
    2) The monoclonal colony of *E. coli* W3110 waaL::cat/pCP20 was seeded in LB liquid medium, cultured at 30° C. until $OD_{600}$ was about 0.6, and then cultured at 42° C. overnight.
    (the replicon of pCP20 is sensitive to temperature, and lost when cultured at 42° C., the plasmid comprises the DNA encoding FLP recombinase, controlled by temperature-sensitive promoter, and the expression of FLP recombinase was induced when cultured at 42° C., with the loss of the plasmid.)

3) The monoclonal colony was isolated by streak plate method from the bacterial liquid cultured at 42° C. overnight on LB plate, and the colonies were grown on LB plate with or without chloramphenicol. The colonies, which grew on LB plate but not on LB plate containing chloramphenicol, were picked and designated as E. coli W3110ΔwaaL. Its genomic DNA was used as template, and 3110waaL up 5' and 3110waaL down 3' were used as primers to carry out PCR identification, to obtain the PCR amplification product. The genomic DNA of E. coli W3110 and E. coli W3110 waaL::cat were separately used as template, to carry out the PCR amplification, as control.

Figure 16:
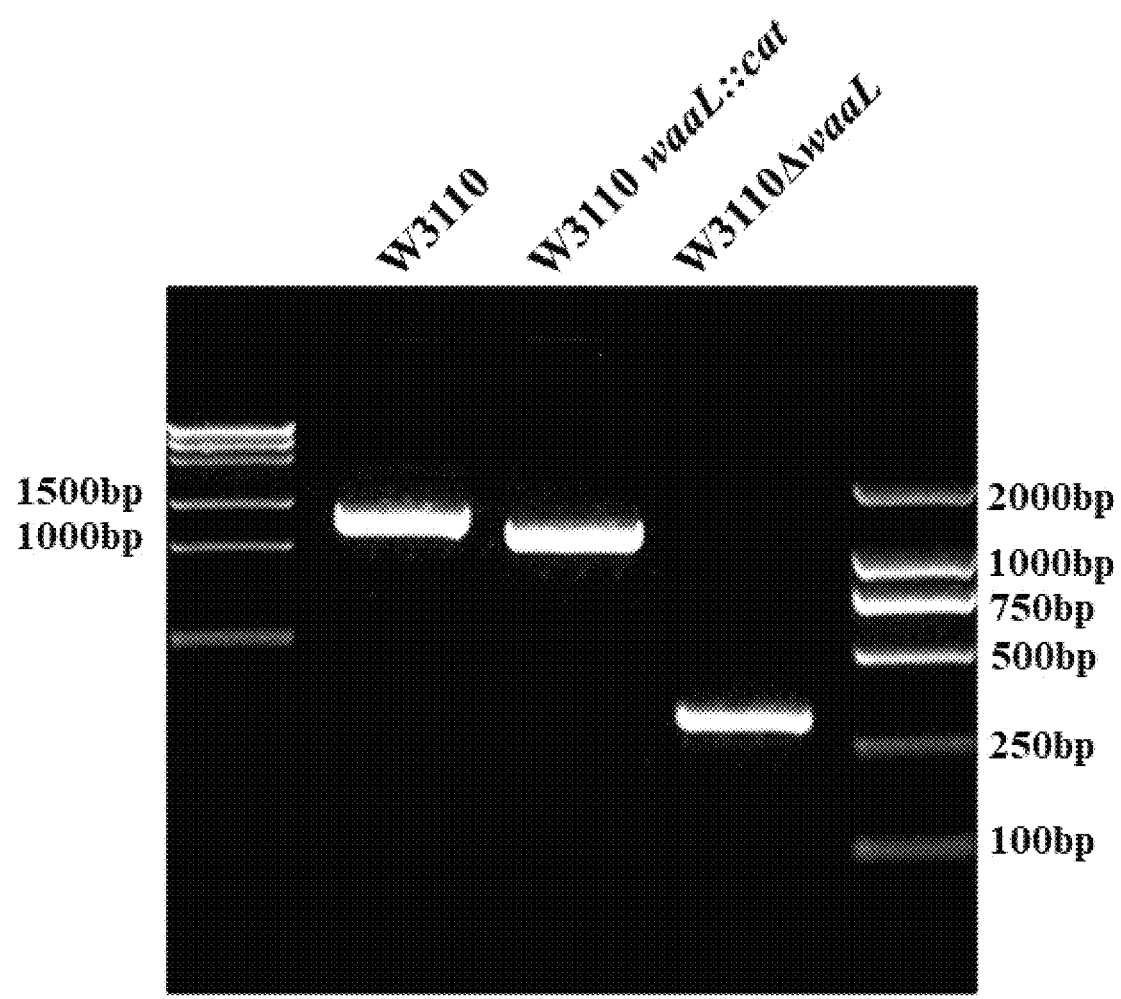
FIG. 16 shows the result of PCR identification of *E. coli* W3110ΔwaaL.

The results are shown in FIG. 16. The PCR amplification fragment of E. coli W3110 was of 1444 bp, and the PCR amplification fragment of W3110 waaL::cat resulted from the replacement of the waaL gene with the cat gene was of 1246 bp, and the PCR amplification fragment of E. coli W3110ΔwaaL with the cat gene deleted, was of 316 bp. FIG. 16 shows the successful construction of E. coli W3110ΔwaaL.

II. The construction of the recombinant CTB fusion protein expression vector pMMB66EH-rCTB4573 was performed as disclosed in Step II (III) in Example 1.

III. Construction of Neisseria meningitidis O-oligosaccharyltransferase PglL expression vector pETtac28-pglL was performed as disclosed in Step II (I) in Example 1.

IV. Construction of expression vector pACYC184-O157 comprising a gene cluster for synthesis of the exogenous bacterial polysaccharide (I) According to the gene sequence of O157 (GeBank: AF061251.1) on NCBI website, the following primers were designed:

```
O157-5' (the underlined sequence is the AscI
enzyme recognition site):
                                    (SEQ ID No. 77)
5'-AGAAGGCGCGCCAAGAATGACGAATTTAAAAGCAGTTATACCG
GTAGCAGGT-3'

O157-3' (the underlined sequence is the NotI
enzyme recognition site):
                                    (SEQ ID No. 78)
5'-ATATGCGGCCGCTTAATCCACTCCATTCCTGTATGGAACACAC
CTTCTTT-3'
```

(II) The genomic DNA of E. coli O157 was used as template, and O157-5' and O157-3' were used as primers to carry out PCR amplification, to obtain PCR amplification product, i.e., the gene cluster for O157 polysaccharide synthesis, as set forth in SEQ ID No.79.

(III) According to the gene sequences of the plasmid pACYC184, the following primers were designed:

```
p184-5':
                                    (SEQ ID No. 80)
5'-ATATGGCGCGCCTCTGAGTTACAACAGTCCGC-3'
(the underlined sequence is the AscI enzyme
recognition site)

p184-3':
                                    (SEQ ID No. 81)
5'-ATAAGCGGCCGCTTCAGGTGCTACATTTGAAG-3'
(the underlined sequence is the NotI enzyme
recognition site)
```

(IV) pACYC184 was used as template, and p184-5' and p184-3' were used as primers to carry out PCR amplification, to obtain the PCR amplification product, i.e., the linear pACYC184 vector fragment, set forth in SEQ ID No.82.

(V) AscI and NotI were used in double enzyme digestion of the DNA molecule set forth in SEQ ID No.79, to obtain a gene fragment; AscI and NotI were used in double enzyme digestion of the DNA molecule set forth in SEQ ID No.82, to obtain a large fragment; the gene fragment was ligated to the large fragment, to obtain the recombinant plasmid, designated as pACYC184-O157. The pACYC184-O157 was sequenced, and the result was correct.

V. Construction of Glycoengineered E. coli

The three recombinant plasmids pMMB66EH-rCTB4573, pETtac28-pglL and pACYC184-O157 were transformed into the host bacterium E. coli W3110ΔwaaL by electroporation, and the transformed cells were spread onto LB plate containing ampicillin, kanamycin and chloramphenicol, and the formed clone was the glycoengineered E. coli, E. coli W3110ΔwaaL/pMMB66EH-rCTB4573/pETtac28-pglL/pACYC184-O157.

VI. Glycosylation of the Recombinant CTB Fusion Protein r CTB4573-OPS$_{EcO157}$ and Identification Thereof The monoclonal colony of glycoengineered bacterium E. coli W3110ΔwaaL/pMMB66EH-rCTB4573/pETtac28-pglL/pACYC184-O157, was seeded to LB medium containing 100 μg/mL ampicillin, 50 μg/mL kanamycin and 30 μg/mL chloramphenicol, and cultured at 37° C. When OD$_{600}$ was about 0.6, IPTG was added at a final concentration of 1 mM. The culture was cooled to 16° C. and induced for 20 h, to express rCTB4573-OPS$_{EcO157}$.

1 mL of the bacterial liquid induced at 16° C. for 20 h, was centrifuged to extract bacteria, and the the extracted bacteria were slowly suspended in 1× reducing buffer, in a boiling water bath for 10 min, to obtain the sample for electrophoresis. The sample was then subjected to 15% SDS-PAGE electrophoresis. After electrophoresis, the protein was transferred onto PVDF membrane by Bio-Lab Semi-Dry Blotter, at a constant voltage of 20V for 1 h, and detected by rabbit anti-E. coli O157 antiserum.

E. coli W3110ΔwaaL/pMMB66EH-rCTB4573/pETtac28-pglL was used as control.

Figure 17:
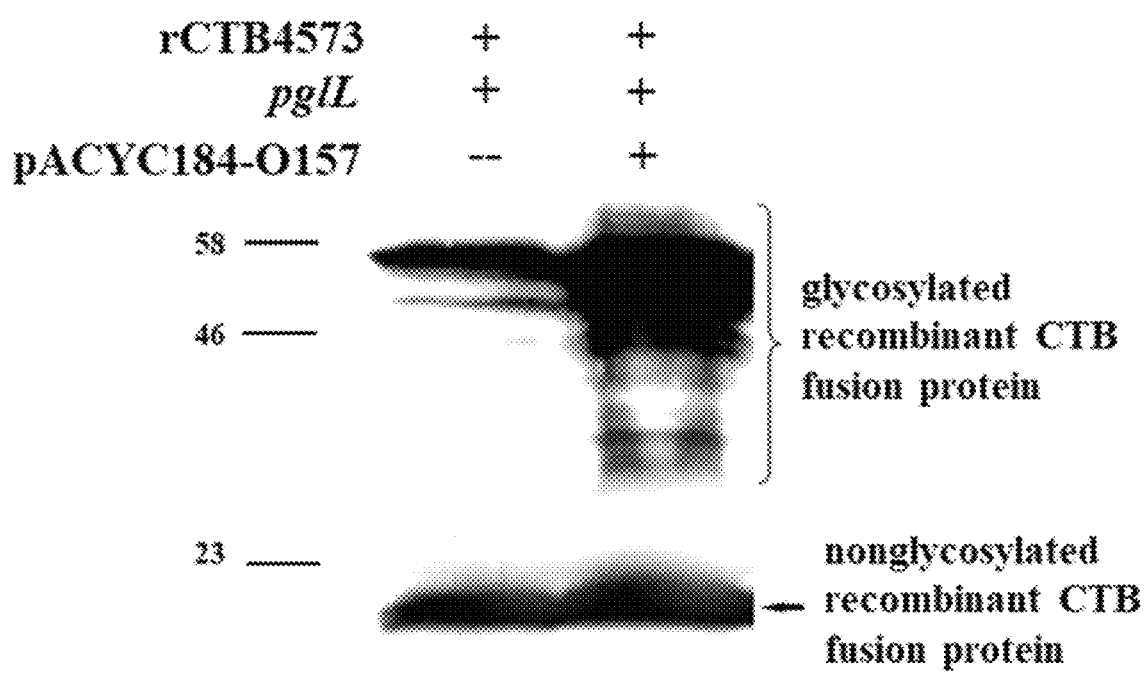
FIG. 17 shows the result of WB assay for the glycoprotein rCTB4573-OPS$_{EcO157}$.

The results are shown in FIG. 17. FIG. 17 shows that the substrate protein rCTB4573, in the presence of oligosaccharyltransferase PglL and a gene cluster for synthesis of exogenous polysaccharide, was O-glycosylated.

INDUSTRIAL APPLICATION

As compared with the polysaccharide proteins prepared by the existing chemical crosslinking methods, the bacterial polysaccharide-modified recombinant fusion proteins prepared by the method of the invention have the advantages such as homogeneous polysaccharide binding sites, and controllable quality; and the preparation of bacterial polysaccharide-modified recombinant fusion proteins by culturing engineering bacteria, has the advantages such as high-efficient production, low production cost, and good biosafety, as it does not comprises the steps such as the preparation of polysaccharides, the preparation of carrier protein, and chemical crosslinking. Specific antibodies against bacterial polysaccharides can be obtained by immunizing a mouse with the bacterial polysaccharide-modified recombinant fusion protein prepared by the method of the invention. The use of the bacterial polysaccharide-modified recombinant fusion protein in the preparation of a bacterial polysaccharide-protein conjugate vaccine, can avoid a variety of problems concerning the culture of pathogenic bacteria, enhance the homogeneity of vaccines and production efficiency, and reduce the cost for vaccine preparation. The invention has a wide application prospect in the preparation of polysaccharide-modified protein vaccines.

What is claimed is:

1. A method for preparing a bacterial polysaccharide-modified recombinant fusion protein, comprising co-expressing a recombinant fusion protein and *Neisseria meningitidis* O-oligosaccharyltransferase PglL in a O-antigen ligase gene-defective bacterium, and linking a polysaccharide endogenous or exogenous for the bacterium to the recombinant fusion protein by the *Neisseria meningitidis* O-oligosaccharyltransferase PglL, to obtain the bacterial polysaccharide-modified recombinant fusion protein;

wherein the recombinant fusion protein comprises an N-terminal signal peptide, a peptide fragment having a glycosylation site of *Neisseria meningitidis* O-oligosaccharyltransferase PglL, and a carrier protein;

the carrier protein is a nontoxic mutant of a bacterial toxin protein or a fragment of a bacterial toxin protein;

the glycosylation site of *Neisseria meningitidis* O-oligosaccharyltransferase PglL is the serine at position 63 starting from N-terminus of *Neisseria meningitidis* pilin PilE; and, the peptide fragment having a glycosylation site of *Neisseria meningitidis* O-oligosaccharyltransferase PglL is a peptide fragment comprising at least the amino acids from positions 55 to 66 starting from N-terminus of *Neisseria meningitidis* pilin PilE, and is any one of the following peptide fragments:

(1) the peptide fragment set forth in the amino acid sequence from positions 128 to 156 starting from N-terminus of SEQ ID No.32 or a tandem repeat sequence thereof;

(2) the peptide fragment set forth in the amino acid sequence from positions 128 to 154 starting from N-terminus of SEQ ID No.34 or a tandem repeat sequence thereof;

(3) the peptide fragment set forth in the amino acid sequence from positions 128 to 152 starting from N-terminus of SEQ ID No.36 or a tandem repeat sequence thereof;

(4) the peptide fragment set forth in the amino acid sequence from positions 128 to 150 starting from N-terminus of SEQ ID No.38 or a tandem repeat sequence thereof;

(6) the peptide fragment set forth in the amino acid sequence from positions 22 to 40 starting from N-terminus of SEQ ID No.48 or a tandem repeat sequence thereof; and (7) the peptide fragment set forth in the amino acid sequence from positions 22 to 36 starting from N-terminus of SEQ ID No.50 or a tandem repeat sequence thereof.

2. The method according to claim 1, characterized in that the nontoxic mutant of the bacterial toxin protein is a nontoxic mutant of *Pseudomonas aeruginosa* exotoxin A; the nontoxic mutant of *Pseudomonas aeruginosa* exotoxin A is set forth in the amino acid sequence from positions 20 to 631 starting from N-terminus of SEQ ID No.46.

3. The method according to claim 1, characterized in that the fragment of the bacterial toxin protein is cholera toxin B subunit or fragment C of tetanus toxin; wherein the amino acid sequence of the cholera toxin B subunit is set forth in the amino acid sequence from positions 20 to 122 starting from N-terminus of SEQ ID No.32; and the amino acid sequence of the fragment C of tetanus toxin is set forth in the amino acid sequence from positions 20 to 455 starting from N-terminus of SEQ ID No.60.

4. The method according to claim 1, characterized in that the recombinant fusion protein has an amino acid sequence set forth in any one of:
(1) the amino acid sequence set forth in SEQ ID No.32;
(2) the amino acid sequence set forth in SEQ ID No.34;
(3) the amino acid sequence set forth in SEQ ID No.36;
(4) the amino acid sequence set forth in SEQ ID No.38;
(5) the amino acid sequence set forth in SEQ ID No.46;
(6) the amino acid sequence set forth in SEQ ID No.48;
(7) the amino acid sequence set forth in SEQ ID No.50;
(8) the amino acid sequence set forth in SEQ ID No.56;
(9) the amino acid sequence set forth in SEQ ID No.58; and
(10) the amino acid sequence set forth in SEQ ID No.60.

5. The method according to claim 1, characterized in that the recombinant fusion protein is introduced into the bacterium by a recombinant expression vector, and the recombinant expression vector is obtained by inserting a gene encoding the recombinant fusion protein into the multiple cloning site of pMMB66EH.

6. The method according to claim 1, characterized in that the *Neisseria meningitidis* O-oligosaccharyltransferase PglL is introduced into the bacterium by a recombinant expression vector, the recombinant expression vector is obtained by inserting an expression cassette of the *Neisseria meningitidis* O-oligosaccharyltransferase PglL into the multiple cloning site of pET28a(+); and the expression cassette of the *Neisseria meningitidis* O-oligosaccharyltransferase PglL is set forth in SEQ ID No.30.

7. The method according to claim 1, characterized in that the polysaccharide exogenous for the bacterium is obtained by introducing a recombinant expression vector comprising a gene cluster for polysaccharide synthesis into the bacterium; and the sequence of the gene cluster for polysaccharide synthesis is set forth in SEQ ID No.79.

8. The method according to claim 7, characterized in that the recombinant expression vector comprising a gene cluster for polysaccharide synthesis is prepared by the following method: subjecting the DNA molecule set forth in SEQ ID No.79 to double enzyme digestion by Ascl and Notl, to obtain a gene fragment;

subjecting the DNA molecule set forth in SEQ ID No.82 to double enzyme digestion by AscI and NotI, to obtain a large vector fragment; and ligating the gene fragment to the large vector fragment to obtain the recombinant expression vector comprising a gene cluster for polysaccharide synthesis.

9. The method according to claim 1, characterized in that the O-antigen ligase gene-defective bacterium is an O-antigen ligase gene-defective *Shigella flexneri*, an O-antigen ligase gene-defective *Salmonella paratyphi* A or an O-antigen ligase gene-defective *Escherichia coli.*

10. The method according to claim 9, characterized in that the O-antigen ligase gene-defective *Escherichia coli* is a strain of *E. coli* K12.

11. The method according to claim 1, characterized by further comprising the steps of cell lysis, centrifugation and collection of supernatant, desalting and/or separation and purification, after the expression.

* * * * *

SEQUENCE LISTING

<160> NUMBER OF SEQ ID NOS: 82

<210> SEQ ID NO 1
<211> LENGTH: 19
<212> TYPE: DNA
<213> ORGANISM: Artificial Sequence
<220> FEATURE:
<223> OTHER INFORMATION: ipaAp1

<400> SEQUENCE: 1
aagattctgc ctttggacc                                            19

<210> SEQ ID NO 2
<211> LENGTH: 21
<212> TYPE: DNA
<213> ORGANISM: Artificial Sequence
<220> FEATURE:
<223> OTHER INFORMATION: ipaAp2

<400> SEQUENCE: 2
gtggttgaag agttctgtat g                                         21

<210> SEQ ID NO 3
<211> LENGTH: 19
<212> TYPE: DNA
<213> ORGANISM: Artificial Sequence
<220> FEATURE:
<223> OTHER INFORMATION: ipgB1U

<400> SEQUENCE: 3
tgctttgacg gtatacagc                                            19

<210> SEQ ID NO 4
<211> LENGTH: 20
<212> TYPE: DNA
<213> ORGANISM: Artificial Sequence
<220> FEATURE:
<223> OTHER INFORMATION: ipgB1L

<400> SEQUENCE: 4
acttccacag gttgaattcg                                           20

<210> SEQ ID NO 5
<211> LENGTH: 20
<212> TYPE: DNA
<213> ORGANISM: Artificial Sequence
<220> FEATURE:
<223> OTHER INFORMATION: mxiDU

<400> SEQUENCE: 5
aagcaggttt cttctattgg                                           20

<210> SEQ ID NO 6
<211> LENGTH: 21
<212> TYPE: DNA
<213> ORGANISM: Artificial Sequence
<220> FEATURE:
<223> OTHER INFORMATION: mxiDL

<400> SEQUENCE: 6
gaacacatta ccgattacag g                                         21

<210> SEQ ID NO 7
<211> LENGTH: 19
<212> TYPE: DNA
<213> ORGANISM: Artificial Sequence

```
<220> FEATURE:
<223> OTHER INFORMATION: VirGp1

<400> SEQUENCE: 7
catcaatccg ttactcact                                              19

<210> SEQ ID NO 8
<211> LENGTH: 18
<212> TYPE: DNA
<213> ORGANISM: Artificial Sequence
<220> FEATURE:
<223> OTHER INFORMATION: VirGp2

<400> SEQUENCE: 8
actaccagca acaatacg                                               18

<210> SEQ ID NO 9
<211> LENGTH: 20
<212> TYPE: DNA
<213> ORGANISM: Artificial Sequence
<220> FEATURE:
<223> OTHER INFORMATION: incF

<400> SEQUENCE: 9
tgcgagagag agggataac                                              20

<210> SEQ ID NO 10
<211> LENGTH: 19
<212> TYPE: DNA
<213> ORGANISM: Artificial Sequence
<220> FEATURE:
<223> OTHER INFORMATION: incR

<400> SEQUENCE: 10
cgccttttcc atcagtttc                                              19

<210> SEQ ID NO 11
<211> LENGTH: 27
<212> TYPE: DNA
<213> ORGANISM: Artificial Sequence
<220> FEATURE:
<223> OTHER INFORMATION: 301waaIu5

<400> SEQUENCE: 11
cgggatccgg gtatgggaag aatcaag                                     27

<210> SEQ ID NO 12
<211> LENGTH: 26
<212> TYPE: DNA
<213> ORGANISM: Artificial Sequence
<220> FEATURE:
<223> OTHER INFORMATION: 301waaIu3

<400> SEQUENCE: 12
gcgtcgactc agaaatgcta cggtgt                                      26

<210> SEQ ID NO 13
<211> LENGTH: 27
<212> TYPE: DNA
<213> ORGANISM: Artificial Sequence
<220> FEATURE:
<223> OTHER INFORMATION: 301waaId5

<400> SEQUENCE: 13
ccaagctttg gacctttaga caatcaa                                     27
```

<210> SEQ ID NO 14
<211> LENGTH: 26
<212> TYPE: DNA
<213> ORGANISM: Artificial Sequence
<220> FEATURE:
<223> OTHER INFORMATION: 301waaId3

<400> SEQUENCE: 14
ccctcgagat gttaggaagc ataccg                                    26

<210> SEQ ID NO 15
<211> LENGTH: 18
<212> TYPE: DNA
<213> ORGANISM: Artificial Sequence
<220> FEATURE:
<223> OTHER INFORMATION: 301waaIn5

<400> SEQUENCE: 15
tgggtgggat tacaaggt                                             18

<210> SEQ ID NO 16
<211> LENGTH: 19
<212> TYPE: DNA
<213> ORGANISM: Artificial Sequence
<220> FEATURE:
<223> OTHER INFORMATION: 301waaIn3

<400> SEQUENCE: 16
ccaatgacta acacggaaa                                            19

<210> SEQ ID NO 17
<211> LENGTH: 19
<212> TYPE: DNA
<213> ORGANISM: Artificial Sequence
<220> FEATURE:
<223> OTHER INFORMATION: 301waaIw5

<400> SEQUENCE: 17
ctacagatgc tggcgaata                                            19

<210> SEQ ID NO 18
<211> LENGTH: 18
<212> TYPE: DNA
<213> ORGANISM: Artificial Sequence
<220> FEATURE:
<223> OTHER INFORMATION: 301waaIw3

<400> SEQUENCE: 18
tcactacagt tgggatgg                                             18

<210> SEQ ID NO 19
<211> LENGTH: 20
<212> TYPE: DNA
<213> ORGANISM: Artificial Sequence
<220> FEATURE:
<223> OTHER INFORMATION: Kanf5

<400> SEQUENCE: 19
agccgattgt ctgttgtgcc                                           20

<210> SEQ ID NO 20
<211> LENGTH: 20
<212> TYPE: DNA
<213> ORGANISM: Artificial Sequence
<220> FEATURE:
<223> OTHER INFORMATION: Kanf3

<400> SEQUENCE: 20
ttgtcactga agcgggaagg                                              20

<210> SEQ ID NO 21
<211> LENGTH: 28
<212> TYPE: DNA
<213> ORGANISM: Artificial Sequence
<220> FEATURE:
<223> OTHER INFORMATION: Kan5

<400> SEQUENCE: 21
gcgtcgacgt gtaggctgga gctgcttc                                     28

<210> SEQ ID NO 22
<211> LENGTH: 28
<212> TYPE: DNA
<213> ORGANISM: Artificial Sequence
<220> FEATURE:
<223> OTHER INFORMATION: Kan3

<400> SEQUENCE: 22
ccaagcttat gggaattagc catggtcc                                     28

<210> SEQ ID NO 23
<211> LENGTH: 2828
<212> TYPE: DNA
<213> ORGANISM: Artificial Sequence
<220> FEATURE:
<223> OTHER INFORMATION: S flexneri 2a

<400> SEQUENCE: 23
ggatccgggt atgggaagaa tcaagtagag tgtcgttcta caagtatgtc tcttgcagat      60
ttgccagctc aaaccgtttt tcaaaattta atcttgaaa taataaccaa taagttgaca     120
tcggagataa gatgacctca acattatttt tctctctcga gaaaaaaaac tggatagcgt     180
actggaacag agctctcgta ttcttattca ttaccaccta tttttgggt gggattacaa      240
ggtataaaca tcttattgtt attcttatga caataacgac aatcgtctat ctctgcaaac     300
ggccaaaaca ctatctctca ctatttaaaa catttcttt tggtagtgtt gccatattaa      360
ctattgctgc attgctgtca cttcttcaat cccctgatgc aggtgctagc atgaaggaag     420
ttttcaaagc tattattgag aatactttac tatgcacaat agcaataccg gtcatattga     480
gagacgagaa aagagaagat gtcgaaaaaa tcgttttctt ctcatttatt agtgcgttgg     540
gcttacgctg tttttctgaa ttgattacct attataagga ctatcaacaa gggataatgc     600
cattcgcaga ttatagacac cgtagcattt ctgagtcgac gtgtaggctg agctgcttc     660
gaagttccta actttctag aaataggaa cttcggaata ggaacttcaa gatcccctca      720
cgctgccgca agcactcagg gcgcaagggc tgctaaagga agcggaacac gtagaaagcc     780
agtccgcaga aacggtgctg accccggatg aatgtcagct actgggctat ctggacaagg     840
gaaaacgcaa gcgcaaagag aaagcaggta gcttgcagtg gcttacatg gcgatagcta      900
gactgggcgg ttttatggac agcaagcgaa ccggaattgc cagctggggc gccctctggt     960
aaggttggga agccctgcaa agtaaactgg atggctttct tgccgccaag gatctgatgg    1020
cgcaggggat caagatctga tcaagagaca ggatgaggat cgtttcgcat gattgaacaa    1080
gatggattgc acgcaggttc tccggccgct tgggtggaga ggctattcgg ctatgactgg    1140
gcacaacaga caatcggctg ctctgatgcc gccgtgttcc ggctgtcagc gcaggggcgc    1200

```
ccggttctttt tgtcaagac cgacctgtcc ggtgccctga atgaactgca ggacgaggca      1260
gcgcggctat cgtggctggc cacgacgggc gttccttgcg cagctgtgct cgacgttgtc      1320
actgaagcgg aagggactg gctgctattg gcgaagtgc cggggcagga tctcctgtca        1380
tctcaccttg ctcctgccga aaagtatcc atcatggctg atgcaatgcg gcggctgcat       1440
acgcttgatc cggctacctg cccattcgac caccaagcga acatcgcat cgagcgagca      1500 cgtactcgga tggaagccgg tcttgtcgat caggatgatc tggacgaaga gcatcagggg     1560
ctcgcgccag ccgaactgtt cgccaggctc aaggcgcgca tgcccgacgg cgaggatctc     1620
gtcgtgaccc atggcgatgc ctgcttgccg aatatcatgg tggaaaatgg ccgcttttct      1680
ggattcatcg actgtggccg gctgggtgtg gcggaccgct atcaggacat agcgttggct      1740
acccgtgata ttgctgaaga gcttggcggc gaatgggctg accgcttcct cgtgctttac     1800
ggtatcgccg ctcccgattc gcagcgcatc gccttctatc gccttcttga cgagttcttc     1860
tgagcgggac tctggggttc gaaatgaccg accaagcgac gcccaacctg ccatcacgag    1920
atttcgattc caccgccgcc ttctatgaaa ggttgggctt cggaatcgtt ttccgggacg     1980
ccggctggat gatcctccag cgcggggatc tcatgctgga gttcttcgcc cacccccagct   2040 tcaaaagcgc tctgaagttc ctatactttc tagagaatag gaacttcgga ataggaacta      2100
aggaggatat tcatatggac catggctaat tcccataagc tttggacctt tagacaatca      2160
atagggccac ataattttgc gctattcatc tggtttggca ctggtttatt agggctggta      2220
agtcttatga tgctatactg tgcaatattg aaagagtgta taaaaaatgg cgtcaagaat      2280
aaatatcgct caccatataa tgcatattat ataatcttac tatctttat aggttatttt        2340 gttatccgtg gaaacgtaga acaaattgaa ccaaatttat taggcgttta cgccggctta     2400
ttattagcga tgaaaaacaa gtaaaaaata aaaaaggctg cataatgcgg cctttttatt      2460
tattcaaacc aattatgaat aacctcttcg aatctttgag ttacgccatc ccaactgtag    2520
tgatcaaaca caaagtcctg accttgcttt gcaactgctg ttaattcagg attcgctaac     2580 gttttttaaaa tatcgctgct tatggagtct gcagtcatag gttcttttaa atggaatccc     2640
gtagtatttt ctttgacaaa ttccgtcatc cccccacgcg tactcactaa aacaggctta     2700
ccagcaccca tagcttcaat tgccaccatg caaaatggtt cctggaactg ggaaggaatg    2760
acgactaaat ctgccagtgg gtaataacaa tacatctttt caggcggtat gcttcctaac    2820
atctcgag                                                            2828

<210> SEQ ID NO 24
<211> LENGTH: 28
<212> TYPE: DNA
<213> ORGANISM: Artificial Sequence
<220> FEATURE:
<223> OTHER INFORMATION: pETKan Primer

<400> SEQUENCE: 24
gcgtcgacgt gtaggctgga gctgcttc                                           28

<210> SEQ ID NO 25
<211> LENGTH: 28
<212> TYPE: DNA
<213> ORGANISM: Artificial Sequence
<220> FEATURE:
<223> OTHER INFORMATION: pETKan Primer

<400> SEQUENCE: 25
ccaagcttat gggaattagc catggtcc                                            28
```

<210> SEQ ID NO 26
<211> LENGTH: 604
<212> TYPE: PRT
<213> ORGANISM: Artificial Sequence
<220> FEATURE:
<223> OTHER INFORMATION: AA sequence of 0-oligosaccharyliransterase PglL

<400> SEQUENCE: 26

```
Met Pro Ala Glu Thr Thr Val Ser Gly Ala His Pro Ala Ala Lys Leu
 1               5                  10                  15

Pro Ile Tyr Ile Leu Pro Cys Phe Leu Trp Ile Gly Ile Val Pro Phe
             20                  25                  30

Thr Phe Ala Leu Lys Leu Lys Pro Ser Pro Asp Phe Tyr His Asp Ala
         35                  40                  45

Ala Ala Ala Ala Gly Leu Ile Val Leu Leu Phe Leu Thr Ala Gly Lys
 50                  55                  60

Lys Leu Phe Asp Val Lys Ile Pro Ala Ile Ser Phe Leu Leu Phe Ala
 65                  70                  75                  80

Met Ala Ala Phe Trp Tyr Leu Gln Ala Arg Leu Met Asn Leu Ile Tyr
                 85                  90                  95

Pro Gly Met Asn Asp Ile Val Ser Trp Ile Phe Ile Leu Leu Ala Val
            100                 105                 110

Ser Ala Trp Ala Cys Arg Ser Leu Val Ala His Phe Gly Gln Glu Arg
        115                 120                 125

Ile Val Thr Leu Phe Ala Trp Ser Leu Leu Ile Gly Ser Leu Leu Gln
    130                 135                 140

Ser Cys Ile Val Val Ile Gln Phe Ala Gly Trp Glu Asp Thr Pro Leu
145                 150                 155                 160

Phe Gln Asn Ile Ile Val Tyr Ser Gly Gln Gly Val Ile Gly His Ile
                165                 170                 175

Gly Gln Arg Asn Asn Leu Gly His Tyr Leu Met Trp Gly Ile Leu Ala
            180                 185                 190

Ala Ala Tyr Leu Asn Gly Gln Arg Lys Ile Pro Ala Ala Leu Gly Val
        195                 200                 205

Ile Cys Leu Ile Met Gln Thr Ala Val Leu Gly Leu Val Asn Ser Arg
    210                 215                 220

Thr Ile Leu Thr Tyr Ile Ala Ala Ile Ala Leu Ile Leu Pro Phe Trp
225                 230                 235                 240

Tyr Phe Arg Ser Asp Lys Ser Asn Arg Arg Thr Met Leu Gly Ile Ala
                245                 250                 255

Ala Ala Val Phe Leu Thr Ala Leu Phe Gln Phe Ser Met Asn Thr Ile
            260                 265                 270

Leu Glu Thr Phe Thr Gly Ile Arg Tyr Glu Thr Ala Val Glu Arg Val
        275                 280                 285

Ala Asn Gly Gly Phe Thr Asp Leu Pro Arg Gln Ile Glu Trp Asn Lys
    290                 295                 300

Ala Leu Ala Ala Phe Gln Ser Ala Pro Ile Phe Gly His Gly Trp Asn
305                 310                 315                 320

Ser Phe Ala Gln Gln Thr Phe Leu Ile Asn Ala Glu Gln His Asn Ile
                325                 330                 335

Tyr Asp Asn Leu Leu Ser Asn Leu Phe Thr His Ser His Asn Ile Val
            340                 345                 350

Leu Gln Leu Leu Ala Glu Met Gly Ile Ser Gly Thr Leu Leu Val Ala
        355                 360                 365
```

```
Ala Thr Leu Leu Thr Gly Ile Ala Gly Leu Leu Lys Arg Pro Leu Thr
    370                 375                 380

Pro Ala Ser Leu Phe Leu Ile Cys Thr Leu Ala Val Ser Met Cys His
385                 390                 395                 400

Ser Met Leu Glu Tyr Pro Leu Trp Tyr Val Tyr Phe Leu Ile Pro Phe
                405                 410                 415

Gly Leu Met Leu Phe Leu Ser Pro Ala Glu Ala Ser Asp Gly Ile Ala
                420                 425                 430

Phe Lys Lys Ala Ala Asn Leu Gly Ile Leu Thr Ala Ser Ala Ala Ile
            435                 440                 445

Phe Ala Gly Leu Leu His Leu Asp Trp Thr Tyr Thr Arg Leu Val Asn
    450                 455                 460

Ala Phe Ser Pro Ala Thr Asp Asp Ser Ala Lys Thr Leu Asn Arg Lys
465                 470                 475                 480

Ile Asn Glu Leu Arg Tyr Ile Ser Ala Asn Ser Pro Met Leu Ser Phe
                485                 490                 495

Tyr Ala Asp Phe Ser Leu Val Asn Phe Ala Leu Pro Glu Tyr Pro Glu
                500                 505                 510

Thr Gln Thr Trp Ala Glu Glu Ala Thr Leu Lys Ser Leu Lys Tyr Arg
            515                 520                 525

Pro His Ser Ala Thr Tyr Arg Ile Ala Leu Tyr Leu Met Arg Gln Gly
    530                 535                 540

Lys Val Ala Glu Ala Lys Gln Trp Met Arg Ala Thr Gln Ser Tyr Tyr
545                 550                 555                 560

Pro Tyr Leu Met Pro Arg Tyr Ala Asp Glu Ile Arg Lys Leu Pro Val
                565                 570                 575

Trp Ala Pro Leu Leu Pro Glu Leu Leu Lys Asp Cys Lys Ala Phe Ala
            580                 585                 590

Ala Ala Pro Gly His Pro Glu Ala Lys Pro Cys Lys
    595                 600
```

<210> SEQ ID NO 27
<211> LENGTH: 1815
<212> TYPE: DNA
<213> ORGANISM: Artificial Sequence
<220> FEATURE:
<223> OTHER INFORMATION: DNA sequence of 0-oligosaccharyliransterase PglL

<400> SEQUENCE: 27

```
atgcccgctg aaacgaccgt atccggcgcg caccccgccg ccaaactgcc gatttacatc      60
ctgccctgct tcctttggat aggcatcgtc ccctttacct tcgcgctcaa actgaaaccg     120
tcgcccgact tttaccacga tgccgccgcc gcagccggcc tgattgtcct gttgttcctc     180
acggcaggaa aaaaactgtt tgatgtcaaa atccccgcca tcagcttcct tctgtttgca     240
atggcggcgt tttggtatct tcaggcacgc ctgatgaacc tgatttaccc cggtatgaac     300
gacatcgtct cttggatttt catcttgctc gccgtcagcg cgtgggcctg ccggagcttg     360
gtcgcacact tcggacaaga acgcatcgtg accctgtttg cctggtcgct gcttatcggc     420
tccctgcttc aatcctgcat cgtcgtcatc cagtttgccg gctgggaaga cacccctctg     480
tttcaaaaca tcatcgttta cagcgggcaa ggcgtaatcg acacatcgg gcagcgcaac     540 aacctcggac actacctcat gtggggcata tcgccgccg cctacctcaa cggacaacga     600
aaaatccccg ccgccctcgg cgtaatctgc ctgattatgc agaccgccgt tttaggtttg     660
```

| | |
|---|---|
| gtcaactcgc gcaccatctt gacctacata gccgccatcg ccctcatcct tcccttctgg | 720 |
| tatttccgtt cggacaaatc caacaggcgg acgatgctcg gcatagccgc agccgtattc | 780 |
| cttaccgcgc tgttccaatt ttccatgaac accattctgg aaacctttac tggcatccgc | 840 |
| tacgaaactg ccgtcgaacg cgtcgccaac ggcggtttca cagacttgcc gcgccaaatc | 900 |
| gaatggaata aagcccttgc cgccttccag tccgccccga tattcgggca cggctggaac | 960 |
| agttttgccc aacaaacctt cctcatcaat gccgaacagc acaacatata cgacaacctc | 1020 |
| ctcagcaact tgttcaccca ttcccacaac atcgtcctcc aactccttgc agagatggga | 1080 |
| atcagcggca cgcttctggt tgccgcaacc ctgctgacgg gcattgccgg gctgcttaaa | 1140 |
| cgcccctga cccccgcatc gcttttccta atctgcacgc ttgccgtcag tatgtgccac | 1200 |
| agtatgctcg aatatccttt gtggtatgtc tatttcctca tcccttcgg actgatgctc | 1260 |
| ttcctgtccc ccgcagaggc ttcagacggc atcgccttca aaaagccgc caatctcggc | 1320 |
| atactgaccg cctccgccgc catattcgca ggattgctgc acttggactg gacatacacc | 1380 |
| cggctggtta acgccttttc ccccgccact gacgacagtg ccaaaaccct caaccggaaa | 1440 |
| atcaacgagt tgcgctatat ttccgcaaac agtccgatgc tgtccttta tgccgacttc | 1500 |
| tccctcgtaa acttcgccct gccggaatac cccgaaaccc agacttgggc ggaagaagca | 1560 |
| accctcaaat cactaaaata ccgccccac tccgccacct accgcatcgc cctctacctg | 1620 |
| atgcggcaag gcaaagttgc agaagcaaaa caatggatgc gggcgacaca gtcctattac | 1680 |
| ccctacctga tgccccgata cgccgacgaa atccgcaaac tgcccgtatg ggcgccgctg | 1740 |
| ctaccccgaac tgctcaaaga ctgcaaagcc ttcgccgccg cgcccggtca tccggaagca | 1800 |
| aaaccctgca aatga | 1815 |

```
<210> SEQ ID NO 28
<211> LENGTH: 34
<212> TYPE: DNA
<213> ORGANISM: Artificial Sequence
<220> FEATURE:
<223> OTHER INFORMATION: 223tac-box5'

<400> SEQUENCE: 28
```

| | |
|---|---|
| atcgagatct actgcataat tcgtgtcgct caag | 34 |

```
<210> SEQ ID NO 29
<211> LENGTH: 34
<212> TYPE: DNA
<213> ORGANISM: Artificial Sequence
<220> FEATURE:
<223> OTHER INFORMATION: 223tac-box3'

<400> SEQUENCE: 29
```

| | |
|---|---|
| atcgagatct gtctcatgag cggatacata tttg | 34 |

```
<210> SEQ ID NO 30
<211> LENGTH: 2488
<212> TYPE: DNA
<213> ORGANISM: Artificial Sequence
<220> FEATURE:
<223> OTHER INFORMATION: Pg1L

<400> SEQUENCE: 30
```

| | |
|---|---|
| atcgagatct actgcataat tcgtgtcgct caaggcgcac tcccgttctg gataatgttt | 60 |
| tttgcgccga catcataacg gttctggcaa atattctgaa atgagctgtt gacaattaat | 120 |
| catcggctcg tataatgtgt ggaattgtga gcggataaca atttcacaca ggaaacagaa | 180 |

```
ttcatgcccg ctgaaacgac cgtatccggc gcgcacccccg ccgccaaact gccgatttac      240
atcctgccct gcttcctttg dataggcatc gtcccctta ccttcgcgct caaactgaaa      300
ccgtcgcccg acttttacca cgatgccgcc gccgcagccg gcctgattgt cctgttgttc      360
ctcacggcag gaaaaaaact gtttgatgtc aaaatccccg ccatcagctt ccttctgttt      420
gcaatggcgg cgttttggta tcttcaggca cgcctgatga acctgattta ccccggtatg      480
aacgacatcg tctcttggat tttcatcttg ctcgccgtca gcgcgtgggc ctgccggagc      540
ttggtcgcac acttcggaca agaacgcatc gtgaccctgt ttgcctggtc gctgcttatc      600
ggctccctgc ttcaatcctg catcgtcgtc atccagtttg ccggctggga agacacccct      660
ctgtttcaaa acatcatcgt ttacagcggg caaggcgtaa tcggacacat cgggcagcgc      720
aacaacctcg gacactacct catgtggggc atactcgccg ccgcctacct caacggacaa      780
cgaaaaatcc ccgccgccct cggcgtaatc tgcctgatta tgcagaccgc cgttttaggt      840
ttggtcaact cgcgcaccat cttgacctac atagccgcca tcgccctcat ccttcccttc      900
tggtatttcc gttcggacaa atccaacagg cggacgatgc tcggcatagc cgcagccgta      960
ttccttaccg cgctgttcca attttccatg aacaccattc tggaaacctt tactggcatc     1020
cgctacgaaa ctgccgtcga acgcgtcgcc aacggcggtt tcacagactt gccgcgccaa     1080
atcgaatgga ataaagccct tgccgccttc cagtccgccc cgatattcgg cacggctgg      1140 aacagttttg cccaacaaac cttcctcatc aatgccgaac agcacaacat atacgacaac     1200
ctcctcagca acttgttcac ccattccac aacatcgtcc tccaactcct tgcagagatg     1260
ggaatcagcg gcacgcttct ggttgccgca accctgctga cgggcattgc cgggctgctt     1320
aaacgccccc tgaccccccgc atcgcttttc ctaatctgca cgcttgccgt cagtatgtgc     1380
cacagtatgc tcgaatatcc tttgtggtat gtctatttcc tcatcccttt cggactgatg     1440
ctcttcctgt cccccgcaga ggcttcgac ggcatcgcct tcaaaaaagc cgccaatctc     1500
ggcatactga ccgcctccgc cgccatattc gcaggattgc tgcacttgga ctggacatac     1560
acccggctgg ttaacgcctt tccccccgcc actgacgaca gtgccaaaac cctcaaccgg     1620
aaaatcaacg agttgcgcta tatttccgca aacagtccga tgctgtcctt ttatgccgac     1680 ttctcccctcg taaacttcgc cctgccggaa taccccgaaa cccagacttg ggcggaagaa     1740
gcaaccctca aatcactaaa ataccgcccc cactccgcca cctaccgcat cgccctctac     1800
ctgatgcggc aaggcaaagt tgcagaagca aaacaatgga tgcgggcgac acagtcctat     1860 taccccctacc tgatgcccg atacgccgac gaaatccgca aactgcccgt atgggcgccg     1920
ctgctacccg aactgctcaa agactgcaaa gccttcgccg ccgcgccggg tcatccggaa     1980
gcaaaaccct gcaaatgaaa gcttggctgt tttggcggat gagagaagat tttcagcctg     2040
atacagatta aatcagaacg cagaagcggt ctgataaaac agaatttgcc tggcggcagt     2100
agcgcggtgg tcccacctga ccccatgccg aactcagaag tgaaacgccg tagcgccgat     2160
ggtagtgtgg ggtctcccca tgcgagagta gggaactgcc aggcatcaaa taaaacgaaa     2220
ggctcagtcg aaagactggg cctttcgttt tatctgttgt ttgtcggtga acgctctcct     2280
gagtaggaca aatccgccgg gagcggattt gaacgttgcg aagcaacggc ccggagggtg     2340
gcgggcagga cgcccgccat aaactgccag gcatcaaatt aagcagaagg ccatcctgac     2400
ggatggcctt tttgcgtttc tacaaactct tttgtttatt tttctaaata cattcaaata     2460
tgtatccgct catgagacag atctcgat                                        2488
```

<210> SEQ ID NO 31
<211> LENGTH: 513
<212> TYPE: DNA
<213> ORGANISM: Artificial Sequence
<220> FEATURE:
<223> OTHER INFORMATION: rCTB4573

<400> SEQUENCE: 31

| | | | | | |
|---|---|---|---|---|---|
| gaattcatga | agaaaatttg | gctggcctta | gccggcctgg | ttctggcatt | cagcgccagc | 60 |
| gcaaccccgc | agaacatcac | cgacctgtgc | gccgagtacc | acaacaccca | aatttatacc | 120 |
| ctgaacgaca | aaatttttag | ctacaccgag | agcctggcag | gcaagcgcga | gatggccatc | 180 |
| atcaccttca | agaacggcgc | cattttccag | gtggaggtgc | cgggcagcca | gcacatcgac | 240 |
| agtcagaaga | aggccatcga | gcgcatgaag | gacaccctgc | gcatcgccta | cctgaccgag | 300 |
| gccaaggtgg | agaagctgtg | cgtgtggaac | aacaagaccc | cgcacgccat | cgccgcaatc | 360 |
| agcatggcca | acgaccagaa | cgccaccagc | gccgtgaccg | agtactatct | gaaccatggc | 420 |
| gagtggccgg | gtaataacac | cagcgccggc | gtggccacaa | gcagtgagat | caagggcggc | 480 |
| ggatcccacc | atcaccacca | ccattaaaag | ctt | | | 513 |

<210> SEQ ID NO 32
<211> LENGTH: 166
<212> TYPE: PRT
<213> ORGANISM: Artificial Sequence
<220> FEATURE:
<223> OTHER INFORMATION: rCTB4573

<400> SEQUENCE: 32

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Thr Ser Ser Glu Ile Lys Gly Gly Gly Ser
145                 150                 155                 160

His His His His His His
                165

<210> SEQ ID NO 33
<211> LENGTH: 504
<212> TYPE: DNA
<213> ORGANISM: Artificial Sequence
<220> FEATURE:
<223> OTHER INFORMATION: rCTB4571

-continued

```
<400> SEQUENCE: 33
gaattcatga agaaaatttg gctggcctta gccggcctgg ttctggcatt cagcgccagc      60
gcaaccccgc agaacatcac cgacctgtgc gccgagtacc acaacaccca aatttatacc     120
ctgaacgaca aaatttttag ctacaccgag agcctggcag gcaagcgcga gatggccatc     180
atcaccttca agaacggcgc cattttccag gtggaggtgc cgggcagcca gcacatcgac     240
agtcagaaga aggccatcga gcgcatgaag gacaccctgc gcatcgccta cctgaccgag     300
gccaaggtgg agaagctgtg cgtgtggaac aacaagaccc cgcacgccat cgccgcaatc     360
agcatggcca cgaccagaa cgccaccagc gccgtgaccg agtactatct gaaccatggc      420
gagtggccgg gtaataacac cagcgccggc gtggccacaa gcagtgaggg cggcggccac     480
catcaccacc accattaaaa gctt                                            504

<210> SEQ ID NO 34
<211> LENGTH: 163
<212> TYPE: PRT
<213> ORGANISM: Artificial Sequence
<220> FEATURE:
<223> OTHER INFORMATION: rCTB4571

<400> SEQUENCE: 34

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Thr Ser Ser Glu Gly Gly Gly His His His
145                 150                 155                 160

His His His

<210> SEQ ID NO 35
<211> LENGTH: 498
<212> TYPE: DNA
<213> ORGANISM: Artificial Sequence
<220> FEATURE:
<223> OTHER INFORMATION: rCTB4569

<400> SEQUENCE: 35
gaattcatga agaaaatttg gctggcctta gccggcctgg ttctggcatt cagcgccagc      60
gcaaccccgc agaacatcac cgacctgtgc gccgagtacc acaacaccca aatttatacc     120
ctgaacgaca aaatttttag ctacaccgag agcctggcag gcaagcgcga gatggccatc     180
atcaccttca agaacggcgc cattttccag gtggaggtgc cgggcagcca gcacatcgac     240
```

```
agtcagaaga aggccatcga gcgcatgaag acaccctgc gcatcgccta cctgaccgag    300
gccaaggtgg agaagctgtg cgtgtggaac aacaagaccc cgcacgccat cgccgcaatc    360
agcatggcca acgaccagaa cgccaccagc gccgtgaccg agtactatct gaaccatggc    420
gagtggccgg gtaataacac cagcgccggc gtggccacaa gcggcggcgg ccaccatcac    480
caccaccatt aaaagctt                                                  498
```

```
<210> SEQ ID NO 36
<211> LENGTH: 161
<212> TYPE: PRT
<213> ORGANISM: Artificial Sequence
<220> FEATURE:
<223> OTHER INFORMATION: rCTB4569

<400> SEQUENCE: 36
```

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Thr Ser Gly Gly Gly His His His His His
145                 150                 155                 160

His

```
<210> SEQ ID NO 37
<211> LENGTH: 492
<212> TYPE: DNA
<213> ORGANISM: Artificial Sequence
<220> FEATURE:
<223> OTHER INFORMATION: rCTB4567

<400> SEQUENCE: 37
gaattcatga agaaaatttg gctggcctta gccggcctgg ttctggcatt cagcgccagc    60
gcaaccccgc agaacatcac cgacctgtgc gccgagtacc acaacaccca aatttatacc    120
ctgaacgaca aaattttag ctacaccgag agcctggcag gcaagcgcga gatggccatc    180
atcaccttca gaacggcgc cattttccag gtggaggtgc cgggcagcca gcacatcgac    240
agtcagaaga aggccatcga gcgcatgaag acaccctgc gcatcgccta cctgaccgag    300
gccaaggtgg agaagctgtg cgtgtggaac aacaagaccc cgcacgccat cgccgcaatc    360
agcatggcca acgaccagaa cgccaccagc gccgtgaccg agtactatct gaaccatggc    420
gagtggccgg gtaataacac cagcgccggc gtggccggcg cggccacca tcaccaccac    480
```
cattaaaagc tt 492

<210> SEQ ID NO 38
<211> LENGTH: 159
<212> TYPE: PRT
<213> ORGANISM: Artificial Sequence
<220> FEATURE:
<223> OTHER INFORMATION: rCTB4567

<400> SEQUENCE: 38

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Gly Gly Gly His His His His His
145                 150                 155

<210> SEQ ID NO 39
<211> LENGTH: 489
<212> TYPE: DNA
<213> ORGANISM: Artificial Sequence
<220> FEATURE:
<223> OTHER INFORMATION: rCTB4566

<400> SEQUENCE: 39
gaattcatga agaaaatttg gctggcctta gccggcctgg ttctggcatt cagcgccagc    60
gcaaccccgc agaacatcac cgacctgtgc gccgagtacc acaacaccca aatttatacc   120
ctgaacgaca aaattttttag ctacaccgag agcctggcag gcaagcgcga gatggccatc   180
atcaccttca agaacggcgc catttttccag gtggaggtgc cgggcagcca gcacatcgac   240
agtcagaaga aggccatcga gcgcatgaag gacaccctgc gcatcgccta cctgaccgag   300
gccaaggtgg agaagctgtg cgtgtggaac aacaagaccc cgcacgccat cgccgcaatc   360
agcatggcca acgaccagaa cgccaccagc gccgtgaccg agtactatct gaaccatggc   420
gagtggccgg gtaataacac cagcgccggc gtgggcggcg gccaccatca ccaccaccat   480
taaaagctt                                                           489

<210> SEQ ID NO 40
<211> LENGTH: 158
<212> TYPE: PRT
<213> ORGANISM: Artificial Sequence
<220> FEATURE:
<223> OTHER INFORMATION: rCTB4566

<400> SEQUENCE: 40

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
                20                  25                  30

Asn Thr Gln Ile Tyr Thr Leu Asn Asp Lys Ile Phe Ser Tyr Thr Glu
            35                  40                  45

Ser Leu Ala Gly Lys Arg Glu Met Ala Ile Ile Thr Phe Lys Asn Gly
        50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
130                 135                 140

Thr Ser Ala Gly Val Gly Gly Gly His His His His His His
145                 150                 155

<210> SEQ ID NO 41
<211> LENGTH: 486
<212> TYPE: DNA
<213> ORGANISM: Artificial Sequence
<220> FEATURE:
<223> OTHER INFORMATION: rCTB4565

<400> SEQUENCE: 41
gaattcatga agaaaatttg gctggcctta gccggcctgg ttctggcatt cagcgccagc      60
gcaaccccgc agaacatcac cgacctgtgc gccgagtacc acaacaccca aatttatacc     120
ctgaacgaca aaatttttag ctacaccgag agcctggcag gcaagcgcga gatggccatc     180
atcaccttca agaacggcgc cattttccag gtggaggtgc cgggcagcca gcacatcgac     240
agtcagaaga aggccatcga gcgcatgaag gacaccctgc gcatcgccta cctgaccgag     300
gccaaggtgg agaagctgtg cgtgtggaac aacaagaccc cgcacgccat cgccgcaatc     360
agcatggcca cgaccagaa cgccaccagc gccgtgaccg agtactatct gaaccatggc     420
gagtggccgg gtaataacac cagcgccggc ggcggcggcc accatcacca ccaccattaa     480
aagctt                                                                486

<210> SEQ ID NO 42
<211> LENGTH: 157
<212> TYPE: PRT
<213> ORGANISM: Artificial Sequence
<220> FEATURE:
<223> OTHER INFORMATION: rCTB4565

<400> SEQUENCE: 42

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
                20                  25                  30

Asn Thr Gln Ile Tyr Thr Leu Asn Asp Lys Ile Phe Ser Tyr Thr Glu
            35                  40                  45

Ser Leu Ala Gly Lys Arg Glu Met Ala Ile Ile Thr Phe Lys Asn Gly

```
    50                  55                  60
Ala Ile Phe Gln Val Glu Val Pro Gly Ser Gln His Ile Asp Ser Gln
 65                  70                  75                  80

Lys Lys Ala Ile Glu Arg Met Lys Asp Thr Leu Arg Ile Ala Tyr Leu
                 85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Gly Gly Gly His His His His His His
145                 150                 155
```

<210> SEQ ID NO 43
<211> LENGTH: 483
<212> TYPE: DNA
<213> ORGANISM: Artificial Sequence
<220> FEATURE:
<223> OTHER INFORMATION: rCTB4564

<400> SEQUENCE: 43

```
gaattcatga agaaaatttg gctggcctta gccggcctgg ttctggcatt cagcgccagc      60
gcaacccccgc agaacatcac cgacctgtgc gccgagtacc acaacaccca aatttatacc   120
ctgaacgaca aaatttttag ctacaccgag agcctggcag gcaagcgcga gatggccatc   180
atcaccttca agaacggcgc cattttccag gtggaggtgc cgggcagcca gcacatcgac   240
agtcagaaga aggccatcga gcgcatgaag gacaccctgc gcatcgccta cctgaccgag   300
gccaaggtgg agaagctgtg cgtgtggaac aacaagaccc cgcacgccat cgccgcaatc   360
agcatggcca acgaccagaa cgccaccagc gccgtgaccg agtactatct gaaccatggc   420
gagtggccgg gtaataacac cagcgccggc ggcggccacc atcaccacca ccattaaaag   480
ctt                                                                  483
```

<210> SEQ ID NO 44
<211> LENGTH: 156
<212> TYPE: PRT
<213> ORGANISM: Artificial Sequence
<220> FEATURE:
<223> OTHER INFORMATION: rCTB4564

<400> SEQUENCE: 44

```
Met Lys Lys Ile Trp Leu Ala Leu Ala Gly Leu Val Leu Ala Phe Ser
  1               5                  10                  15

Ala Ser Thr Pro Gln Asn Ile Thr Asp Leu Cys Ala Glu Tyr His
             20                  25                  30

Asn Thr Gln Ile Tyr Thr Leu Asn Asp Lys Ile Phe Ser Tyr Thr Glu
         35                  40                  45

Ser Leu Ala Gly Lys Arg Glu Met Ala Ile Ile Thr Phe Lys Asn Gly
     50                  55                  60

Ala Ile Phe Gln Val Glu Val Pro Gly Ser Gln His Ile Asp Ser Gln
 65                  70                  75                  80

Lys Lys Ala Ile Glu Arg Met Lys Asp Thr Leu Arg Ile Ala Tyr Leu
                 85                  90                  95

Thr Glu Ala Lys Val Glu Lys Leu Cys Val Trp Asn Asn Lys Thr Pro
            100                 105                 110
```

His Ala Ile Ala Ala Ile Ser Met Ala Asn Asp Gln Asn Ala Thr Ser
            115                 120                 125

Ala Val Thr Glu Tyr Tyr Leu Asn His Gly Glu Trp Pro Gly Asn Asn
        130                 135                 140

Thr Ser Ala Gly Gly Gly His His His His His
145                 150                 155

<210> SEQ ID NO 45
<211> LENGTH: 2037
<212> TYPE: DNA
<213> ORGANISM: Artificial Sequence
<220> FEATURE:
<223> OTHER INFORMATION: rEPA4573

<400> SEQUENCE: 45

| | | | | | |
|---|---|---|---|---|---|
| gaattcatga | aaaagatttg | gctggcgctg | gctggtttag | ttttagcgtt | tagcgcatcg | 60 |
| gcggccgagg | aagccttcga | cctctggaac | gaatgcgcca | agcctgcgt | gctcgacctc | 120 |
| aaggacggcg | tgcgttccag | ccgcatgagc | gtcgacccgg | ccatcgccga | caccaacggc | 180 |
| cagggcgtgc | tgcactactc | catggtcctg | gagggcggca | cgacgcgct | caagctggcc | 240 |
| atcgacaacg | ccctcagcat | caccagcgac | ggcctgacca | tccgcctcga | aggcggcgtc | 300 |
| gagccgaaca | agccggtgcg | ctacagctac | acgcgccagg | cgcgcggcag | ttggtcgctg | 360 |
| aactggctgg | taccgatcgg | ccacgagaag | ccctcgaaca | tcaaggtgtt | catccacgaa | 420 |
| ctgaacgccg | gtaaccagct | cagccacatg | tcgccgatct | acaccatcga | gatgggcgac | 480 |
| gagttgctgg | cgaagctggc | gcgcgatgcc | accttcttcg | tcaggcgcca | cgagagcaac | 540 |
| gagatgcagc | cgacgctcgc | catcagccat | gccggggtca | gcgtggtcat | ggcccaggcc | 600 |
| cagccgcgcc | gggaaaagcg | ctggagcgaa | tgggccagcg | gcaaggtgtt | gtgcctgctc | 660 |
| gacccgctgg | acggggtcta | caactacctc | gcccagcagc | gctgcaacct | cgacgatacc | 720 |
| tgggaaggca | agatctaccg | ggtgctcgcc | ggcaacccgg | cgaagcatga | cctggacatc | 780 |
| aagcccacgg | tcatcagtca | tcgcctgcac | ttccccgagg | gcggcagcct | ggccgcgctg | 840 |
| accgcgcacc | aggcttgcca | cctgccgctg | gagactttca | ccgtcatcg | ccagccgcgc | 900 |
| ggctgggaac | aactggagca | gtgcggctat | ccggtgcagc | ggctggtcgc | cctctacctg | 960 |
| gcggcgcggc | tgtcgtggaa | ccaggtcgac | caggtgatcg | caacgccct | ggccagcccc | 1020 |
| ggcagcggcg | gcgacctggg | cgaagcgatc | cgcgagcagc | cggagcaggc | ccgtctggcc | 1080 |
| ctgaccctgg | ccgccgccga | gagcgagcgc | ttcgtccggc | agggcaccgg | caacgacgag | 1140 |
| gccggcgcgc | cagcgccga | cgtggtgagc | ctgacctgcc | cggtcgccgc | cggtgaatgc | 1200 |
| gcgggcccgg | cggacagcgg | cgacgccctg | ctggagcgca | actatcccac | tggcgcggag | 1260 |
| ttcctcggcg | acggcggcga | catcagcttc | agcacccgcg | gcacgcagaa | ctggacggtg | 1320 |
| gagcggctgc | tccaggcgca | ccgccaactg | gaggagcgcg | gctatgtgtt | cgtcggctac | 1380 |
| cacggcacct | tcctcgaagc | ggcgcaaagc | atcgtcttcg | gcggggtgcg | cgcgcgcagc | 1440 |
| caggacctcg | acgcgatctg | gcgcggtttc | tatatcgccg | gcgatccggc | gctggcctac | 1500 |
| ggctacgccc | aggaccagga | acccgacgcg | cgcggccgga | tccgcaacgg | tgccctgctg | 1560 |
| cgggtctatg | tgccgcgctc | gagcctgccg | ggcttctacc | gcaccggcct | gaccctggcc | 1620 |
| gcgccggagg | cggcgggcga | ggtcgaacgg | ctgatcggcc | atccgctgcc | gctgcgcctg | 1680 |
| gacgccatca | ccgccccga | ggaggaaggc | gggcgcgtga | ccattctcgg | ctggccgctg | 1740 |
| gccgagcgca | ccgtggtgat | ccctcggcg | atccccaccg | accgcgcaa | cgtcggcggc | 1800 |

-continued

```
gacctcgacc cgtccagcat ccccgacaag gaacaggcga tcagcgccct gccggactac    1860
gccagccagc ccggcaaacc gccgcgcgag gacctgaagg atcagaacgc gacctcagcc    1920
gttaccgagt attacctgaa tcacggcgaa tggcccggca caacacttc tgccggcgtg    1980 gcaacctcct ctgaaatcaa aggaggtgga caccaccacc accaccacta aaagctt      2037
```

<210> SEQ ID NO 46
<211> LENGTH: 674
<212> TYPE: PRT
<213> ORGANISM: Artificial Sequence
<220> FEATURE:
<223> OTHER INFORMATION: rEPA4573

<400> SEQUENCE: 46

Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
    210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Pro Thr Val Ile Ser His Arg Leu His Phe Pro Glu Gly
            260                 265                 270

Gly Ser Leu Ala Ala Leu Thr Ala His Gln Ala Cys His Leu Pro Leu
        275                 280                 285

Glu Thr Phe Thr Arg His Arg Gln Pro Arg Gly Trp Glu Gln Leu Glu
    290                 295                 300

Gln Cys Gly Tyr Pro Val Gln Arg Leu Val Ala Leu Tyr Leu Ala Ala
305                 310                 315                 320

Arg Leu Ser Trp Asn Gln Val Asp Gln Val Ile Gly Asn Ala Leu Ala 325                 330                 335
Ser Pro Gly Ser Gly Gly Asp Leu Gly Glu Ala Ile Arg Glu Gln Pro
                340                 345                 350
Glu Gln Ala Arg Leu Ala Leu Thr Leu Ala Ala Ala Glu Ser Glu Arg
                355                 360                 365
Phe Val Arg Gln Gly Thr Gly Asn Asp Glu Ala Gly Ala Ala Ser Ala
            370                 375                 380
Asp Val Val Ser Leu Thr Cys Pro Val Ala Ala Gly Glu Cys Ala Gly
385                 390                 395                 400
Pro Ala Asp Ser Gly Asp Ala Leu Leu Glu Arg Asn Tyr Pro Thr Gly
                405                 410                 415
Ala Glu Phe Leu Gly Asp Gly Asp Ile Ser Phe Ser Thr Arg Gly
                420                 425                 430
Thr Gln Asn Trp Thr Val Glu Arg Leu Leu Gln Ala His Arg Gln Leu
                435                 440                 445
Glu Glu Arg Gly Tyr Val Phe Val Gly Tyr His Gly Thr Phe Leu Glu
                450                 455                 460
Ala Ala Gln Ser Ile Val Phe Gly Gly Val Arg Ala Arg Ser Gln Asp
465                 470                 475                 480
Leu Asp Ala Ile Trp Arg Gly Phe Tyr Ile Ala Gly Asp Pro Ala Leu
                485                 490                 495
Ala Tyr Gly Tyr Ala Gln Asp Gln Glu Pro Asp Ala Arg Gly Arg Ile
                500                 505                 510
Arg Asn Gly Ala Leu Leu Arg Val Tyr Val Pro Arg Ser Ser Leu Pro
                515                 520                 525
Gly Phe Tyr Arg Thr Gly Leu Thr Leu Ala Ala Pro Glu Ala Ala Gly
                530                 535                 540
Glu Val Glu Arg Leu Ile Gly His Pro Leu Pro Leu Arg Leu Asp Ala
545                 550                 555                 560
Ile Thr Gly Pro Glu Glu Gly Gly Arg Val Thr Ile Leu Gly Trp
                565                 570                 575
Pro Leu Ala Glu Arg Thr Val Val Ile Pro Ser Ala Ile Pro Thr Asp
                580                 585                 590
Pro Arg Asn Val Gly Gly Asp Leu Asp Pro Ser Ser Ile Pro Asp Lys
                595                 600                 605
Glu Gln Ala Ile Ser Ala Leu Pro Asp Tyr Ala Ser Gln Pro Gly Lys
                610                 615                 620
Pro Pro Arg Glu Asp Leu Lys Asp Gln Asn Ala Thr Ser Ala Val Thr
625                 630                 635                 640
Glu Tyr Tyr Leu Asn His Gly Glu Trp Pro Gly Asn Asn Thr Ser Ala
                645                 650                 655
Gly Val Ala Thr Ser Ser Glu Ile Lys Gly Gly His His His
                660                 665                 670
His His

<210> SEQ ID NO 47
<211> LENGTH: 2013
<212> TYPE: DNA
<213> ORGANISM: Artificial Sequence
<220> FEATURE:
<223> OTHER INFORMATION: rEPA5573N

<400> SEQUENCE: 47
gaattcatga aaaagatttg gctggcgctg gctggtttag ttttagcgtt tagcgcatcg      60

```
gcggccgagg gcgaatggcc cggcaacaac acttctgccg gcgtggcaac ctcctctgaa      120
atcaaaacta gtgaagcctt cgacctctgg aacgaatgcg ccaaagcctg cgtgctcgac      180
ctcaaggacg gcgtgcgttc cagccgcatg agcgtcgacc cggccatcgc cgacaccaac      240
ggccagggcg tgctgcacta ctccatggtc ctggagggcg gcaacgacgc gctcaagctg      300
gccatcgaca acgccctcag catcaccagc gacggcctga ccatccgcct cgaaggcggc      360
gtcgagccga caagccggt gcgctacagc tacacgcgcc aggcgcgcgg cagttggtcg       420
ctgaactggc tggtaccgat cggccacgag aagccctcga acatcaaggt gttcatccac      480
gaactgaacg ccggtaacca gctcagccac atgtcgccga tctacaccat cgagatgggc      540
gacgagttgc tggcgaagct ggcgcgcgat gccaccttct tcgtcagggc gcacgagagc      600
aacgagatgc agccgacgct cgccatcagc catgccgggg tcagcgtggt catggcccag      660
gcccagccgc gccgggaaaa gcgctggagc gaatgggcca gcgcaaggt gttgtgcctg       720 ctcgacccgc tggacggggt ctacaactac ctcgcccagc agcgctgcaa cctcgacgat      780
acctgggaag gcaagatcta ccgggtgctc gccggcaacc cggcgaagca tgacctggac      840
atcaagccca cggtcatcag tcatcgcctg cacttccccg agggcggcag cctggccgcg      900
ctgaccgcgc accaggcttg ccacctgccg ctggagactt tcacccgtca tcgccagccg      960
cgcggctggg aacaactgga gcagtgcggc tatccggtgc agcggctggt cgccctctac     1020
ctggcggcgc ggctgtcgtg gaaccaggtc gaccaggtga tcgcaacgc cctgccagc      1080 cccggcagcg gcggcgacct gggcgaagcg atccgcgagc agccggagca ggcccgtctg     1140
gccctgaccc tggccgccgc cgagagcgag cgcttcgtcc ggcagggcac cggcaacgac     1200
gaggccggcg cggccagcgc cgacgtggtg agcctgacct gcccggtcgc cgccggtgaa     1260
tgcgcgggcc cggcggacag cggcgacgcc tgctgagc gcaactatcc cactggcgcg       1320
gagttcctcg gcgacggcgg cgacatcagc ttcagcaccc gcggcacgca gaactggacg     1380
gtggagcggc tgctccaggc gcaccgccaa ctggaggagc gcggctatgt gttcgtcggc     1440
taccacggca ccttcctcga agcggcgcaa agcatcgtct tcggcggggt gcgcgcgcgc     1500
agccaggacc tcgacgcgat ctggcgcggt ttctatatcg ccggcgatcc ggcgctggcc     1560
tacggctacg cccaggacca ggaacccgac gcgcgcggcc ggatccgcaa cggtgccctg     1620
ctgcgggtct atgtgccgcg ctcgagcctg ccgggcttct accgcaccgg cctgaccctg     1680
gccgcgccgg aggcggcggg cgaggtcgaa cggctgatcg gccatccgct gccgctgcgc     1740
ctggacgcca tcaccggccc cgaggaggaa ggcgggcgcg tgaccattct cggctggccg     1800
ctggccgagc gcaccgtggt gattccctcg gcgatcccca ccgacccgcg caacgtcggc     1860
ggcgacctcg acccgtccag catccccgac aaggaacagg cgatcagcgc cctgccggac     1920
tacgccagcc agcccggcaa accgccgcgc gaggacctga aggatcagaa cgcgaccgga     1980
ggtggacacc accaccacca ccactaaaag ctt                                  2013
```

<210> SEQ ID NO 48
<211> LENGTH: 666
<212> TYPE: PRT
<213> ORGANISM: Artificial Sequence
<220> FEATURE:
<223> OTHER INFORMATION: rEPA5573N

<400> SEQUENCE: 48

```
Met Lys Lys Ile Trp Leu Ala Leu Ala Gly Leu Val Leu Ala Phe Ser
1               5                   10                  15
```

```
Ala Ser Ala Ala Glu Gly Glu Trp Pro Gly Asn Asn Thr Ser Ala Gly
             20                  25                  30

Val Ala Thr Ser Ser Glu Ile Lys Thr Ser Glu Ala Phe Asp Leu Trp
         35                  40                  45

Asn Glu Cys Ala Lys Ala Cys Val Leu Asp Leu Lys Asp Gly Val Arg
 50                  55                  60

Ser Ser Arg Met Ser Val Asp Pro Ala Ile Ala Asp Thr Asn Gly Gln
 65                  70                  75                  80

Gly Val Leu His Tyr Ser Met Val Leu Glu Gly Asn Asp Ala Leu
                 85                  90                  95

Lys Leu Ala Ile Asp Asn Ala Leu Ser Ile Thr Ser Asp Gly Leu Thr
                100                 105                 110

Ile Arg Leu Glu Gly Gly Val Glu Pro Asn Lys Pro Val Arg Tyr Ser
        115                 120                 125

Tyr Thr Arg Gln Ala Arg Gly Ser Trp Ser Leu Asn Trp Leu Val Pro
    130                 135                 140

Ile Gly His Glu Lys Pro Ser Asn Ile Lys Val Phe Ile His Glu Leu
145                 150                 155                 160

Asn Ala Gly Asn Gln Leu Ser His Met Ser Pro Ile Tyr Thr Ile Glu
                165                 170                 175

Met Gly Asp Glu Leu Leu Ala Lys Leu Ala Arg Asp Ala Thr Phe Phe
            180                 185                 190

Val Arg Ala His Glu Ser Asn Glu Met Gln Pro Thr Leu Ala Ile Ser
        195                 200                 205

His Ala Gly Val Ser Val Met Ala Gln Ala Gln Pro Arg Arg Glu
210                 215                 220

Lys Arg Trp Ser Glu Trp Ala Ser Gly Lys Val Leu Cys Leu Leu Asp
225                 230                 235                 240

Pro Leu Asp Gly Val Tyr Asn Tyr Leu Ala Gln Gln Arg Cys Asn Leu
                245                 250                 255

Asp Asp Thr Trp Glu Gly Lys Ile Tyr Arg Val Leu Ala Gly Asn Pro
            260                 265                 270

Ala Lys His Asp Leu Asp Ile Lys Pro Thr Val Ile Ser His Arg Leu
        275                 280                 285

His Phe Pro Glu Gly Gly Ser Leu Ala Ala Leu Thr Ala His Gln Ala
    290                 295                 300

Cys His Leu Pro Leu Glu Thr Phe Thr Arg His Arg Gln Pro Arg Gly
305                 310                 315                 320

Trp Glu Gln Leu Glu Gln Cys Gly Tyr Pro Val Gln Arg Leu Val Ala
                325                 330                 335

Leu Tyr Leu Ala Ala Arg Leu Ser Trp Asn Gln Val Asp Gln Val Ile
            340                 345                 350

Gly Asn Ala Leu Ala Ser Pro Gly Gly Asp Leu Gly Glu Ala
        355                 360                 365

Ile Arg Glu Gln Pro Glu Gln Ala Arg Leu Ala Leu Thr Leu Ala Ala
    370                 375                 380

Ala Glu Ser Glu Arg Phe Val Arg Gln Gly Thr Gly Asn Asp Glu Ala
385                 390                 395                 400

Gly Ala Ala Ser Ala Asp Val Val Ser Leu Thr Cys Pro Val Ala Ala
                405                 410                 415

Gly Glu Cys Ala Gly Pro Ala Asp Ser Gly Asp Ala Leu Leu Glu Arg
            420                 425                 430

Asn Tyr Pro Thr Gly Ala Glu Phe Leu Gly Asp Gly Gly Asp Ile Ser
```

```
                435                 440                 445
Phe Ser Thr Arg Gly Thr Gln Asn Trp Thr Val Glu Arg Leu Leu Gln
    450                 455                 460

Ala His Arg Gln Leu Glu Glu Arg Gly Tyr Val Phe Val Gly Tyr His
465                 470                 475                 480

Gly Thr Phe Leu Glu Ala Ala Gln Ser Ile Val Phe Gly Gly Val Arg
                485                 490                 495

Ala Arg Ser Gln Asp Leu Asp Ala Ile Trp Arg Gly Phe Tyr Ile Ala
            500                 505                 510

Gly Asp Pro Ala Leu Ala Tyr Gly Tyr Ala Gln Asp Gln Glu Pro Asp
        515                 520                 525

Ala Arg Gly Arg Ile Arg Asn Gly Ala Leu Leu Arg Val Tyr Val Pro
    530                 535                 540

Arg Ser Ser Leu Pro Gly Phe Tyr Arg Thr Gly Leu Thr Leu Ala Ala
545                 550                 555                 560

Pro Glu Ala Ala Gly Glu Val Glu Arg Leu Ile Gly His Pro Leu Pro
                565                 570                 575

Leu Arg Leu Asp Ala Ile Thr Gly Pro Glu Glu Gly Gly Arg Val
            580                 585                 590

Thr Ile Leu Gly Trp Pro Leu Ala Glu Arg Thr Val Val Ile Pro Ser
        595                 600                 605

Ala Ile Pro Thr Asp Pro Arg Asn Val Gly Gly Asp Leu Asp Pro Ser
    610                 615                 620

Ser Ile Pro Asp Lys Glu Gln Ala Ile Ser Ala Leu Pro Asp Tyr Ala
625                 630                 635                 640

Ser Gln Pro Gly Lys Pro Pro Arg Glu Asp Leu Lys Asp Gln Asn Ala
                645                 650                 655

Thr Gly Gly Gly His His His His His
            660                 665

<210> SEQ ID NO 49
<211> LENGTH: 2001
<212> TYPE: DNA
<213> ORGANISM: Artificial Sequence
<220> FEATURE:
<223> OTHER INFORMATION: rEPA5569N

<400> SEQUENCE: 49
gaattcatga aaaagatttg ctggcgctg gctggtttag ttttagcgtt tagcgcatcg      60
gcggccgagg cgaatggcc cggcaacaac acttctgccg gcgtggcaac ctccactagt     120
gaagccttcg acctctggaa cgaatgcgcc aaagcctgcg tgctcgacct caaggacggc    180
gtgcgttcca gccgcatgag cgtcgacccg gccatcgccg acaccaacgg ccagggcgtg    240
ctgcactact ccatggtcct ggagggcggc aacgacgcgc tcaagctggc catcgacaac    300
gccctcagca tcaccagcga cggcctgacc atccgcctcg aaggcggcgt cgagccgaac    360
aagccggtgc gctacagcta cacgcgccag gcgcgcggca ttggtcgct gaactggctg    420 gtaccgatcg ccacgagaa gccctcgaac atcaaggtgt tcatccacga actgaacgcc    480
ggtaaccagc tcagccacat gtcgccgatc tacaccatcg agatgggcga cgagttgctg    540
gcgaagctgg cgcgcgatgc caccttcttc gtcagggcgc acgagagcaa cgagatgcag    600
ccgacgctcg ccatcagcca tgccggggtc agcgtggtca tggccaggc ccagccgcgc    660 cgggaaaagc gctggagcga atgggccagc ggcaaggtgt tgtgcctgct cgaccgctg    720 gacggggtct acaactacct cgcccagcag cgctgcaacc tcgacgatac ctgggaaggc    780
```

```
aagatctacc gggtgctcgc cggcaacccg gcgaagcatg acctggacat caagcccacg   840
gtcatcagtc atcgcctgca cttccccgag ggcggcagcc tggccgcgct gaccgcgcac   900
caggcttgcc acctgccgct ggagactttc acccgtcatc gccagccgcg cggctgggaa   960
caactggagc agtgcggcta tccggtgcag cggctggtcg ccctctacct ggcggcgcgg  1020
ctgtcgtgga accaggtcga ccaggtgatc ggcaacgccc tggccagccc cggcagcggc  1080
ggcgacctgg cgaagcgat ccgcgagcag ccggagcagg cccgtctggc cctgaccctg  1140
gccgccgccg agagcgagcg cttcgtccgg cagggcaccg gcaacgacga ggccggcgcg  1200
gccagcgccg acgtggtgag cctgacctgc ccggtcgccg ccgtgaatg cgcgggcccg  1260 gcggacagcg gcgacgccct gctggagcgc aactatccca ctggcgcgga gttcctcggc  1320
gacgcgggcg acatcagctt cagcacccgc ggcacgcaga actggacggt ggagcggctg  1380
ctccaggcgc accgccaact ggaggagcgc ggctatgtgt cgtcggcta ccacggcacc  1440 ttcctcgaag cggcgcaaag catcgtcttc ggcggggtgc gcgcgcgcag ccaggacctc  1500
gacgcgatct ggcgcggttt ctatatcgcc ggcgatccgg cgctggccta cggctacgcc  1560
caggaccagg aacccgacgc gcgcggccgg atccgcaacg tgccctgct gcgggtctat  1620 gtgccgcgct cgagcctgcc gggcttctac cgcaccggcc tgaccctggc cgcgccggag  1680
gcggcgggcg aggtcgaacg gctgatcggc catccgctgc cgctgcgcct ggacgccatc  1740
accggccccg aggaggaagg cgggcgcgtg accattctcg gctggccgct ggccgagcgc  1800
accgtggtga ttccctcggc gatccccacc gacccgcgca acgtcggcgg cgacctcgac  1860
ccgtccagca tccccgacaa ggaacaggcg atcagcgccc tgccggacta cgccagccag  1920
cccggcaaac cgccgcgcga ggacctgaag gatcagaacg cgaccggagg tggacaccac  1980
caccaccacc actaaaagct t                                             2001
```

<210> SEQ ID NO 50
<211> LENGTH: 662
<212> TYPE: PRT
<213> ORGANISM: Artificial Sequence
<220> FEATURE:
<223> OTHER INFORMATION: rEPA5569N

<400> SEQUENCE: 50

```
Met Lys Lys Ile Trp Leu Ala Leu Ala Gly Leu Val Leu Ala Phe Ser
1               5                   10                  15

Ala Ser Ala Ala Glu Gly Glu Trp Pro Gly Asn Asn Thr Ser Ala Gly
            20                  25                  30

Val Ala Thr Ser Thr Ser Glu Ala Phe Asp Leu Trp Asn Glu Cys Ala
        35                  40                  45

Lys Ala Cys Val Leu Asp Leu Lys Asp Gly Val Arg Ser Ser Arg Met
    50                  55                  60

Ser Val Asp Pro Ala Ile Ala Asp Thr Asn Gly Gln Gly Val Leu His
65                  70                  75                  80

Tyr Ser Met Val Leu Glu Gly Gly Asn Asp Ala Leu Lys Leu Ala Ile
                85                  90                  95

Asp Asn Ala Leu Ser Ile Thr Ser Asp Gly Leu Thr Ile Arg Leu Glu
            100                 105                 110

Gly Gly Val Glu Pro Asn Lys Pro Val Arg Tyr Ser Tyr Thr Arg Gln
        115                 120                 125

Ala Arg Gly Ser Trp Ser Leu Asn Trp Leu Val Pro Ile Gly His Glu
    130                 135                 140
```

```
Lys Pro Ser Asn Ile Lys Val Phe Ile His Glu Leu Asn Ala Gly Asn
145                 150                 155                 160

Gln Leu Ser His Met Ser Pro Ile Tyr Thr Ile Glu Met Gly Asp Glu
            165                 170                 175

Leu Leu Ala Lys Leu Ala Arg Asp Ala Thr Phe Phe Val Arg Ala His
        180                 185                 190

Glu Ser Asn Glu Met Gln Pro Thr Leu Ala Ile Ser His Ala Gly Val
    195                 200                 205

Ser Val Val Met Ala Gln Ala Gln Pro Arg Arg Glu Lys Arg Trp Ser
210                 215                 220

Glu Trp Ala Ser Gly Lys Val Leu Cys Leu Leu Asp Pro Leu Asp Gly
225                 230                 235                 240

Val Tyr Asn Tyr Leu Ala Gln Gln Arg Cys Asn Leu Asp Asp Thr Trp
                245                 250                 255

Glu Gly Lys Ile Tyr Arg Val Leu Ala Gly Asn Pro Ala Lys His Asp
            260                 265                 270

Leu Asp Ile Lys Pro Thr Val Ile Ser His Arg Leu His Phe Pro Glu
        275                 280                 285

Gly Gly Ser Leu Ala Ala Leu Thr Ala His Gln Ala Cys His Leu Pro
    290                 295                 300

Leu Glu Thr Phe Thr Arg His Arg Gln Pro Arg Gly Trp Glu Gln Leu
305                 310                 315                 320

Glu Gln Cys Gly Tyr Pro Val Gln Arg Leu Val Ala Leu Tyr Leu Ala
                325                 330                 335

Ala Arg Leu Ser Trp Asn Gln Val Asp Gln Val Ile Gly Asn Ala Leu
            340                 345                 350

Ala Ser Pro Gly Ser Gly Gly Asp Leu Gly Glu Ala Ile Arg Glu Gln
        355                 360                 365

Pro Glu Gln Ala Arg Leu Ala Leu Thr Leu Ala Ala Ala Glu Ser Glu
    370                 375                 380

Arg Phe Val Arg Gln Gly Thr Gly Asn Asp Glu Ala Gly Ala Ala Ser
385                 390                 395                 400

Ala Asp Val Val Ser Leu Thr Cys Pro Val Ala Ala Gly Glu Cys Ala
                405                 410                 415

Gly Pro Ala Asp Ser Gly Asp Ala Leu Leu Glu Arg Asn Tyr Pro Thr
            420                 425                 430

Gly Ala Glu Phe Leu Gly Asp Gly Asp Ile Ser Phe Ser Thr Arg
        435                 440                 445

Gly Thr Gln Asn Trp Thr Val Glu Arg Leu Leu Gln Ala His Arg Gln
    450                 455                 460

Leu Glu Glu Arg Gly Tyr Val Phe Val Gly Tyr His Gly Thr Phe Leu
465                 470                 475                 480

Glu Ala Ala Gln Ser Ile Val Phe Gly Gly Val Arg Ala Arg Ser Gln
                485                 490                 495

Asp Leu Asp Ala Ile Trp Arg Gly Phe Tyr Ile Ala Gly Asp Pro Ala
            500                 505                 510

Leu Ala Tyr Gly Tyr Ala Gln Asp Gln Glu Pro Asp Ala Arg Gly Arg
        515                 520                 525

Ile Arg Asn Gly Ala Leu Leu Arg Val Tyr Val Pro Arg Ser Ser Leu
    530                 535                 540

Pro Gly Phe Tyr Arg Thr Gly Leu Thr Leu Ala Ala Pro Glu Ala Ala
545                 550                 555                 560
```

Gly Glu Val Glu Arg Leu Ile Gly His Pro Leu Pro Leu Arg Leu Asp
            565                 570                 575

Ala Ile Thr Gly Pro Glu Glu Gly Gly Arg Val Thr Ile Leu Gly
        580                 585                 590

Trp Pro Leu Ala Glu Arg Thr Val Val Ile Pro Ser Ala Ile Pro Thr
            595                 600                 605

Asp Pro Arg Asn Val Gly Gly Asp Leu Asp Pro Ser Ser Ile Pro Asp
        610                 615                 620

Lys Glu Gln Ala Ile Ser Ala Leu Pro Asp Tyr Ala Ser Gln Pro Gly
625                 630                 635                 640

Lys Pro Pro Arg Glu Asp Leu Lys Asp Gln Asn Ala Thr Gly Gly Gly
            645                 650                 655

His His His His His His
        660

<210> SEQ ID NO 51
<211> LENGTH: 1992
<212> TYPE: DNA
<213> ORGANISM: Artificial Sequence
<220> FEATURE:
<223> OTHER INFORMATION: rEPA5566N

<400> SEQUENCE: 51

| | | | |
|---|---|---|---|
| gaattcatga aaaagatttg gctggcgctg gctggtttag ttttagcgtt tagcgcatcg | | | 60 |
| gcggccgagg gcgaatggcc cggcaacaac acttctgccg gcgtgactag tgaagccttc | | | 120 |
| gacctctgga cgaatgcgc caaagcctgc gtgctcgacc tcaaggacgg cgtgcgttcc | | | 180 |
| agccgcatga gcgtcgaccc ggccatcgcc gacaccaacg gccagggcgt gctgcactac | | | 240 |
| tccatggtcc tggagggcgg caacgacgcg ctcaagctgg ccatcgacaa cgccctcagc | | | 300 |
| atcaccagcg acggcctgac catccgcctc gaaggcggcg tcgagccgaa caagccggtg | | | 360 |
| cgctacagct acacgcgcca ggcgcgcggc agttggtcgc tgaactggct ggtaccgatc | | | 420 |
| ggccacgaga agccctcgaa catcaaggtg ttcatccacg aactgaacgc cggtaaccag | | | 480 |
| ctcagccaca tgtcgccgat ctacaccatc gagatgggcg acgagttgct ggcgaagctg | | | 540 |
| gcgcgcgatg ccaccttctt cgtcagggcg cacgagagca cgagatgca gccgacgctc | | | 600 |
| gccatcagcc atgccggggt cagcgtggtc atggcccagg cccagccgcg ccgggaaaag | | | 660 |
| cgctggagcg aatgggccag cggcaaggtg ttgtgcctgc tcgacccgct ggacggggtc | | | 720 |
| tacaactacc tcgcccagca gcgctgcaac ctcgacgata cctgggaagg caagatctac | | | 780 |
| cgggtgctcg ccggcaaccc ggcgaagcat gacctgaca tcaagcccac ggtcatcagt | | | 840 |
| catcgcctgc acttccccga gggcggcagc ctggccgcgc tgaccgcgca ccaggcttgc | | | 900 |
| cacctgccgc tggagacttt cacccgtcat cgccagccgc gcggctggga caactggag | | | 960 |
| cagtgcggct atccggtgca gcggctggtc gccctctacc tggcggcgcg gctgtcgtgg | | | 1020 |
| aaccaggtcg accaggtgat cggcaacgcc ctggccagcc ccggcagcgg cggcgacctg | | | 1080 |
| ggcgaagcga tccgcgagca gccggagcag gcccgtctgg ccctgaccct ggccgccgcc | | | 1140 |
| gagagcgagc gcttcgtccg gcagggcacc ggcaacgacg aggccggcgc ggccagcgcc | | | 1200 |
| gacgtggtga gcctgacctg cccggtcgcc gccgtgaat gcgcgggccc ggcggacagc | | | 1260 |
| ggcgacgccc tgctggagcg caactatccc actggcgcgg agttcctcgg cgacggcggc | | | 1320 |
| gacatcagct tcagcacccg cggcacgcag aactggacgg tggagcggct gctccaggcg | | | 1380 |
| caccgccaac tggaggagcg cggctatgtg ttcgtcggct accacggcac cttcctcgaa | | | 1440 |

-continued

```
gcggcgcaaa gcatcgtctt cggcggggtg cgcgcgcgca gccaggacct cgacgcgatc      1500
tggcgcggtt tctatatcgc cggcgatccg gcgctggcct acggctacgc ccaggaccag      1560
gaacccgacg cgcgcggccg gatccgcaac ggtgccctgc tgcgggtcta tgtgccgcgc      1620
tcgagcctgc cgggcttcta ccgcaccggc ctgaccctgg ccgcgccgga ggcggcgggc      1680
gaggtcgaac ggctgatcgg ccatccgctg ccgctgcgcc tggacgccat caccggcccc      1740
gaggaggaag cgggcgcgt gaccattctc ggctggccgc tggccgagcg caccgtggtg       1800
attccctcgg cgatccccac cgacccgcgc aacgtcggcg cgacctcga cccgtccagc       1860 atccccgaca aggaacaggc gatcagcgcc ctgccggact acgccagcca gcccggcaaa      1920
ccgccgcgcg aggacctgaa ggatcagaac gcgaccggag gtggacacca ccaccaccac      1980
cactaaaagc tt                                                          1992
```

<210> SEQ ID NO 52
<211> LENGTH: 659
<212> TYPE: PRT
<213> ORGANISM: Artificial Sequence
<220> FEATURE:
<223> OTHER INFORMATION: rEPA5566N

<400> SEQUENCE: 52

```
Met Lys Lys Ile Trp Leu Ala Leu Ala Gly Leu Val Leu Ala Phe Ser
1               5                   10                  15

Ala Ser Ala Ala Glu Gly Glu Trp Pro Gly Asn Asn Thr Ser Ala Gly
                20                  25                  30

Val Thr Ser Glu Ala Phe Asp Leu Trp Asn Glu Cys Ala Lys Ala Cys
        35                  40                  45

Val Leu Asp Leu Lys Asp Gly Val Arg Ser Ser Arg Met Ser Val Asp
    50                  55                  60

Pro Ala Ile Ala Asp Thr Asn Gly Gln Gly Val Leu His Tyr Ser Met
65                  70                  75                  80

Val Leu Glu Gly Gly Asn Asp Ala Leu Lys Leu Ala Ile Asp Asn Ala
                85                  90                  95

Leu Ser Ile Thr Ser Asp Gly Leu Thr Ile Arg Leu Glu Gly Gly Val
            100                 105                 110

Glu Pro Asn Lys Pro Val Arg Tyr Ser Tyr Thr Arg Gln Ala Arg Gly
        115                 120                 125

Ser Trp Ser Leu Asn Trp Leu Val Pro Ile Gly His Glu Lys Pro Ser
    130                 135                 140

Asn Ile Lys Val Phe Ile His Glu Leu Asn Ala Gly Asn Gln Leu Ser
145                 150                 155                 160

His Met Ser Pro Ile Tyr Thr Ile Glu Met Gly Asp Glu Leu Leu Ala
                165                 170                 175

Lys Leu Ala Arg Asp Ala Thr Phe Phe Val Arg Ala His Glu Ser Asn
            180                 185                 190

Glu Met Gln Pro Thr Leu Ala Ile Ser His Ala Gly Val Ser Val Val
        195                 200                 205

Met Ala Gln Ala Gln Pro Arg Arg Glu Lys Arg Trp Ser Glu Trp Ala
    210                 215                 220

Ser Gly Lys Val Leu Cys Leu Leu Asp Pro Leu Asp Gly Val Tyr Asn
225                 230                 235                 240

Tyr Leu Ala Gln Gln Arg Cys Asn Leu Asp Asp Thr Trp Glu Gly Lys
                245                 250                 255

Ile Tyr Arg Val Leu Ala Gly Asn Pro Ala Lys His Asp Leu Asp Ile
```

```
                  260                 265                 270
Lys Pro Thr Val Ile Ser His Arg Leu His Phe Pro Glu Gly Gly Ser
                  275                 280                 285

Leu Ala Ala Leu Thr Ala His Gln Ala Cys His Leu Pro Leu Glu Thr
                  290                 295                 300

Phe Thr Arg His Arg Gln Pro Arg Gly Trp Glu Gln Leu Glu Gln Cys
305                 310                 315                 320

Gly Tyr Pro Val Gln Arg Leu Val Ala Leu Tyr Leu Ala Ala Arg Leu
                  325                 330                 335

Ser Trp Asn Gln Val Asp Gln Val Ile Gly Asn Ala Leu Ala Ser Pro
                  340                 345                 350

Gly Ser Gly Gly Asp Leu Gly Glu Ala Ile Arg Glu Gln Pro Glu Gln
                  355                 360                 365

Ala Arg Leu Ala Leu Thr Leu Ala Ala Ala Glu Ser Glu Arg Phe Val
                  370                 375                 380

Arg Gln Gly Thr Gly Asn Asp Glu Ala Gly Ala Ala Ser Ala Asp Val
385                 390                 395                 400

Val Ser Leu Thr Cys Pro Val Ala Ala Gly Glu Cys Ala Gly Pro Ala
                  405                 410                 415

Asp Ser Gly Asp Ala Leu Leu Glu Arg Asn Tyr Pro Thr Gly Ala Glu
                  420                 425                 430

Phe Leu Gly Asp Gly Gly Asp Ile Ser Phe Ser Thr Arg Gly Thr Gln
                  435                 440                 445

Asn Trp Thr Val Glu Arg Leu Leu Gln Ala His Arg Gln Leu Glu Glu
                  450                 455                 460

Arg Gly Tyr Val Phe Val Gly Tyr His Gly Thr Phe Leu Glu Ala Ala
465                 470                 475                 480

Gln Ser Ile Val Phe Gly Gly Val Arg Ala Arg Ser Gln Asp Leu Asp
                  485                 490                 495

Ala Ile Trp Arg Gly Phe Tyr Ile Ala Gly Asp Pro Ala Leu Ala Tyr
                  500                 505                 510

Gly Tyr Ala Gln Asp Gln Glu Pro Asp Ala Arg Gly Arg Ile Arg Asn
                  515                 520                 525

Gly Ala Leu Leu Arg Val Tyr Val Pro Arg Ser Ser Leu Pro Gly Phe
                  530                 535                 540

Tyr Arg Thr Gly Leu Thr Leu Ala Ala Pro Glu Ala Ala Gly Glu Val
545                 550                 555                 560

Glu Arg Leu Ile Gly His Pro Leu Pro Leu Arg Leu Asp Ala Ile Thr
                  565                 570                 575

Gly Pro Glu Glu Glu Gly Gly Arg Val Thr Ile Leu Gly Trp Pro Leu
                  580                 585                 590

Ala Glu Arg Thr Val Val Ile Pro Ser Ala Ile Pro Thr Asp Pro Arg
                  595                 600                 605

Asn Val Gly Gly Asp Leu Asp Pro Ser Ile Pro Asp Lys Glu Gln
                  610                 615                 620

Ala Ile Ser Ala Leu Pro Asp Tyr Ala Ser Gln Pro Gly Lys Pro Pro
625                 630                 635                 640

Arg Glu Asp Leu Lys Asp Gln Asn Ala Thr Gly Gly His His
                  645                 650                 655

His His His

<210> SEQ ID NO 53
<211> LENGTH: 1983
```

<212> TYPE: DNA
<213> ORGANISM: Artificial Sequence
<220> FEATURE:
<223> OTHER INFORMATION: rEPA5866N

<400> SEQUENCE: 53

```
gaattcatga aaagatttg gctggcgctg gctggtttag ttttagcgtt tagcgcatcg      60
gcggccgagc ccggcaacaa cacttctgcc ggcgtgacta gtgaagcctt cgacctctgg    120
aacgaatgcg ccaaagcctg cgtgctcgac ctcaaggacg cgtgcgttc cagccgcatg    180
agcgtcgacc cggccatcgc cgacaccaac ggccagggcg tgctgcacta ctccatggtc    240
ctggagggcg gcaacgacgc gctcaagctg gccatcgaca cgccctcag catcaccagc    300
gacggcctga ccatccgcct cgaaggcggc gtcgagccga caagccggt gcgctacagc    360
tacacgcgcc aggcgcgcgg cagttggtcg ctgaactggc tggtaccgat cggccacgag    420
aagccctcga acatcaaggt gttcatccac gaactgaacg ccggtaacca gctcagccac    480
atgtcgccga tctacaccat cgagatgggc gacgagttgc tggcgaagct ggcgcgcgat    540
gccaccttct tcgtcagggc gcacgagagc aacgagatgc agccgacgct cgccatcagc    600
catgccgggg tcagcgtggt catggcccag gcccagccgc gccgggaaaa gcgctggagc    660
gaatgggcca gcggcaaggt gttgtgcctg ctcgacccgc tggacggggt ctacaactac    720
ctcgcccagc agcgctgcaa cctcgacgat acctgggaag gcaagatcta ccgggtgctc    780
gccggcaacc cggcgaagca tgacctggac atcaagccca cggtcatcag tcatcgcctg    840
cacttccccg agggcggcag cctggccgcg ctgaccgcgc accaggcttg ccacctgccg    900
ctggagactt tcacccgtca tcgccagccg cgcggctggg aacaactgga gcagtgcggc    960
tatccggtgc agcggctggt cgccctctac ctggcggcgc ggctgtcgtg gaaccaggtc   1020
gaccaggtga tcggcaacgc cctggccagc cccggcagcg gcggcgacct gggcgaagcg   1080
atccgcgagc agccggagca ggcccgtctg gccctgaccc tggccgccgc cgagagcgag   1140
cgcttcgtcc ggcagggcac cggcaacgac gaggccggcg cggccagcgc cgacgtggtg   1200
agcctgacct gcccggtcgc cgccggtgaa tgcgcgggcc cggcggacag cggcgacgcc   1260
ctgctggagc gcaactatcc cactggcgcg gagttcctcg gcgacggcgg cgacatcagc   1320
ttcagcaccc gcggcacgca gaactggacg gtggagcggc tgctccaggc gcaccgccaa   1380
ctggaggagc gcggctatgt gttcgtcggc taccacggca ccttcctcga gcggcgcaa    1440
agcatcgtct tcggcggggt gcgcgcgcgc agccaggacc tcgacgcgat ctggcgcggt   1500
ttctatatcg ccggcgatcc ggcgctggcc tacggctacg cccaggacca ggaacccgac   1560
gcgcgcggcc ggatccgcaa cggtgccctg ctgcgggtct atgtgccgcg ctcgagcctg   1620
ccgggcttct accgcaccgg cctgaccctg gccgcgccgg aggcggcggg cgaggtcgaa   1680
cggctgatcg gccatccgct gccgctgcgc ctggacgcca tcaccggccc cgaggaggaa   1740
ggcgggcgcg tgaccattct cggctggcg ctggccgagc gcaccgtggt gattccctcg   1800
gcgatcccca ccgacccgcg caacgtcggc ggcgacctcg accgtccag catccccgac   1860
aaggaacagg cgatcagcgc cctgccggac tacgccagcc agcccggcaa accgccgcgc   1920
gaggacctga aggatcagaa cgcgaccgga ggtggacacc accaccacca ccactaaaag   1980
ctt                                                                  1983
```

<210> SEQ ID NO 54
<211> LENGTH: 656
<212> TYPE: PRT

<213> ORGANISM: Artificial Sequence
<220> FEATURE:
<223> OTHER INFORMATION: rEPA5866N

<400> SEQUENCE: 54

```
Met Lys Lys Ile Trp Leu Ala Leu Ala Gly Leu Val Leu Ala Phe Ser
1               5                   10                  15

Ala Ser Ala Ala Glu Pro Gly Asn Asn Thr Ser Ala Gly Val Thr Ser
            20                  25                  30

Glu Ala Phe Asp Leu Trp Asn Glu Cys Ala Lys Ala Cys Val Leu Asp
        35                  40                  45

Leu Lys Asp Gly Val Arg Ser Ser Arg Met Ser Val Asp Pro Ala Ile
50                  55                  60

Ala Asp Thr Asn Gly Gln Gly Val Leu His Tyr Ser Met Val Leu Glu
65                  70                  75                  80

Gly Gly Asn Asp Ala Leu Lys Leu Ala Ile Asp Asn Ala Leu Ser Ile
                85                  90                  95

Thr Ser Asp Gly Leu Thr Ile Arg Leu Glu Gly Val Glu Pro Asn
            100                 105                 110

Lys Pro Val Arg Tyr Ser Tyr Thr Arg Gln Ala Arg Gly Ser Trp Ser
        115                 120                 125

Leu Asn Trp Leu Val Pro Ile Gly His Glu Lys Pro Ser Asn Ile Lys
130                 135                 140

Val Phe Ile His Glu Leu Asn Ala Gly Asn Gln Leu Ser His Met Ser
145                 150                 155                 160

Pro Ile Tyr Thr Ile Glu Met Gly Asp Glu Leu Leu Ala Lys Leu Ala
                165                 170                 175

Arg Asp Ala Thr Phe Phe Val Arg Ala His Glu Ser Asn Glu Met Gln
            180                 185                 190

Pro Thr Leu Ala Ile Ser His Ala Gly Val Ser Val Met Ala Gln
        195                 200                 205

Ala Gln Pro Arg Arg Glu Lys Arg Trp Ser Glu Trp Ala Ser Gly Lys
210                 215                 220

Val Leu Cys Leu Leu Asp Pro Leu Asp Gly Val Tyr Asn Tyr Leu Ala
225                 230                 235                 240

Gln Gln Arg Cys Asn Leu Asp Asp Thr Trp Glu Gly Lys Ile Tyr Arg
                245                 250                 255

Val Leu Ala Gly Asn Pro Ala Lys His Asp Leu Asp Ile Lys Pro Thr
            260                 265                 270

Val Ile Ser His Arg Leu His Phe Pro Glu Gly Gly Ser Leu Ala Ala
        275                 280                 285

Leu Thr Ala His Gln Ala Cys His Leu Pro Leu Glu Thr Phe Thr Arg
290                 295                 300

His Arg Gln Pro Arg Gly Trp Glu Gln Leu Glu Gln Cys Gly Tyr Pro
305                 310                 315                 320

Val Gln Arg Leu Val Ala Leu Tyr Leu Ala Ala Arg Leu Ser Trp Asn
                325                 330                 335

Gln Val Asp Gln Val Ile Gly Asn Ala Leu Ala Ser Pro Gly Ser Gly
            340                 345                 350

Gly Asp Leu Gly Glu Ala Ile Arg Glu Gln Pro Glu Gln Ala Arg Leu
        355                 360                 365

Ala Leu Thr Leu Ala Ala Ala Glu Ser Glu Arg Phe Val Arg Gln Gly
370                 375                 380

Thr Gly Asn Asp Glu Ala Gly Ala Ala Ser Ala Asp Val Val Ser Leu
```

```
                385                 390                 395                 400
        Thr Cys Pro Val Ala Ala Gly Glu Cys Ala Gly Pro Ala Asp Ser Gly
                        405                 410                 415
        Asp Ala Leu Leu Glu Arg Asn Tyr Pro Thr Gly Ala Glu Phe Leu Gly
                    420                 425                 430
        Asp Gly Asp Ile Ser Phe Ser Thr Arg Gly Thr Gln Asn Trp Thr
                435                 440                 445
        Val Glu Arg Leu Leu Gln Ala His Arg Gln Leu Glu Glu Arg Gly Tyr
        450                 455                 460
        Val Phe Val Gly Tyr His Gly Thr Phe Leu Glu Ala Ala Gln Ser Ile
        465                 470                 475                 480
        Val Phe Gly Gly Val Arg Ala Arg Ser Gln Asp Leu Asp Ala Ile Trp
                        485                 490                 495
        Arg Gly Phe Tyr Ile Ala Gly Asp Pro Ala Leu Ala Tyr Gly Tyr Ala
                        500                 505                 510
        Gln Asp Gln Glu Pro Asp Ala Arg Gly Arg Ile Arg Asn Gly Ala Leu
                    515                 520                 525
        Leu Arg Val Tyr Val Pro Arg Ser Ser Leu Pro Gly Phe Tyr Arg Thr
            530                 535                 540
        Gly Leu Thr Leu Ala Ala Pro Glu Ala Ala Gly Glu Val Glu Arg Leu
        545                 550                 555                 560
        Ile Gly His Pro Leu Pro Leu Arg Leu Asp Ala Ile Thr Gly Pro Glu
                        565                 570                 575
        Glu Glu Gly Gly Arg Val Thr Ile Leu Gly Trp Pro Leu Ala Glu Arg
                    580                 585                 590
        Thr Val Val Ile Pro Ser Ala Ile Pro Thr Asp Pro Arg Asn Val Gly
                595                 600                 605
        Gly Asp Leu Asp Pro Ser Ser Ile Pro Asp Lys Glu Gln Ala Ile Ser
                610                 615                 620
        Ala Leu Pro Asp Tyr Ala Ser Gln Pro Gly Lys Pro Pro Arg Glu Asp
        625                 630                 635                 640
        Leu Lys Asp Gln Asn Ala Thr Gly Gly Gly His His His His His His
                    645                 650                 655

<210> SEQ ID NO 55
<211> LENGTH: 612
<212> TYPE: DNA
<213> ORGANISM: Artificial Sequence
<220> FEATURE:
<223> OTHER INFORMATION: rCTB45732

<400> SEQUENCE: 55
gaattcatga agaaaatttg gctggcctta gccggcctgg ttctggcatt cagcgccagc    60
gcaaccccgc agaacatcac cgacctgtgc gccgagtacc acaacaccca aatttatacc   120
ctgaacgaca aaattttttag ctacaccgag agcctggcag gcaagcgcga gatggccatc   180
atcaccttca agaacggcgc cattttccag gtggaggtgc cgggcagcca gcacatcgac   240
agtcagaaga aggccatcga gcgcatgaag gacaccctgc gcatcgccta cctgaccgag   300
gccaaggtgg agaagctgtg cgtgtggaac aacaagaccc gcacgccat cgccgcaatc   360 agcatggcca acgaccagaa cgccaccagc gccgtgaccg agtactatct gaaccatggc   420
gagtggccgg gtaataacac cagcgccggc gtggccacaa gcagtgagat caagggcggc   480
ggatctagcg ccgtgaccga gtactatctg aaccatggcg agtggccggg taataacacc   540
agcgccggcg tggccacaag cagtgagatc aagggcggcg gatcccacca tcaccaccac   600
```
cattaaaagc tt                                                                    612

<210> SEQ ID NO 56
<211> LENGTH: 199
<212> TYPE: PRT
<213> ORGANISM: Artificial Sequence
<220> FEATURE:
<223> OTHER INFORMATION: rCTB45732

<400> SEQUENCE: 56

Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Thr Ser Ser Glu Ile Lys Gly Gly Gly Ser
145                 150                 155                 160

Ser Ala Val Thr Glu Tyr Tyr Leu Asn His Gly Glu Trp Pro Gly Asn
                165                 170                 175

Asn Thr Ser Ala Gly Val Ala Thr Ser Ser Glu Ile Lys Gly Gly Gly
            180                 185                 190

Ser His His His His His His
        195

<210> SEQ ID NO 57
<211> LENGTH: 2223
<212> TYPE: DNA
<213> ORGANISM: Artificial Sequence
<220> FEATURE:
<223> OTHER INFORMATION: rEPA4573NMC

<400> SEQUENCE: 57
gaattcatga aaaagatttg gctggcgctg gctggtttag ttttagcgtt tagcgcatcg      60
gcggccgagt cagccgttac cgagtattac ctgaatcacg gcgaatggcc cggcaacaac     120
acttctgccg gcgtggcaac ctcctctgaa atcaaaacta gtgaagcctt cgacctctgg     180
aacgaatgcg ccaaagcctg cgtgctcgac ctcaaggacg gcgtgcgttc cagccgcatg     240
agcgtcgacc cggccatcgc cgacaccaac ggccagggcg tgctgcacta ctccatggtc     300
ctggagggcg gcaacgacgc gctcaagctg gccatcgaca cgcccctcag catcaccagc     360
gacggcctga ccatccgcct cgaaggcggc gtcgagccga acaagccggt gcgctacagc     420
tacacgcgcc aggcgcgcgg cagttggtcg ctgaactggc tggtaccgat cggccacgag     480
aagccctcga acatcaaggt gttcatccac gaactgaacg ccggtaacca gctcagccac     540

```
atgtcgccga tctacaccat cgagatgggc gacgagttgc tggcgaagct ggcgcgcgat      600
gccaccttct tcgtcagggc gcacgagagc aacgagatgc agccgacgct cgccatcagc      660
catgccgggg tcagcgtggt catggcccag gcccagccgc gccgggaaaa gcgctggagc      720
gaatgggcca cgcaaggt gttgtgcctg ctcgacccgc tggacggggt ctacaactac        780
ctcgcccagc agcgctgcaa cctcgacgat acctgggaag caagatcta ccgggtgctc       840
gccggcaacc cggcgaagca tgacctggac atcaagtcag ccgttaccga gtattacctg      900
aatcacggcg aatggcccgg caacaacact tctgccggcg tggcaacctc ctctgaaatc      960
aaacatatgc ccacggtcat cagtcatcgc ctgcacttcc cgagggcgg cagcctggcc      1020
gcgctgaccg cgcaccaggc ttgccacctg ccgctggaga ctttcacccg tcatcgccag     1080
ccgcgcggct gggaacaact ggagcagtgc ggctatccgg tgcagcggct ggtcgccctc     1140
tacctggcgg cgcggctgtc gtggaaccag gtcgaccagg tgatcggcaa cgccctggcc     1200
agccccggca gcggcggcga cctgggcgaa gcgatccgcg agcagccgga gcaggcccgt     1260
ctggccctga ccctggccgc cgccgagagc gagcgcttcg tccggcaggg caccggcaac     1320
gacgaggccg gcgcggccag cgccgacgtg gtgagcctga cctgcccggt cgccgccggt     1380
gaatgcgcgg gcccggcgga cagcggcgac gccctgctgg agcgcaacta tcccactggc     1440
gcggagttcc tcggcgacgg cggcgacatc agcttcagca cccgcggcac gcagaactgg     1500
acggtggagc ggctgctcca ggcgcaccgc caactggagg agcgcggcta tgtgttcgtc     1560
ggctaccacg gcaccttcct cgaagcggcg caaagcatcg tcttcggcgg ggtgcgcgcg     1620
cgcagccagg acctcgacgc gatctggcgc ggtttctata tcgccggcga tccggcgctg     1680
gcctacggct acgcccagga ccaggaaccc gacgcgcgcg gccggatccg caacggtgcc     1740
ctgctgcggg tctatgtgcc gcgctcgagc ctgccgggct tctaccgcac cggcctgacc     1800
ctggccgcgc cggaggcggc gggcgaggtc gaacggctga tcggccatcc gctgccgctg     1860
cgcctggacg ccatcaccgg ccccgaggag gaaggcgggc gcgtgaccat tctcggctgg     1920
ccgctggccg agcgcaccgt ggtgattccc tcggcgatcc ccaccgaccc cgcaacgtc      1980
ggcggcgacc tcgacccgtc cagcatcccc gacaaggaac aggcgatcag cgccctgccg     2040
gactacgcca gccagcccgg caaaccgccg cgcgaggacc tgaaggatca gaacgcgacc     2100
tcagccgtta ccgagtatta cctgaatcac ggcgaatggc ccggcaacaa cacttctgcc     2160
ggcgtggcaa cctcctctga aatcaaagga ggtggacacc accaccacca ccactaaaag     2220
ctt                                                                   2223
```

<210> SEQ ID NO 58
<211> LENGTH: 736
<212> TYPE: PRT
<213> ORGANISM: Artificial Sequence
<220> FEATURE:
<223> OTHER INFORMATION: rEPA4573NMC

<400> SEQUENCE: 58

Met Lys Lys Ile Trp Leu Ala Leu Ala Gly Leu Val Leu Ala Phe Ser
1               5                   10                  15

Ala Ser Ala Ala Glu Ser Ala Val Thr Glu Tyr Tyr Leu Asn His Gly
            20                  25                  30

Glu Trp Pro Gly Asn Asn Thr Ser Ala Gly Val Ala Thr Ser Ser Glu
        35                  40                  45

Ile Lys Thr Ser Glu Ala Phe Asp Leu Trp Asn Glu Cys Ala Lys Ala

```
            50                  55                  60
    Cys Val Leu Asp Leu Lys Asp Gly Val Arg Ser Ser Arg Met Ser Val
    65                  70                  75                  80

Asp Pro Ala Ile Ala Asp Thr Asn Gly Gln Gly Val Leu His Tyr Ser
                    85                  90                  95

Met Val Leu Glu Gly Gly Asn Asp Ala Leu Lys Leu Ala Ile Asp Asn
                100                 105                 110

Ala Leu Ser Ile Thr Ser Asp Gly Leu Thr Ile Arg Leu Glu Gly Gly
                115                 120                 125

Val Glu Pro Asn Lys Pro Val Arg Tyr Ser Tyr Thr Arg Gln Ala Arg
                130                 135                 140

Gly Ser Trp Ser Leu Asn Trp Leu Val Pro Ile Gly His Glu Lys Pro
    145                 150                 155                 160

Ser Asn Ile Lys Val Phe Ile His Glu Leu Asn Ala Gly Asn Gln Leu
                    165                 170                 175

Ser His Met Ser Pro Ile Tyr Thr Ile Glu Met Gly Asp Glu Leu Leu
                    180                 185                 190

Ala Lys Leu Ala Arg Asp Ala Thr Phe Phe Val Arg Ala His Glu Ser
                195                 200                 205

Asn Glu Met Gln Pro Thr Leu Ala Ile Ser His Ala Gly Val Ser Val
                210                 215                 220

Val Met Ala Gln Ala Gln Pro Arg Arg Glu Lys Arg Trp Ser Glu Trp
    225                 230                 235                 240

Ala Ser Gly Lys Val Leu Cys Leu Leu Asp Pro Leu Asp Gly Val Tyr
                    245                 250                 255

Asn Tyr Leu Ala Gln Gln Arg Cys Asn Leu Asp Asp Thr Trp Glu Gly
                    260                 265                 270

Lys Ile Tyr Arg Val Leu Ala Gly Asn Pro Ala Lys His Asp Leu Asp
                    275                 280                 285

Ile Lys Ser Ala Val Thr Glu Tyr Tyr Leu Asn His Gly Glu Trp Pro
                290                 295                 300

Gly Asn Asn Thr Ser Ala Gly Val Ala Thr Ser Ser Glu Ile Lys His
    305                 310                 315                 320

Met Pro Thr Val Ile Ser His Arg Leu His Phe Pro Glu Gly Gly Ser
                    325                 330                 335

Leu Ala Ala Leu Thr Ala His Gln Ala Cys His Leu Pro Leu Glu Thr
                340                 345                 350

Phe Thr Arg His Arg Gln Pro Arg Gly Trp Glu Gln Leu Glu Gln Cys
                355                 360                 365

Gly Tyr Pro Val Gln Arg Leu Val Ala Leu Tyr Leu Ala Ala Arg Leu
                370                 375                 380

Ser Trp Asn Gln Val Asp Gln Val Ile Gly Asn Ala Leu Ala Ser Pro
    385                 390                 395                 400

Gly Ser Gly Gly Asp Leu Gly Glu Ala Ile Arg Glu Gln Pro Glu Gln
                    405                 410                 415

Ala Arg Leu Ala Leu Thr Leu Ala Ala Glu Ser Glu Arg Phe Val
                420                 425                 430

Arg Gln Gly Thr Gly Asn Asp Glu Ala Gly Ala Ala Ser Ala Asp Val
                435                 440                 445

Val Ser Leu Thr Cys Pro Val Ala Ala Gly Glu Cys Ala Gly Pro Ala
                450                 455                 460

Asp Ser Gly Asp Ala Leu Leu Glu Arg Asn Tyr Pro Thr Gly Ala Glu
    465                 470                 475                 480
```

Phe Leu Gly Asp Gly Gly Asp Ile Ser Phe Ser Thr Arg Gly Thr Gln
            485                 490                 495

Asn Trp Thr Val Glu Arg Leu Leu Gln Ala His Arg Gln Leu Glu Glu
        500                 505                 510

Arg Gly Tyr Val Phe Val Gly Tyr His Gly Thr Phe Leu Glu Ala Ala
            515                 520                 525

Gln Ser Ile Val Phe Gly Gly Val Arg Ala Arg Ser Gln Asp Leu Asp
    530                 535                 540

Ala Ile Trp Arg Gly Phe Tyr Ile Ala Gly Asp Pro Ala Leu Ala Tyr
545                 550                 555                 560

Gly Tyr Ala Gln Asp Gln Glu Pro Asp Ala Arg Gly Arg Ile Arg Asn
                565                 570                 575

Gly Ala Leu Leu Arg Val Tyr Val Pro Arg Ser Ser Leu Pro Gly Phe
            580                 585                 590

Tyr Arg Thr Gly Leu Thr Leu Ala Ala Pro Glu Ala Ala Gly Glu Val
    595                 600                 605

Glu Arg Leu Ile Gly His Pro Leu Pro Leu Arg Leu Asp Ala Ile Thr
        610                 615                 620

Gly Pro Glu Glu Glu Gly Gly Arg Val Thr Ile Leu Gly Trp Pro Leu
625                 630                 635                 640

Ala Glu Arg Thr Val Val Ile Pro Ser Ala Ile Pro Thr Asp Pro Arg
                645                 650                 655

Asn Val Gly Gly Asp Leu Asp Pro Ser Ser Ile Pro Asp Lys Glu Gln
            660                 665                 670

Ala Ile Ser Ala Leu Pro Asp Tyr Ala Ser Gln Pro Gly Lys Pro Pro
        675                 680                 685

Arg Glu Asp Leu Lys Asp Gln Asn Ala Thr Ser Ala Val Thr Glu Tyr
    690                 695                 700

Tyr Leu Asn His Gly Glu Trp Pro Gly Asn Asn Thr Ser Ala Gly Val
705                 710                 715                 720

Ala Thr Ser Ser Glu Ile Lys Gly Gly His His His His
                725                 730                 735

<210> SEQ ID NO 59
<211> LENGTH: 1509
<212> TYPE: DNA
<213> ORGANISM: Artificial Sequence
<220> FEATURE:
<223> OTHER INFORMATION: rTTC4573

<400> SEQUENCE: 59
gaattcatga aaaagatttg gctggcgctg gctggtttag ttttagcgtt tagcgcatcg      60
gcggcgcagt atgaatccac catcctgaac ctggacatca acaatgacat catctccgat    120
atctctggct tcaactcctc tgtgatcacc tatccagatg ctcagctggt gccaggtatc    180
aacggcaaag ccatccacct ggtgaacaat gaatcctctg aagtgatcgt tcacaaggcc    240
atggacatcg aatacaacga catgttcaat aacttcaccg tgtccttctg gctgcgtgtt    300
ccgaaagtgt ccgcttctca cctggaacag tacgatacca acgaatattc catcatctct    360
tccatgaaga aatactctct gtccatcggt tctggctggt ccgtgtctct gaaaggtaac    420
aatctgatct ggaccctgaa ggactccgcc ggtgaagtgc gtcagatcac cttccgtgac    480
ctgtctgata aattcaacgc ctacctggct aacaagtggg tgttcatcac catcactaat    540
gaccgtctgt cctctgctaa cctgtacatc aatggcgttc tgatgggttc cgccgaaatc    600

```
actggtctgg gcgctatccg tgaagacaac aatatcaccc tgaagctgga ccgttgcaac      660
aataacaatc agtacgtgtc catcgacaag ttccgtatct tctgcaaagc cctgaacccg      720
aaggaaatcg aaaagctgta cacttcttat ctgtccatca ccttcctgcg tgacttctgg      780
ggtaacccac tgcgttacga tactgaatat tacctgatcc cagtggctta ttcctctaaa      840
gacgttcagc tgaagaacat caccgattac atgtatctga ctaacgctcc atcctacact      900
aacggcaaac tgaatatcta ctatcgtcgt ctgtactccg gtctgaagtt catcatcaaa      960
cgttatactc cgaacaatga aatcgactcc ttcgtgcgtt ctggtgattt catcaaactg     1020
tacgtttcct ataacaataa cgaacacatc gttggctacc caaggacgg taatgccttc      1080 aacaatctgg atcgtatcct gcgtgttggc tacaacgctc aggtatccc gctgtataag      1140 aaaatggaag ccgtgaaact gcgtgacctg aagacctact ccgtgcagct gaaactgtat     1200
gacgataaag acgcctctct gggtctggtt ggcactcaca acggtcagat cggcaatgac     1260
ccaaaccgtg atatcctgat cgcctccaac tggtacttca atcacctgaa agacaagact     1320
ctgacctgcg attggtactt cgtgccaact gatgaaggtt ggaccaacga cgatcagaac     1380
gcgacctcag ccgttaccga gtattacctg aatcacggcg aatggcccgg caacaacact     1440
tctgccggcg tggcaacctc ctctgaaatc aaaggaggtg acaccacca ccaccaccac      1500 taaaagctt                                                             1509
```

<210> SEQ ID NO 60
<211> LENGTH: 498
<212> TYPE: PRT
<213> ORGANISM: Artificial Sequence
<220> FEATURE:
<223> OTHER INFORMATION: rTTC4573

<400> SEQUENCE: 60

```
Met Lys Lys Ile Trp Leu Ala Leu Ala Gly Leu Val Leu Ala Phe Ser
1               5                   10                  15

Ala Ser Ala Ala Gln Tyr Glu Ser Thr Ile Leu Asn Leu Asp Ile Asn
                20                  25                  30

Asn Asp Ile Ile Ser Asp Ile Ser Gly Phe Asn Ser Ser Val Ile Thr
            35                  40                  45

Tyr Pro Asp Ala Gln Leu Val Pro Gly Ile Asn Gly Lys Ala Ile His
        50                  55                  60

Leu Val Asn Asn Glu Ser Ser Glu Val Ile Val His Lys Ala Met Asp
65                  70                  75                  80

Ile Glu Tyr Asn Asp Met Phe Asn Phe Thr Val Ser Phe Trp Leu
                85                  90                  95

Arg Val Pro Lys Val Ser Ala Ser His Leu Glu Gln Tyr Asp Thr Asn
                100                 105                 110

Glu Tyr Ser Ile Ile Ser Ser Met Lys Lys Tyr Ser Leu Ser Ile Gly
            115                 120                 125

Ser Gly Trp Ser Val Ser Leu Lys Gly Asn Asn Leu Ile Trp Thr Leu
        130                 135                 140

Lys Asp Ser Ala Gly Glu Val Arg Gln Ile Thr Phe Arg Asp Leu Ser
145                 150                 155                 160

Asp Lys Phe Asn Ala Tyr Leu Ala Asn Lys Trp Val Phe Ile Thr Ile
                165                 170                 175

Thr Asn Asp Arg Leu Ser Ser Ala Asn Leu Tyr Ile Asn Gly Val Leu
            180                 185                 190

Met Gly Ser Ala Glu Ile Thr Gly Leu Gly Ala Ile Arg Glu Asp Asn
```

|     |     |     |     | 195 |     |     |     |     | 200 |     |     |     |     | 205 |     |
| --- | --- | --- | --- | --- | --- | --- | --- | --- | --- | --- | --- | --- | --- | --- | --- |

Asn Ile Thr Leu Lys Leu Asp Arg Cys Asn Asn Asn Gln Tyr Val
210                     215                     220

Ser Ile Asp Lys Phe Arg Ile Phe Cys Lys Ala Leu Asn Pro Lys Glu
225                     230                     235                     240

Ile Glu Lys Leu Tyr Thr Ser Tyr Leu Ser Ile Thr Phe Leu Arg Asp
                        245                     250                     255

Phe Trp Gly Asn Pro Leu Arg Tyr Asp Thr Glu Tyr Tyr Leu Ile Pro
                260                     265                     270

Val Ala Tyr Ser Ser Lys Asp Val Gln Leu Lys Asn Ile Thr Asp Tyr
            275                     280                     285

Met Tyr Leu Thr Asn Ala Pro Ser Tyr Thr Asn Gly Lys Leu Asn Ile
290                     295                     300

Tyr Tyr Arg Arg Leu Tyr Ser Gly Leu Lys Phe Ile Ile Lys Arg Tyr
305                     310                     315                     320

Thr Pro Asn Asn Glu Ile Asp Ser Phe Val Arg Ser Gly Asp Phe Ile
                        325                     330                     335

Lys Leu Tyr Val Ser Tyr Asn Asn Glu His Ile Val Gly Tyr Pro
                340                     345                     350

Lys Asp Gly Asn Ala Phe Asn Asn Leu Asp Arg Ile Leu Arg Val Gly
            355                     360                     365

Tyr Asn Ala Pro Gly Ile Pro Leu Tyr Lys Lys Met Glu Ala Val Lys
370                     375                     380

Leu Arg Asp Leu Lys Thr Tyr Ser Val Gln Leu Lys Leu Tyr Asp Asp
385                     390                     395                     400

Lys Asp Ala Ser Leu Gly Leu Val Gly Thr His Asn Gly Gln Ile Gly
                        405                     410                     415

Asn Asp Pro Asn Arg Asp Ile Leu Ile Ala Ser Asn Trp Tyr Phe Asn
                420                     425                     430

His Leu Lys Asp Lys Thr Leu Thr Cys Asp Trp Tyr Phe Val Pro Thr
            435                     440                     445

Asp Glu Gly Trp Thr Asn Asp Asp Gln Asn Ala Thr Ser Ala Val Thr
450                     455                     460

Glu Tyr Tyr Leu Asn His Gly Glu Trp Pro Gly Asn Asn Thr Ser Ala
465                     470                     475                     480

Gly Val Ala Thr Ser Ser Glu Ile Lys Gly Gly His His His
                        485                     490                     495

His His

<210> SEQ ID NO 61
<211> LENGTH: 26
<212> TYPE: DNA
<213> ORGANISM: Artificial Sequence
<220> FEATURE:
<223> OTHER INFORMATION: 73waaLu1

<400> SEQUENCE: 61
cgggatccag gctttgacta tgtgga                                        26

<210> SEQ ID NO 62
<211> LENGTH: 27
<212> TYPE: DNA
<213> ORGANISM: Artificial Sequence
<220> FEATURE:
<223> OTHER INFORMATION: 73waaLu2

<400> SEQUENCE: 62
gcgtcgacat ctggcgatat gagtatg                                     27

<210> SEQ ID NO 63
<211> LENGTH: 26
<212> TYPE: DNA
<213> ORGANISM: Artificial Sequence
<220> FEATURE:
<223> OTHER INFORMATION: 73waaLd1

<400> SEQUENCE: 63
ccaagcttta gtgcaggcat attggg                                      26

<210> SEQ ID NO 64
<211> LENGTH: 26
<212> TYPE: DNA
<213> ORGANISM: Artificial Sequence
<220> FEATURE:
<223> OTHER INFORMATION: 73waaLd2

<400> SEQUENCE: 64
ccctcgagta tcacctcgca gaacct                                      26

<210> SEQ ID NO 65
<211> LENGTH: 19
<212> TYPE: DNA
<213> ORGANISM: Artificial Sequence
<220> FEATURE:
<223> OTHER INFORMATION: 73waaLw1

<400> SEQUENCE: 65
aacaccggat tacggataa                                              19

<210> SEQ ID NO 66
<211> LENGTH: 18
<212> TYPE: DNA
<213> ORGANISM: Artificial Sequence
<220> FEATURE:
<223> OTHER INFORMATION: 73waaLw2

<400> SEQUENCE: 66
tgcatggtgg ctgtagaa                                               18

<210> SEQ ID NO 67
<211> LENGTH: 18
<212> TYPE: DNA
<213> ORGANISM: Artificial Sequence
<220> FEATURE:
<223> OTHER INFORMATION: 73waaLn1

<400> SEQUENCE: 67
agaaacggtt gcgaaaat                                               18

<210> SEQ ID NO 68
<211> LENGTH: 18
<212> TYPE: DNA
<213> ORGANISM: Artificial Sequence
<220> FEATURE:
<223> OTHER INFORMATION: 73waaLn2

<400> SEQUENCE: 68
atagccgtag cccttgat                                               18

<210> SEQ ID NO 69
<211> LENGTH: 28
<212> TYPE: DNA

```
<213> ORGANISM: Artificial Sequence
<220> FEATURE:
<223> OTHER INFORMATION: Kan1

<400> SEQUENCE: 69
gcgtcgacgt gtaggctgga gctgcttc                                              28

<210> SEQ ID NO 70
<211> LENGTH: 28
<212> TYPE: DNA
<213> ORGANISM: Artificial Sequence
<220> FEATURE:
<223> OTHER INFORMATION: Kan2

<400> SEQUENCE: 70
ccaagcttat gggaattagc catggtcc                                              28

<210> SEQ ID NO 71
<211> LENGTH: 2549
<212> TYPE: DNA
<213> ORGANISM: Artificial Sequence
<220> FEATURE:
<223> OTHER INFORMATION: pETKan

<400> SEQUENCE: 71
ggatccaggc tttgactatg tggatgtgtt accgcgcatg agcctggagg aggtcgccag          60
agtgctggct ggcgcaaaat tgtcgtatc ggttgatacc ggcctgagcc atctttccgc          120
ggcgctcgac agaccgaata ttacgctata tgcccaacg accctgggt taattggagg           180
ttatgggaag aaccaaatgg catgctgctc accagaacaa aacctggcga atttagatgc         240
cacaagcgta tttggaaaga ttcattaaag agactctgtc tcatcccaaa cctattgtgg         300
agaaaagatg ctaaccacat cattaacgtt aaataaagag aaatggaagc cgatctggaa         360
taaagcgctg gttttttcttt ttgttgccac gtattttctg gatggtatta cgcgttataa       420
acatttgata atcatactta tggttatcac cgcgatttat caggtctcac gctcaccgaa         480
aagtttcccc cctctttttca aaaatagcgt attttatagc gtagcagtat tatcattaat        540
ccttgtttat tccatactca tatcgccaga tgtcgacgtg taggctggag ctgcttcgaa         600
gttcctatac tttctagaga ataggaactt cggaatagga acttcaagat ccctcacgc          660
tgccgcaagc actcagggcg caagggctgc taaaggaagc ggaacacgta gaaagccagt         720
ccgcagaaac ggtgctgacc ccggatgaat gtcagctact gggctatctg gacaagggaa         780
aacgcaagcg caaagagaaa gcaggtagct tgcagtgggc ttacatggcg atagctagac         840
tgggcggttt tatggacagc aagcgaaccg gaattgccag ctggggcgcc ctctggtaag         900
gttgggaagc cctgcaaagt aaactggatg cttttcttgc cgccaaggat ctgatgcgc          960
agggatcaa gatctgatca agagacagga tgaggatcgt ttcgcatgat tgaacaagat         1020
ggattgcacg caggttctcc ggccgcttgg gtggagaggc tattcggcta tgactgggca        1080
caacagacaa tcggctgctc tgatgccgcc gtgttccggc tgtcagcgca ggggcgcccg        1140
gttcttttg tcaagaccga cctgtccggt gccctgaatg aactgcagga cgaggcagcg         1200
cggctatcgt ggctggccac gacgggcgtt ccttgcgcag ctgtgctcga cgttgtcact        1260
gaagcgggaa gggactggct gctattgggc gaagtgccgg gcaggatct cctgtcatct         1320
caccttgctc ctgccgagaa agtatccatc atggctgatg caatgcggcg gctgcatacg        1380
cttgatccgg ctacctgccc attcgaccac caagcgaaac atcgcatcga gcgagcacgt         1440
actcggatgg aagccggtct tgtcgatcag gatgatctgg acgaagagca tcaggggctc        1500
```

```
gcgccagccg aactgttcgc caggctcaag gcgcgcatgc ccgacggcga ggatctcgtc    1560
gtgacccatg gcgatgcctg cttgccgaat atcatggtgg aaaatggccg ctttctgga    1620 ttcatcgact gtggccggct gggtgtggcg gaccgctatc aggacatagc gttggctacc    1680
cgtgatattg ctgaagagct tggcggcgaa tgggctgacc gcttcctcgt gctttacggt    1740
atcgccgctc ccgattcgca gcgcatcgcc ttctatcgcc ttcttgacga gttcttctga    1800
gcgggactct ggggttcgaa atgaccgacc aagcgacgcc caacctgcca tcacgagatt    1860
tcgattccac cgccgccttc tatgaaaggt tgggcttcgg aatcgttttc cgggacgccg    1920
gctggatgat cctccagcgc ggggatctca tgctggagtt cttcgcccac cccagcttca    1980
aaagcgctct gaagttccta tactttctag agaataggaa cttcggaata ggaactaagg    2040
aggatattca tatggaccat ggctaattcc cataagcttt agtgcaggca tattgggtct    2100
ggcgagcctg gcctatttat atggtgctat catcagggaa acagccagct ctaccttcag    2160
gaaagtagag ataagcccct acaatgctca tctcttgcta tttttatctt tcgtcggttt    2220
ttatatcgtt cgtggcaatt ttgaacaggt cgatattgct caaattggta tcattaccgg    2280
ttttctgctg gcgctaagaa atagataaaa aacgcgctga tacttattac ggtatcagcg    2340
cgttttccat catcaggact caatcactta tcaaaccagt ttttcatttg ttcctcgaaa    2400
cgctgcgcta cattttccca actgtatttt gaaaacacca gggattttgc ttttcggca     2460 atctggtggc gttccttatc agcaagcgca cggttaatat cattaattat actgtcgctc    2520
gacataggtt ctgcgaggtg atactcgag                                      2549

<210> SEQ ID NO 72
<211> LENGTH: 61
<212> TYPE: DNA
<213> ORGANISM: Artificial Sequence
<220> FEATURE:
<223> OTHER INFORMATION: 3110waaLcat

<400> SEQUENCE: 72
gcagttttgg aaaagttatc atcattataa aggtaaaaca tagcgattgt gtaggctgga    60
g                                                                    61

<210> SEQ ID NO 73
<211> LENGTH: 66
<212> TYPE: DNA
<213> ORGANISM: Artificial Sequence
<220> FEATURE:
<223> OTHER INFORMATION: 3110waaLcat

<400> SEQUENCE: 73
agtgagtttt aactcacttc ttaaacttgt ttattcttaa taattaacgg ctgacatggg    60
aattag                                                               66

<210> SEQ ID NO 74
<211> LENGTH: 19
<212> TYPE: DNA
<213> ORGANISM: Artificial Sequence
<220> FEATURE:
<223> OTHER INFORMATION: 3110waaL

<400> SEQUENCE: 74
tacaaatagt atccccaac                                                 19

<210> SEQ ID NO 75
```

```
<211> LENGTH: 19
<212> TYPE: DNA
<213> ORGANISM: Artificial Sequence
<220> FEATURE:
<223> OTHER INFORMATION: 3110waaL

<400> SEQUENCE: 75
aattaacctc aacagtcaa                                                  19

<210> SEQ ID NO 76
<211> LENGTH: 1133
<212> TYPE: DNA
<213> ORGANISM: Artificial Sequence
<220> FEATURE:
<223> OTHER INFORMATION: chlormnphenicol-resistant gene fragment

<400> SEQUENCE: 76
gcagttttgg aaaagttatc atcattataa aggtaaaaca tagcgattgt gtaggctgga     60
gctgcttcga agttcctata ctttctagag aataggaact tcggaatagg aacttcattt   120
aaatggcgcg ccttacgccc cgccctgcca ctcatcgcag tactgttgta ttcattaagc   180
atctgccgac atggaagcca tcacaaacgg catgatgaac ctgaatcgcc agcggcatca   240
gcaccttgtc gccttgcgta taatatttgc ccatggtgaa acgggggcg aagaagttgt    300 ccatattggc cacgtttaaa tcaaaactgg tgaaactcac ccagggattg ctgagacga    360 aaaacatatt ctcaataaac cctttaggga ataggccag ttttcaccg taacacgcca     420 catcttgcga atatatgtgt agaaactgcc ggaaatcgtc gtggtattca ctccagagcg   480
atgaaaacgt ttcagtttgc tcatggaaaa cggtgtaaca agggtgaaca ctatcccata   540
tcaccagctc accgtctttc attgccatac gtaattccgg atgagcattc atcaggcggg   600
caagaatgtg aataaaggcc ggataaaact tgtgcttatt tttctttacg gtctttaaaa   660
aggccgtaat atccagctga acggtctggt tataggtaca ttgagcaact gactgaaatg   720
cctcaaaatg ttctttacga tgccattggg atatatcaac ggtggtatat ccagtgattt   780
ttttctccat tttagcttcc ttagctcctg aaaatctcga caactcaaaa aatacgcccg   840
gtagtgatct tatttcatta tggtgaaagt tggaacctct tacgtgccga tcaacgtctc   900
attttcgcca aaagttggcc cagggcttcc cggtatcaac agggacacca ggatttattt   960
attctgcgaa gtgatcttcc gtcacaggta ggcgcgccga agttcctata ctttctagag  1020
aataggaact tcggaatagg aactaaggag gatattcata tggaccatgg ctaattccca  1080
tgtcagccgt taattaagaa taaacaagtt taagaagtga gttaaaactc act         1133

<210> SEQ ID NO 77
<211> LENGTH: 52
<212> TYPE: DNA
<213> ORGANISM: Artificial Sequence
<220> FEATURE:
<223> OTHER INFORMATION: O157

<400> SEQUENCE: 77
agaaggcgcg ccaagaatga cgaatttaaa agcagttata ccggtagcag gt          52

<210> SEQ ID NO 78
<211> LENGTH: 48
<212> TYPE: DNA
<213> ORGANISM: Artificial Sequence
<220> FEATURE:
<223> OTHER INFORMATION: O157

<400> SEQUENCE: 78
```
atatgcggcc gcttaatcca gccattcggt atggaacaca ccttctttt 48

<210> SEQ ID NO 79
<211> LENGTH: 16582
<212> TYPE: DNA
<213> ORGANISM: Artificial Sequence
<220> FEATURE:
<223> OTHER INFORMATION: 0157 polysaccharide synthesis gene

<400> SEQUENCE: 79

| | |
|---|---|
| ggcgcgccaa gaatgacgaa tttaaaagca gttataccgg tagcaggtct tgggatgcat | 60 |
| atgttgcctg ccactaaggc gattcccaaa gagatgctac cgatcgtcga caagccaatg | 120 |
| attcagtaca ttgttgacga gattgtggct gcagggatca agaaatcct cctggtaact | 180 |
| cacgcgtcca agaacgcagt cgaaaaccac ttcgacacct cttatgaatt agaatctctc | 240 |
| cttgaacagc gcgtgaagcg tcaactactg gcggaagtac aatctatctg tccgccgggc | 300 |
| gtgaccatta tgaacgtgcg tcagggtgaa cctttaggtt taggccactc cattttatgt | 360 |
| gcgcgacctg ccattggtga caatccattt gtcgtggtgc tgccagacgt tgtgatcgac | 420 |
| gacgccagcg ccgacccgct acgctacaac cttgctgcca tgattgcgcg cttcaatgaa | 480 |
| acgggacgca gccaggtgct ggcaaaacgt atgccgggcg acctctctga atactccgtc | 540 |
| atccagacca agaaccgct ggatcgtgaa ggcaaagtca gccgcattgt tgaatttatc | 600 |
| gaaaagccgg atcagccgca gacgctggac tcagacatca tggccgttgg tcgatatgtg | 660 |
| ctttctgccg atatttggcc ggaactgaa cgtactcagc ctggtgcatg gggacgtatt | 720 |
| cagctgactg atgccattgc tgagctggca aaaaaacaat ccgttgatgc aatgctgatg | 780 |
| actggcgaca gttacgactg cggtaaaaaa atgggctata tgcaggcgtt tgtgaagtat | 840 |
| ggactacgca acttgaaaga aggggcgaag ttccgcaaag gtatcgagaa gctgttaagc | 900 |
| gaataatgaa atctgaccg aatgtaacgg ttgataagga ataatatcg gcagtgaaaa | 960 |
| actatagatc aataaatatc actgctgttg agctttata attaactatg ctaccaatga | 1020 |
| ataaatagtg tgcagatatg tatttttgt ttggtagtct tgtttctccc tctgaataat | 1080 |
| aagataataa acgcttggag atgatttttt taacatggat tatcatttcg tacactggta | 1140 |
| gcgattaagc caggggcggt agcgtgcata aattttaatg cttatcaaaa ctattagcat | 1200 |
| taaaaatata taagaaattc tcaaatgaac aaagaaaccg tttcaataat tatgcccgtt | 1260 |
| tacaatgggg ccaaaactat aatctcatca gtagaatcaa ttatacatca atcttatcaa | 1320 |
| gatttgtttt tgtatatcat tgacgattgt agcaccgatg atacattttc attaatcaac | 1380 |
| agtcgataca aaaacaatca gaaataaga atattgcgta acaagacaaa tttaggtgtt | 1440 |
| gcagaaagtc gaaattatgg aatagaaatg gccacgggga aatatatttc tttttgtgat | 1500 |
| gcggatgatt tgtggcacga gaaaaaatta gagcgtcaaa tcgaagtgtt aaataatgaa | 1560 |
| tgtgtagatg tggtatgttc taattattat gttatagata caaaagaaa tattgttggc | 1620 |
| gaagttaatg ctcctcatgt gataaattat agaaaaatgc tcatgaaaaa ctacataggg | 1680 |
| aatttgacag gaatctataa tgccaacaaa ttgggtaagt tttatcaaaa aaagattggt | 1740 |
| cacgaggatt atttgatgtg gctgaaata attaataaaa caaatggtgc tatttgtatt | 1800 |
| caagataatc tggcgtatta catgcgttca ataattcac tatcgggtaa taaaattaaa | 1860 |
| gctgcaaaat ggcatggag tatatataga gaacatttac atttgtcctt tccaaaaaca | 1920 |
| ttatattatt ttttattata tgcttcaaat ggagtcatga aaaaaataac acattcacta | 1980 |

```
ttaaggagaa aggagactaa aaagtgaagt cagcggctaa gttgattttt ttattcctat    2040
ttacacttta tagtctccag ttgtatgggg ttatcataga tgatcgtata acaaattttg    2100
atacaaaggt attaactagt attataatta tatttcagat ttttttttgtt ttattatttt    2160
atctaacgat tataaatgaa agaaaacagc agaaaaaatt tatcgtgaac tgggagctaa    2220
agttaatact cgttttcctt tttgtgacta tagaaattgc tgctgtagtt ttatttctta    2280
aagaaggtat tcctatattt gatgatgatc caggggggggc taaacttaga atagctgaag    2340
gtaatggact ttacattaga tatattaagt attttggtaa tatagttgtg tttgcattaa    2400
ttattctttta tgatgagcat aaattcaaac agaggaccat catatttgta tattttacaa    2460
cgattgcttt atttggttat cgttctgaat tggtgttgct cattcttcaa tatatattga    2520
ttaccaatat cctgtcaaag gataaccgta atcctaaaat aaaaagaata atagggtatt    2580
ttttattggt agggggttgta tgctcgttgt tttatctaag tttaggacaa acggagaac     2640
aaaatgactc atataataat atgttaagga taattaatag gttaacaata gagcaagttg    2700
aaagtgttcc atatgttgtt tctgaatcta ttaagaacga tttctttccg acaccagagt    2760
tagaaaagga attaaaagca ataataaata gaatacaggg aataaagcat caagacttat    2820
tttatggaga acggttacat aaacaagtat ttggagacat gggagcaaat tttttatcag    2880
ttactacgta tggagcagaa ctgttagttt ttttttggttt tctctgtgta ttcattatcc    2940
ctttagggat atatatacct ttttatcttt taaagagaat gaaaaaaacc catagctcga    3000
taaattgcgc attctattca tatatcatta tgattttatt gcaatactta gtggctggga    3060
atgcatcggc cttctttttt ggtccttttc tctccgtatt gataatgtgt actcctctga    3120
tcttattgca tgatacgtta aagagattat cacgaaatga aaatatcagt tataactgtg    3180
acttataata atgctgaagg gttagaaaaa acttttaagta gtttatcaat tttaaaaata    3240
aaacctttttg agattattat agttgatggc ggctctacag atggaacgaa tcgtgtcatt    3300
agtagattta ctagtatgaa tattacacat gtttatgaaa aagatgaagg gatatatgat    3360
gcgatgaata agggccgaat gttggccaaa ggcgacttaa tacattattt aaacgccggc    3420
gatagcgtaa ttggagatat atataaaaat atcaaagagc catgtttgat taaagttggc    3480
cttttcgaaa atgataaact tctgggatttt tcttctataa cccattcaaa tacagggtat    3540
tgtcatcaag gggtgatttt cccaaagaat cattcagaat atgatctaag gtataaaata    3600
tgtgctgatt ataagcttat tcaagaggtg tttcctgaag ggttaagatc tctatctttg    3660
attacttcgg gttatgtaaa atatgatatg gggggagtat cttcaaaaaa agaattttta    3720
agagataaag agcttgccaa aattatgttt gaaaaaaata aaaaaaacct tattaagttt    3780
attccaattt caataatcaa aatttttattc cctgaacgtt taagaagagt attgcggaaa    3840
atgcaatata tttgtctaac tttattcttc atgaagaata gttcaccata tgataatgaa    3900
taaaatcaaa aaaatactta aattttgcac tttaaaaaaa tatgatacat caagtgcttt    3960
aggtagagaa caggaaaggt acaggattat atccttgtct gttatttcaa gtttgattag    4020
taaaatactc tcactacttt ctcttatatt aactgtaagt ttaactttac cttatttagg    4080
acaagagaga tttggtgtat ggatgactat taccagtctt ggtgctgctc tgacatttt     4140
ggacttaggt ataggaaatg cattaacaaa caggatcgca cattcatttg cgtgtggcaa    4200
aaatttaaag atgagtcggc aaattagtgg tgggctcact ttgctggctg gattatcgtt    4260
tgtcataact gcaatatgct atattacttc tggcatgatt gattggcaac tagtaataaa    4320
aggtataaac gagaatgtgt atgcagagtt acaacactca attaaagtct ttgtaatcat    4380
```

```
atttggactt ggaatttatt caaatggtgt gcaaaaagtt tatatgggaa tacaaaaagc    4440
ctatataagt aatattgtta atgccatatt tatattgtta tctattatta ctctagtaat    4500
atcgtcgaaa ctacatgcgg gactaccagt tttaattgtc agcactcttg gtattcaata    4560
catatcggga atctatttaa caattaatct tattataaag cgattaataa agtttacaaa    4620
agttaacata catgctaaaa gagaagctcc atatttgata ttaaacggtt ttttcttttt    4680
tattttacag ttaggcactc tggcaacatg gagtggtgat aactttataa tatctataac    4740
attgggtgtt acttatgttg ctgtttttag cattacacag agattatttc aaatatctac    4800
ggtccctctt acgatttata acatcccgtt atgggctgct tatgcagatg ctcatgcacg    4860
caatgatact caatttataa aaaagacgct cagaacatca ttgaaaatag tgggtatttc    4920
atcattctta ttggccttca tattagtagt gttcggtagt gaagtcgtta atatttggac    4980
agaaggaaag attcaggtac ctcgaacatt cataatagct tatgctttat ggtctgttat    5040
tgatgctttt tcgaatacat ttgcaagctt tttaaatggt ttgaacatag ttaaacaaca    5100
aatgcttgct gttgtaacat tgatattgat cgcaattcca gcaaaataca tcatagttag    5160
ccattttggg ttaactgtta tgttgtactg cttcattttt atatatattg taaattactt    5220
tatatggtat aaatgtagtt ttaaaaaaca tatcgataga cagttaaata taagaggatg    5280
aaaatgaaat atataccagt ttaccaaccg tcattgacag gaaagaaaa agaatatgta    5340 aatgaatgtc tggactcaac gtggatttca tcaaaaggaa actatattca gaagtttgaa    5400
aataaatttg cggaacaaaa ccatgtgcaa tatgcaacta ctgtaagtaa tggaacggtt    5460
gctcttcatt tagctttgtt agcgttaggt atatcggaag gagatgaagt tattgttcca    5520
acactgacat atatagcatc agttaatgct ataaaataca caggagccac ccccatttc    5580 gttgattcag ataatgaaac ttggcaaatg tctgttagtg acatagaaca aaaaatcact    5640
aataaaacta agctattat gtgtgtccat ttatacggac atccatgtga tatggaacaa    5700
attgtagaac tggccaaaag tagaaatttg tttgtaattg aagattgcgc tgaagccttt    5760
ggttctaaat ataaaggtaa atatgtggga catttggag atatttctac ttttagcttt    5820
tttgaaaata aaactattac tacaggtgaa ggtggaatgg ttgtcacgaa tgacaaaaca    5880
ctttatgacc gttgtttaca ttttaaaggc caaggattag ctgtacatag gcaatattgg    5940
catgacgtta taggctacaa ttataggatg acaaatatct gcgctgctat aggattagcc    6000
cagttagaac aagctgatga ttttatatca cgaaaacgtg aaattgctga tatttataaa    6060
aaaaatatca acagtcttgt acaagtccac aaggaaagta aagatgtttt tcacacttat    6120
tggatggtct caattctaac taggaccgca gaggaaagag aggaattaag gaatcacctt    6180
gcagataaac tcatcgaaac aaggccagtt ttttacccctg tccacacgat gccaatgtac    6240
tcggaaaaat atcaaaagca ccctatagct gaggatcttg gttggcgtgg aattaattta    6300
cctagtttcc ccagcctatc gaatgagcaa gttatttata tttgtgaatc tattaacgaa    6360
ttttatagtg ataaatagcc taaaatattg taaaggtcat tcatgaaaat tgcgttgaat    6420
tcagatggat tttacgagtg gggcggtgga attgattta ttaaatatat tctgtcaata    6480
ttagaaacga aaccagaaat atgtatcgat attcttttac cgagaaatga tatacattct    6540
cttataagag aaaaagcatt tccttttaaa agtatattaa agcaatttt aaagagggaa    6600 aggcctcgat ggatttcatt aaatagattt aatgagcaat actatagaga tgcctttaca    6660
caaaataata tagagacgaa tcttaccttt attaaaagta agagctctgc ctttattca    6720
```

```
tatttttgata gtagcgattg tgatgttatt cttccttgca tgcgtgttcc ttcgggaaat      6780
ttgaataaaa aagcatggat tggttatatt tatgactttc aacactgtta ctatccttca      6840 tttttttagta agcgagaaat agatcaaagg aatgtgtttt ttaaattgat gctcaattgc     6900
gctaacaata ttattgttaa tgcacattca gttattaccg atgcaaataa atatgttggg      6960
aattattctg caaaactaca ttctcttcca tttagtccat gccctcaatt aaaatggttc      7020
gctgattact ctggtaatat tgccaaatat aatattgaca aggattattt tataatttgc      7080
aatcaatttt ggaaacataa agatcatgca actgctttta gggcatttaa aatttatact      7140
gaatataatc ctgatgttta tttagtatgc acgggagcta ctcaagatta tcgattccct      7200
ggatatttta atgaattgat ggttttggca aaaaagctcg gaattgaatc gaaaattaag      7260
atattagggc atatacctaa acttgaacaa attgaattaa tcaaaaattg cattgctgta      7320
atacaaccaa ccttatttga aggcgggcct ggagggggggg taacatttga cgctattgca     7380
ttagggaaaa aagttatact atctgacata gatgtcaata agaagttaa ttgcggtgat       7440 gtatatttct ttcaggcaaa aaaccattat tcattaaatg acgcgatggt aaaagctgat      7500
gaatctaaaa ttttttatga acctacaact ctgatagaat tgggtctcaa agacgcaat      7560 gcgtgtgcag atttctttt agatgttgtg aaacaagaaa ttgaatcccg atcttaatat      7620
attcaagagg tatataatga ctaaagtcgc tcttattaca ggtgtaactg acaagatgg       7680 atcttatcta gctgagtttt tgcttgataa agggtatgaa gttcatggta tcaaacgccg      7740
agcctcatct tttaatacag aacgcataga ccatatttat caagatccac atggttctaa     7800 cccaaattt cacttgcact atggagatct gactgattca tctaacctca ctagaattct      7860
aaaggaggta cagccagatg aagtatataa tttagctgct atgagtcacg tagcagtttc     7920
ttttgagtct ccagaatata cagccgatgt cgatgcaatt ggtacattac gtttactgga    7980
agcaattcgc ttttaggat tggaaaacaa aacgcgtttc tatcaagctt caacctcaga     8040
attatatgga cttgttcagg aaatccctca aaaagaatcc acccctttt atcctcgttc     8100 ccctattgca gttgcaaaac tttacgcata ttggatcacg gtaaattatc gagagtcata    8160
tggtatttat gcatgtaatg gtatattgtt caatcatgaa tctccacgcc gtggagaaac    8220
gtttgtaaca aggaaaatta ctcgaggact tgcaaatatt gcacaaggct tggaatcatg    8280
tttgtattta gggaatatgg attcgttacg agattgggga catgcaaaag attatgttag    8340
aatgcaatgg ttgatgttac aacaggagca acccgaagat tttgtgattg caacaggagt   8400
ccaatactca gtccgtcagt ttgtcgaaat ggcagcagca caacttggta ttaagatgag    8460 cttgttggt aaaggaatcg aagaaaaagg cattgtagat tcggttgaag acaggatgc     8520 tccaggtgtg aaaccaggtg atgtcattgt tgctgttgat cctcgttatt ccgaccagc    8580 tgaagttgat actttgcttg gagatccgag caaagctaat ctcaaacttg gttggagacc    8640
agaaattact cttgctgaaa tgatttctga aatggttgcc aaagatcttg aagccgctaa    8700
aaaacattct cttttaaaat cgcatggttt ttctgtaagc ttagctctgg aatgatgatg    8760
aataagcaac gtattttttat tgctggtcac caaggaatgg ttggatcagc tattacccga   8820
cgcctcaaac aacgtgatga tgttgagttg gttttacgta ctcgggatga attgaacttg    8880
ttggatagta gcgctgtttt ggatttttt tcttcacaga aaatcgacca ggtttattg     8940 gcagcagcaa aagtcggagg tatttttagct aacagttctt atcctgccga ttttatatat   9000
gagaatataa tgatagaggc gaatgtcatt catgctgccc acaaaaataa tgtaaataaa    9060 ctgctttttcc tcggttcgtc gtgtatttat cctaagttag cacaccaacc gattatggaa   9120
```

```
gacgaattat tacaagggaa acttgagcca acaaatgaac cttatgctat cgcaaaaatt    9180
gcaggtatta aattatgtga atcttataac cgtcagtttg ggcgtgatta ccgttcagta    9240
atgccaacca atctttatgg tccaaatgac aattttcatc caagtaattc tcatgtgatt    9300
ccggcgcttt tgcgccgctt tcatgatgct gtggaaaaca attctccgaa tgttgttgtt    9360
tggggaagtg gtactccaaa gcgtgaattc ttacatgtag atgatatggc ttctgcaagc    9420
atttatgtca tggagatgcc atacgatata tggcaaaaaa atactaaagt aatgttgtct    9480
catatcaata ttggaacagg tattgactgc acgatttgtg agcttgcgga acaatagca     9540 aaagttgtag gttataaagg gcatattacg ttcgatacaa caaagcccga tggagcccct    9600
cgaaaactac ttgatgtaac gcttcttcat caactaggtt ggaatcataa aattacccctt   9660 cacaagggtc ttgaaaatac atacaactgg tttcttgaaa accaacttca atatcggggg    9720
taataatgtt tttacattcc caagactttg ccacaattgt aaggtctact cctcttattt    9780
ctatagattt gattgtggaa aacgagtttg gcgaaatttt gctaggaaaa cgaatcaacc    9840
gcccggcaca gggctattgg ttcgttcctg gtggtagggt gttgaaagat gaaaaattgc    9900
agacagcctt tgaacgattg acagaaattg aactaggaat tcgtttgcct ctctctgtgg    9960
gtaagtttta tggtatctgg cagcacttct acgaagacaa tagtatgggg ggagactttt   10020
caacgcatta tatagttata gcattccttc ttaaattaca accaaacatt ttgaaattac   10080
cgaagtcaca acataatgct tattgctggc tatcgcgagc aaagctgata aatgatgacg   10140
atgtgcatta taattgtcgc gcatatttta acaataaaac aaatgatgcg attggcttag   10200
ataataagga tataatatgt ctgatgcgcc aataattgct gtagttatgg ccggtggtac   10260
aggcagtcgt cttgccac tttctcgtga actatatcca aagcagtttt tacaactctc    10320
tggtgataac accttgttac aaacgacttt gctacgactt tcaggcctat catgtcaaaa   10380
accattagtg ataacaaatg aacagcatcg ctttgttgtg gctgaacagt aagggaaat    10440 aaataaatta aatggtaata ttattctaga accatgcggg cgaaatactg caccagcaat   10500
agcgatatct gcgtttcatg cgttaaaacg taatcctcag gaagatccat tgcttctagt   10560
tcttgcggca gaccacgtta tagctaaaga aagtgttttc tgtgatgcta ttaaaaatgc   10620
aactcccatc gctaatcaag gtaaaattgt aacgtttgga attataccag aatatgctga   10680
aactggttat gggtatattg agagaggtga actatctgta ccgcttcaag gcatgaaaa    10740 tactggtttt tattatgtaa ataagtttgt cgaaaagcct aatcgtgaaa ccgcagaatt   10800
gtatatgact tctggtaatc actattggaa tagtggaata ttcatgttta aggcatctgt   10860
ttatcttgag gaattgagaa aatttagacc tgacatttac aatgtttgtg aacaggttgc   10920
ctcatcctca tacattgatc tagattttat tcgattatca aaagaacaat tcaagattg    10980 tcctgctgaa tctattgatt ttgctgtaat ggaaaaaaca gaaaaatgtg ttgtatgccc   11040
tgttgatatt ggtggagtg acgttggatc ttggcaatcg ttatgggaca ttagtctaaa    11100
atcgaaaaca ggagatgtat gtaaaggtga tatattaacc tatgatacta agaataatta   11160
tatctactct gagtcagcgt tggtagccgc cattggaatt gaagatatgg ttatcgtgca   11220
aactaaagat gccgttcttg tgtctaaaaa gagtgatgta cagcatgtaa aaaaaatagt   11280
cgaaatgctt aaattgcagc aacgtacaga gtatattagt catcgtgaag ttttccgacc   11340
atggggaaaa tttgattcga ttgaccaagg tgagcgatac aaagtcaaga aaattattgt   11400
gaaacctggt gaggggcttt ctttaaggat gcatcaccat cgttctgaac attggatcgt   11460
```

```
gctttctggt acagcaaaag taacccttgg cgataaaact aaactagtca ccgcaaatga   11520
atcgatatac attccccttg cgcagcgta tagtcttgag aatccgggca taatccctct    11580
taatcttatt gaagtcagtt caggggatta tttgggagag gatgatatta taagacagaa   11640
agaacgttac aaacatgaag attaacatat gaaatcttta acctgcttta aagcctatga   11700
tattcgcggg aaattaggcg aagaactgaa tgaagatatt gcctggcgca ttgggcgtgc   11760
ctatggcgaa tttctcaaac cgaaaaccat tgtttaggc ggtgatgtcc gcctcaccag    11820
cgaagcgtta aaactggcgc ttgcgaaagg tttacaggat gcgggcgtcg atgtgctgga   11880
tatcggtatg tccggcaccg aagagatcta tttcgccacg ttccatctcg gagtggatgg   11940
cggcatcgaa gttaccgcca gccataaccc gatggattac aacggcatga agctggtgcg   12000
cgaaggggct cgcccgatca gcggtgatac cggactgcgc gatgtccagc gtctggcaga   12060
agccaatgac ttccctcctg tcgatgaaac caaacgtggt cgctatcagc aaatcaatct   12120
gcgtgacgct tacgttgatc acctgttcgg ttatatcaac gtcaaaaacc tcacgccgct   12180
caagctggtg atcaactccg ggaacggcgc agcgggtccg gtggtggacg ccattgaagc   12240
ccgatttaaa gccctcggcg caccggtgga attaatcaaa gtacacaaca cgccggacgg   12300
caatttcccc aacggtattc ctaacccgct gctgccggaa tgccgcgacg acaccccgtaa  12360 tgcggtcatc aaaacacggcg cggatatggg cattgccttt gatggcgatt ttgaccgctg   12420
tttcctgttt gacgaaaaag ggcagtttat cgagggctac tacattgtcg gcctgctggc   12480
agaagcgttc ctcgaaaaaa atcccggcgc gaagatcatc cacgatccac gtctctcctg   12540
gaacaccgtt gatgtggtga ctgccgcagg cggcaccccg gtaatgtcga aaaccggaca    12600
cgcctttatt aaagaacgta tgcgcaagga agacgccatc tacggtggcg aaatgagcgc   12660
tcaccattac ttccgtgatt tcgcttactg cgacagcggc atgatcccgt ggctgctggt   12720
cgccgaactg gtgtgcctga aaggaaaaac gctgggcgaa atggtgcgcg accggatggc   12780
ggcgtttccg gcaagcggtg agatcaacag caaactggcg caacccgttg aggcaattaa   12840
tcgcgtggaa cagcatttta ccgcgaggc gctggcggtg gatcgcaccg atggcatcag   12900
catgaccttt gccgactggc gctttaacct gcgctcctcc aacaccgaac cggtggtgcg   12960
gttgaatgtg gaatcacgcg gtgatgtaaa gctaatggaa aagaaaacta aagctcttct   13020
taaattgcta agtgagtgat tatttacatt aatcattaag cgtatttaag attatattaa    13080
agtaatgtta ttgcggtata tgatgaatat gtgggctttt ttatgtataa cgactatacc   13140
gcaactttat ctaggaaaag attaatgaaa ataaagttttt gtactgacca atttgcattt   13200
cacgtcacga ttgagacgtt cctttgctta agacattttt tcatcgctta tgtaataaca   13260
aatgtgcctt atataaaaag gagaacaaaa tggaacttaa aataattgag acaatagatt   13320
tttattatcc ctgtttacga tattatagcc aaagttgtat cctgcatcag tcctgcaata   13380
tttcacgagt gctttgttaa ctgaatacat gtctgccatt ttccagatga taacgacgtc   13440
atcgcaattg atggtaaaac acttcggcac acttatgaca agagtcgtcg cagaggagtg   13500
gttcatgtca ttagtgcgtt tcagcaatgc acagtctggt cctcggatag atcaagacgg   13560
atgagaaacc taatgcgttc acagttattc atgaactttc taaatgatg ggtattaaag    13620 gaaaaataat cataactgat gcgatggctt gccagaaaga tattgcagag aagatataaa   13680
aacagagatg tgattatta ttcgctgtaa aaggaaataa gagtcggctt aatagagtct    13740 ttgagggagat atttacgctg aaagaattaa ataatccaaa acatgacagt tacgcaatta   13800
gtgaaaagag gcacggcaga gacgatgtcc gtcttcatat tgtttgagat gctcctgatg   13860
```

```
agcttattga tttcacgttt gaatggaaag ggctgcagaa tttatgaatg gcagtccact    13920
ttctctcaat aatagcagag caaaagaaag aatccgaaat gacgatcaaa tattatatta    13980
gatctgctgc tttaaccgca gagaagttcg ccacagtaaa tcgaaatcac tggcgcatgg    14040
agaataagtt gcacagtagc ctgatgtggt aatgaatgaa atcgactata atataagaag    14100
gcgagttgca ttcgaatgat tttctagaat gcggcacatc gctattaata tctgacaatg    14160
ataatgtatt caaggcagga ttatcatgta agatgcgaaa agcagtcatg gacagaaact    14220
tcctagcgtc aggcattgca gcgtgcgggc tttcataatc ttgcattggt tttgataaga    14280
tatttctttg gagatgggaa aatgaatttg tatggtattt ttggtgctgg aagttatggt    14340
agagaaacaa tacccattct aaatcaacaa ataaagcaag aatgtggttc tgactatgct    14400
ctggtttttg tggatgatgt tttggcagga aagaaagtta atggttttga agtgctttca    14460
accaactgct ttctaaaagc cccttattta aaaagtatt ttaatgttgc tattgctaat    14520
gataagatac gacagagagt gtctgagtca atattattac acggggttga accaataact    14580
ataaaacatc caaatagcgt tgtttatgat catactatga taggtagtgg cgctattatt    14640 tctcccttg ttacaatatc tactaatact catataggga ggttttttca tgcaaacata    14700
tactcatacg ttgcacatga ttgtcaaata ggagactatg ttacatttgc tcctggggct    14760
aaatgtaatg gatatgttgt tattgaagac aatgcatata taggctcggg tgcagtaatt    14820
aagcagggtg ttcctaatcg cccacttatt attggcgcgg gagccattat aggtatgggg    14880
gctgttgtca ctaaaagtgt tcctgccggt ataactgtgt gcggaaatcc agcaagagaa    14940
atgaaaagat cgccaacatc tatttaatgg gaatgcgaaa acacgttcca aatgggacta    15000
atgtttaaaa tatatataat ttcgctaatt tactaaatta tggcttcttt ttaagctatc    15060
ctttacttag ttattactga tacagcatga aatttataat actctgatac attttatac    15120 gttattcaag ccgcatatct agcggtaacc cctgacagga gtaaacaatg tcaaagcaac    15180
agatcggcgt agtcggtatg gcagtgatgg ggcgcaacct tgcgctcaac atcgaaagcc    15240
gtggttatac cgtctctatt ttcaaccgtt cccgtgaaaa gacggaagaa gtgattgccg    15300
aaaatccagg caagaaactg gttccttact atacggtgaa agaatttgtt gaatctctgg    15360
aaacgcctcg tcgcatcttg ttaatggtga aagcaggtgc aggcacggat gctgctattg    15420
attcccttaa gccataccte gataaaggtg acatcatcat tgatggtggt aatacctct    15480 tccaggacac cattcgtcgt aaccgtgagc tttctgcaga aggctttaac ttcatcggta    15540
ccggtgtttc cggtggtgag gagggcgcac taaaaggtcc ttccattatg cctggtgggc    15600
agaaagaagc ctatgaacta gttgcgccga tcctgaccaa aatcgccgca gtggctgaag    15660 acggtgagc atgcgttacc tatattggtg ccgatgcgc aggtcactat gtgaagatgg    15720
ttcacaacgg tattgaatac ggcgatatgc agctgattgc tgaagcctat tctctgctta    15780
aaggtggtct gaacctcacc aacgaagaac tggcgcagat ctttaccgag tggaataacg    15840
gtgaactgag cagctacctg atcgacatta ccaaagacat cttcactaaa aaagatgaag    15900
acggtaacta cctggttgat gtgatcctgg atgaagcggc aaacaaaggt acgggcaaat    15960
ggaccagcca gagcgcactg gatctcggcg aaccgctgtc gctgattacc gagtctgtgt    16020
ttgcacgata catctcttct ctgaaagatc agcgcgttgc tgcgtctaaa gttctctctg    16080
gcccacaagc gcagccagct ggcgacaagg ctgagttcat cgaaaaagtt cgccgtgcac    16140
tgtatctggg caaaatcgtt tcttacgctc aggggttctc tcaactgcgt gcggcgtctg    16200
```

```
aagagtacaa ctgggatctg aactacggcg aaatcgcgaa gattttccgt gctggctgca    16260
tcatccgtgc gcagttcctg cagaaaatca ccgatgctta tgccgaaaat ccgcagatcg    16320
ctaacctgct gctggctcct tacttcaagc aaattgccga tgactaccag caggcgctgc    16380
gcgatgtcgt cgcttatgcg gtacagaacg gtatcccggt tccgaccttc gccgctgcgg    16440
ttgcctatta tgacagctac cgcgccgctg ttctgcctgc gaacctgatc caggcacagc    16500
gtgactattt cggtgcgcat acttataagc gcattgataa agaaggtgtg ttccataccg    16560
aatggctgga ttaagcggcc gc                                             16582

<210> SEQ ID NO 80
<211> LENGTH: 32
<212> TYPE: DNA
<213> ORGANISM: Artificial Sequence
<220> FEATURE:
<223> OTHER INFORMATION: p184

<400> SEQUENCE: 80
atatggcgcg cctctgagtt acaacagtcc gc                                  32

<210> SEQ ID NO 81
<211> LENGTH: 32
<212> TYPE: DNA
<213> ORGANISM: Artificial Sequence
<220> FEATURE:
<223> OTHER INFORMATION: p184

<400> SEQUENCE: 81
ataagcggcc gcttcaggtg ctacatttga ag                                  32

<210> SEQ ID NO 82
<211> LENGTH: 2488
<212> TYPE: DNA
<213> ORGANISM: Artificial Sequence
<220> FEATURE:
<223> OTHER INFORMATION: pACYC184

<400> SEQUENCE: 82
ggcgcgcctc tgagttacaa cagtccgcac cgctgtccgg tagctccttc cggtgggcgc    60
ggggcatgac tatcgtcgcc gcacttatga ctgtcttctt tatcatgcaa ctcgtaggac    120
aggtgccggc agcgcccaac agtccccccgg ccacggggcc tgccaccata cccacgccga    180
aacaagcgcc ctgcaccatt atgttccgga tctgcatcgc aggatgctgc tggctaccct    240
gtggaacacc tacatctgta ttaacgaagc gctaaccgtt tttatcaggc tctgggaggc    300
agaataaatg atcatatcgt caattattac ctccacgggg agagcctgag caaactggcc    360
tcaggcattt gagaagcaca cggtcacact gcttccggta gtcaataaac cggtaaacca    420
gcaatagaca taagcggcta tttaacgacc ctgccctgaa ccgacgaccg ggtcgaattt    480
gctttcgaat ttctgccatt catccgctta ttatcactta ttcaggcgta gcaccaggcg    540
tttaagggca ccaataactg ccttaaaaaa attacgcccc gccctgccac tcatcgcagt    600
actgttgtaa ttcattaagc attctgccga catggaagcc atcacagacg gcatgatgaa    660
cctgaatcgc cagcggcatc agcaccttgt cgccttgcgt ataatatttg cccatggtga    720
aaacgggggc gaagaagttg tccatattgg ccacgtttaa atcaaaactg gtgaaactca    780
cccagggatt ggctgagacg aaaaacatat tctcaataaa cccttaggg aaataggcca    840 ggttttcacc gtaacacgcc acatcttgcg aatatatgtg tagaaactgc cggaaatcgt    900
cgtggtattc actccagagc gatgaaaacg tttcagtttg ctcatggaaa acggtgtaac    960
```

```
aagggtgaac actatcccat atcaccagct caccgtcttt cattgccata cggaattccg    1020
gatgagcatt catcaggcgg gcaagaatgt gaataaaggc cggataaaac ttgtgcttat    1080
ttttctttac ggtctttaaa aaggccgtaa tatccagctg aacggtctgg ttataggtac    1140
attgagcaac tgactgaaat gcctcaaaat gttctttacg atgccattgg gatatatcaa    1200
cggtggtata tccagtgatt tttttctcca ttttagcttc cttagctcct gaaaatctcg    1260
ataactcaaa aaatacgccc ggtagtgatc ttatttcatt atggtgaaag ttggaacctc    1320
ttacgtgccg atcaacgtct cattttcgcc aaaagttggc ccagggcttc ccggtatcaa    1380
cagggacacc aggatttatt tattctgcga agtgatcttc cgtcacaggt atttattcgg    1440
cgcaaagtgc gtcgggtgat gctgccaact tactgattta gtgtatgatg gtgtttttga    1500
ggtgctccag tggcttctgt ttctatcagc tgtccctcct gttcagctac tgacggggtg    1560
gtgcgtaacg gcaaaagcac cgccggacat cagcgctagc ggagtgtata ctggcttact    1620
atgttggcac tgatgagggt gtcagtgaag tgcttcatgt ggcaggagaa aaaaggctgc    1680
accggtgcgt cagcagaata tgtgatacag gatatattcc gcttcctcgc tcactgactc    1740
gctacgctcg gtcgttcgac tgcggcgagc ggaaatggct tacgaacggg gcggagattt    1800
cctggaagat gccaggaaga tacttaacag ggaagtgaga gggccgcggc aaagccgttt    1860
ttccataggc tccgcccccc tgacaagcat cacgaaatct gacgctcaaa tcagtggtgg    1920
cgaaacccga caggactata aagataccag gcgtttcccc ctggcggctc cctcgtgcgc    1980
tctcctgttc ctgcctttcg gtttaccggt gtcattccgc tgttatggcc gcgtttgtct    2040
cattccacgc ctgacactca gttccgggta ggcagttcgc tccaagctgg actgtatgca    2100 cgaaccccccc gttcagtccg accgctgcgc cttatccggt aactatcgtc ttgagtccaa    2160
cccggaaaga catgcaaaag caccactggc agcagccact ggtaattgat ttagaggagt    2220
tagtcttgaa gtcatgcgcc ggttaaggct aaactgaaag acaagttttt ggtgactgcg    2280
ctcctccaag ccagttacct cggttcaaag agttggtagc tcagagaacc ttcgaaaaac    2340
cgccctgcaa ggcggttttt tcgttttcag agcaagagat tacgcgcaga ccaaaacgat    2400
ctcaagaaga tcatcttatt aatcagataa aatatttcta gatttcagtg caatttatct    2460
cttcaaatgt agcacctgaa gcggccgc                                      2488
```